United States Patent
Zeng et al.

(10) Patent No.: US 8,980,920 B2
(45) Date of Patent: Mar. 17, 2015

(54) ANTIVIRAL COMPOUNDS OF THREE LINKED ARYL MOIETIES TO TREAT DISEASES SUCH AS HEPATITIS C

(75) Inventors: Qingbei Zeng, Edison, NJ (US); Kevin X. Chen, Edison, NJ (US); Anilkumar Gopinadhan Nair, Edison, NJ (US); Stuart B. Rosenblum, West Orange, NJ (US); Joseph A. Kozlowski, Princeton, NJ (US); F. George Njoroge, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 622 days.

(21) Appl. No.: 13/375,094

(22) PCT Filed: May 28, 2010

(86) PCT No.: PCT/US2010/036523
§ 371 (c)(1),
(2), (4) Date: Jun. 11, 2012

(87) PCT Pub. No.: WO2010/138791
PCT Pub. Date: Dec. 2, 2010

(65) Prior Publication Data
US 2012/0258078 A1   Oct. 11, 2012

Related U.S. Application Data

(60) Provisional application No. 61/182,401, filed on May 29, 2009.

(51) Int. Cl.
| | |
|---|---|
| A61K 31/41 | (2006.01) |
| A61K 31/4192 | (2006.01) |
| A61K 31/4439 | (2006.01) |
| A61K 31/423 | (2006.01) |
| A61K 31/5377 | (2006.01) |
| A61K 31/496 | (2006.01) |
| A61K 31/427 | (2006.01) |

(Continued)

(52) U.S. Cl.
CPC ..................... C07D 403/14 (2013.01)
USPC ..... 514/314; 546/173; 546/273.4; 548/302.7; 548/304.7; 548/312.7; 514/338; 514/363; 514/364; 514/365; 514/374; 514/379; 514/381; 514/383; 514/393; 514/394; 514/397; 514/398

(58) Field of Classification Search
USPC ................ 548/302.7, 304.7, 312.7; 546/173, 546/273.4; 514/314, 338, 364, 365, 374, 514/379, 381, 383, 393, 394, 397, 398
See application file for complete search history.

(56) References Cited

U.S. PATENT DOCUMENTS

| | | |
|---|---|---|
| 5,935,982 A | 8/1999 | Dykstra et al. |
| 7,438,920 B1 | 10/2008 | Kim et al. |

(Continued)

FOREIGN PATENT DOCUMENTS

| | | | |
|---|---|---|---|
| WO | 0020400 | 4/2000 | |
| WO | WO-2008/021927 | * 2/2008 | ........... C07D 401/14 |

(Continued)

OTHER PUBLICATIONS

Wachowius et al. Synthesis and DNA duplex recognition of a triplex-forming oligonucleotide with an ureide-substituted 4-phenylimidazole nucleoside. Tetrahedron Letters 2008, 49:7264-7267.

Pujals et al. "Replacement of a proline with a silaproline causes a 20-fold increase in the cellular uptake of a Pro-Rich Peptide." J. Am. Chem. Soc. 2006, 128:8479-8483.

Uwe Koch and Frank Narjes: "Recent Progress in the Development of Inhibitors of the Hepatitis C Virus RNA-Dependent RNA Polymerase" Current Topics in Medicinal Chemistry, Bentham Science Publishers Ltd, Netherlands, vol. 7, Jan. 1, 2007, pp. 1302-1329.

*Primary Examiner* — Kamal Saeed
*Assistant Examiner* — Janet L Coppins
(74) *Attorney, Agent, or Firm* — Jeffrey P. Bergman; Laura M. Ginkel

(57) ABSTRACT

The present invention relates to novel Linked Tricyclic Aryl Compounds, compositions comprising at least one Linked Tricyclic Compound, and methods of using Linked Tricyclic Aryl Compounds for treating or preventing HCV infection in a patient. in one aspect, the present invention provides Compounds of Formula (I): and pharmaceutically acceptable salts thereof, wherein: Non-limiting examples of the Compounds of Formula (II) include compound 56.

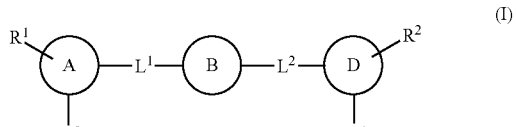

(I)

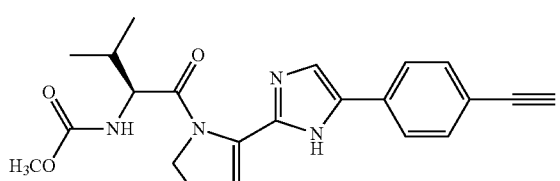

(56)

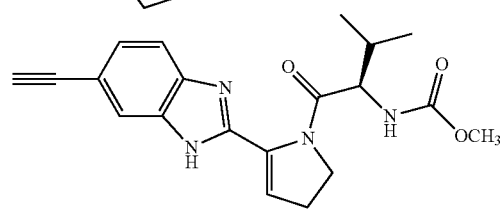

8 Claims, No Drawings

(51) Int. Cl.

| | |
|---|---|
| *A61K 31/422* | (2006.01) |
| *A61K 31/4196* | (2006.01) |
| *C07D 213/60* | (2006.01) |
| *C07D 233/64* | (2006.01) |
| *C07D 235/04* | (2006.01) |
| *C07D 239/28* | (2006.01) |
| *C07D 241/14* | (2006.01) |
| *C07D 403/14* | (2006.01) |

(56) References Cited

U.S. PATENT DOCUMENTS

| | | |
|---|---|---|
| 7,659,270 B2 | 2/2010 | Bachand et al. |
| 7,906,655 B2 | 3/2011 | Belema et al. |
| 8,147,818 B2 | 4/2012 | Bachand et al. |
| 8,303,944 B2 | 11/2012 | Bachand et al. |
| 8,420,686 B2 | 4/2013 | Or et al. |
| 8,426,458 B2 | 4/2013 | Or et al. |
| 2006/0019974 A1 | 1/2006 | Mederski et al. |
| 2006/0258682 A1 | 11/2006 | Liao et al. |
| 2007/0032497 A1 | 2/2007 | Hashimoto et al. |
| 2007/0049593 A1 | 3/2007 | Oka et al. |
| 2007/0185175 A1 | 8/2007 | Liu et al. |
| 2008/0044379 A1 | 2/2008 | Bachand et al. |
| 2008/0200423 A1 | 8/2008 | Cook et al. |
| 2009/0202478 A1 | 8/2009 | Bachand et al. |
| 2009/0202483 A1 | 8/2009 | Bachand et al. |
| 2010/0055071 A1 | 3/2010 | Leivers et al. |
| 2010/0087382 A1 | 4/2010 | Bailey et al. |
| 2010/0233122 A1 | 9/2010 | Qiu et al. |
| 2010/0316607 A1 | 12/2010 | Or et al. |
| 2011/0223134 A1 | 9/2011 | Nair et al. |
| 2012/0083483 A1 | 4/2012 | Coburn et al. |
| 2012/0251491 A1 | 10/2012 | Rosenblum et al. |
| 2012/0258078 A1 | 10/2012 | Rosenblum et al. |
| 2012/0276047 A1 | 11/2012 | Rosenblum et al. |
| 2013/0156731 A1 | 6/2013 | Chen et al. |

FOREIGN PATENT DOCUMENTS

| | | | |
|---|---|---|---|
| WO | 2010065681 | 6/2010 | |
| WO | WO-2010/065668 | * 6/2010 | ........... A61K 31/415 |
| WO | 2010096777 | 8/2010 | |
| WO | 2010138790 | 12/2010 | |
| WO | 2011075439 | 6/2011 | |

* cited by examiner

ANTIVIRAL COMPOUNDS OF THREE LINKED ARYL MOIETIES TO TREAT DISEASES SUCH AS HEPATITIS C

CROSS-REFERENCE TO RELATED APPLICATIONS

This application is the national stage application under 35 U.S.C. 371 of international Patent Application No. PCT/US2010/036523, filed May 28, 2010, which claims priority to U.S. Provisional Application No. 61/182,401, filed May 29, 2009. Each of the aforementioned PCT and priority applications is incorporated by reference in its entirety.

FIELD OF THE INVENTION

The present invention relates to novel Linked Tricyclic Aryl Compounds, compositions comprising at least one Linked Tricyclic Compound, and methods of using Linked Tricyclic Aryl Compounds for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal. HCV is a (+)-sense single-stranded enveloped RNA virus that has been implicated as the major causative agent in non-A, non-B hepatitis (NANBH), particularly in blood-associated NANBH (BB-NANBH) (see International Publication No. WO 89/04669 and European Patent Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

It is well-established that persistent infection of HCV can result in chronic hepatitis, and as such, inhibition of HCV replication is a viable strategy for the prevention of hepatocellular carcinoma. Current therapies for HCV infection include α-interferon monotherapy and combination therapy comprising α-interferon and ribavirin. These therapies have been shown to be effective in some patients with chronic HCV infection, but suffer from poor efficacy and unfavorable side-effects and there are currently efforts directed to the discovery of HCV replication inhibitors that are useful for the treatment and prevention of HCV related disorders.

Current research efforts directed toward the treatment of HCV includes the use of antisense oligonucleotides, free bile acids (such as ursodeoxycholic acid and chenodeoxycholic acid) and conjugated bile acids (such as tauroursodeoxycholic acid). Phosphonoformic acid esters have also been proposed as potentially useful for the treatment of various viral infections, including HCV. Vaccine development, however, has been hampered by the high degree of viral strain heterogeneity and immune evasion and the lack of protection against reinfection, even with the same inoculum.

In light of these treatment hurdles, the development of small-molecule inhibitors directed against specific viral targets has become a major focus of anti-HCV research. The determination of crystal structures for NS3 protease, NS3 RNA helicase, NS5A, and NS5B polymerase, with and without bound ligands, has provided important structural insights useful for the rational design of specific inhibitors.

Inhibitors of HCV NS5A have demonstrated efficacy in treating HCV infection in humans. HCV NS5A is a 447 amino acid phosphoprotein which currently lacks a defined enzymatic function. It migrates as 56 kd and 58 kd bands on gels depending on phosphorylation state (Tanji, et al. *J. Virol.* 69:3980-3986 (1995)). HCV NS5A resides in a replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478.

Other NS5A inhibitors and their use for reducing viral load in HCV infected humans have been described in U.S. Patent Publication No. US20060276511.

Despite the intensive effort directed at the treatment and prevention of HCV and related viral infections, there exists a need in the art for small-molecule compounds having desirable or improved physicochemical properties that are useful for inhibiting viruses and treating viral infections and virus-related disorders. This invention addresses that need.

SUMMARY OF THE INVENTION

In one aspect, the present invention provides Compounds of Formula (I):

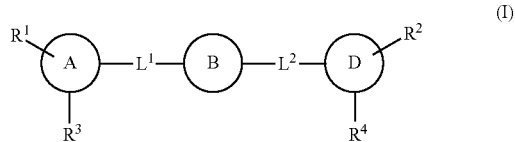

(I)

and pharmaceutically acceptable salts thereof, wherein:

A is 5-membered monocyclic heteroaryl or bicyclic heteroaryl, wherein said 5-membered monocyclic heteroaryl group or said bicyclic heteroaryl group can be optionally and independently substituted on one or more ring carbon atoms by $C_1$-$C_6$ alkyl, —O—($C_1$-$C_6$ alkyl) or halo;

B is arylene or heteroarylene, wherein said arylene group can be substituted with $R^{12}$; and wherein said heteroarylene group can be optionally and independently substituted on one or more ring nitrogen atoms with $R^{10}$ and on one or more ring carbon atoms with $R^{12}$; such that when B is a multicyclic ring system, then A and D are each bonded to the same ring of B;

D is 5-membered monocyclic heteroaryl or bicyclic heteroaryl, wherein said 5-membered monocyclic heteroaryl group or said bicyclic heteroaryl group can be optionally and independently substituted on one or more ring carbon atoms by $C_1$-$C_6$ alkyl, —O—($C_1$-$C_6$ alkyl) or halo;

$L^1$ is a bond, —[C($R^{13}$)$_2$]$_q$—, —[C($R^{13}$)$_2$]$_m$—C($R^{13}$)=C($R^{13}$)—[C($R^{13}$)$_2$]$_m$—, —[C($R^{13}$)$_2$]$_m$—(C≡C)$_q$—[C($R^{13}$)$_2$]$_m$—, —[C($R^{13}$)$_2$]$_m$—N($R^{14}$)—[C($R^{13}$)$_2$]$_m$—, -alkylene-C(O)—, —C(O)— or —CF$_2$—;

$L^2$ is a bond, —[C($R^{13}$)$_2$]$_q$—, —[C($R^{13}$)$_2$]$_m$—C($R^{13}$)=C($R^{13}$)—[C($R^{13}$)$_2$]$_m$—, —[C($R^{13}$)$_2$]$_m$—(C≡C)$_q$—[C($R^{13}$)$_2$]$_m$—, —[C($R^{13}$)$_2$]$_m$—N($R^{14}$)—[C($R^{13}$)$_2$]$_m$—, -alkylene-C(O)—, —C(O)— or —CF$_2$—; such that at least one of $L^1$ and $L^2$ is other than a bond;

$R^1$ is selected from:

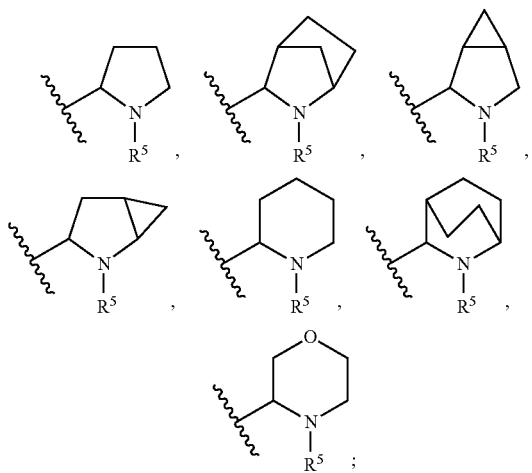

wherein an $R^1$ group can be optionally and independently substituted with:
(a) one to three groups, which can be the same or different, and are selected from halo, —OH, —$C_1$-$C_3$ alkyl, —O—($C_1$-$C_3$ alkyl) and —$C_1$-$C_3$ haloalkyl, or
(b) one to seven $^2$H groups;
or an $R^1$ group can be optionally fused to a $C_3$-$C_5$ cycloalkyl group at two of the $R^1$ group's adjacent ring carbon atoms, or an $R^1$ group can form a spirocycle with a cyclopentyl, cyclobutyl, cyclopropyl or cyclohexyl group at one of the $R^1$ group's ring carbon atoms;

$R^2$ is selected from:

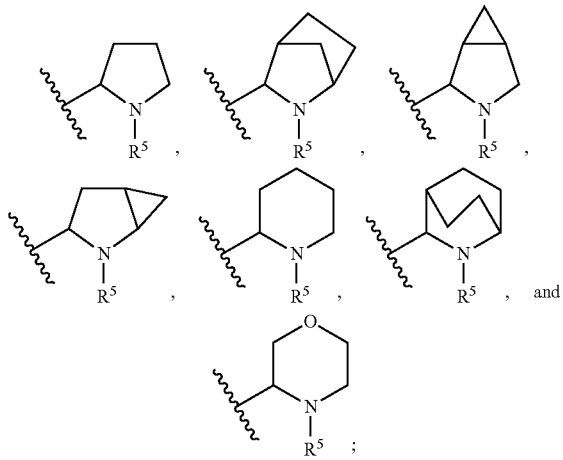

wherein an $R^2$ group can be optionally and independently substituted with:
(a) one to three groups, which can be the same or different, and are selected from halo, —OH, —$C_1$-$C_3$ alkyl, —O—($C_1$-$C_3$ alkyl) and —$C_1$-$C_3$ haloalkyl, or
(b) one to seven $^2$H groups;
or an $R^2$ group can be optionally fused to a $C_3$-$C_5$ cycloalkyl group at two of the $R^2$ group's adjacent ring carbon atoms, or an $R^2$ group can form a spirocycle with a cyclopentyl, cyclobutyl, cyclopropyl or cyclohexyl group at one of the $R^2$ group's ring carbon atoms;

each occurrence of $R^5$ is independently selected from:
(a) —C(O)—($C_1$-$C_6$ alkyl), optionally substituted by one to eight $R^3$ groups, wherein each occurrence of $R^3$ is independently selected from:
(i) —O—($C_1$-$C_3$ alkyl),
(ii) phenyl, which can be optionally and independently substituted with one to four groups, selected from halo, $C_1$-$C_3$ alkyl and —O—($C_1$-$C_3$ alkyl),
(iii) —$NH_2$,
(iv) —NH($C_1$-$C_3$ alkyl),
(v) —N($C_1$-$C_3$ alkyl)$_2$,
(vi) —NHC(O)—O—($C_1$-$C_6$ alkyl),
(vii) —N($C_1$-$C_3$ alkyl)-C(O)—O—($C_1$-$C_6$ alkyl),
(viii) $C_1$-$C_3$ fluoroalkyl,
(ix) $C_2$-$C_6$ alkynyl,
(x) $C_3$-$C_7$ cycloalkyl,
(xi) pyrrolidinyl,
(xii) piperidinyl,
(xiii) pyranyl,
(xiv) —$NHSO_2$-alkyl, and
(xv) $^2$H;
(b)

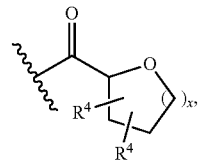

wherein x is 1 or 2, and each occurrence of $R^4$ is independently selected from the group consisting of H, $C_1$-$C_3$ alkyl, —O—($C_1$-$C_3$ alkyl) and F; and
(c) H;

each occurrence of $R^{10}$ is independently H, —$C_1$-$C_6$ alkyl, —[C($R^{12}$)$_2$]$_p$-(3 to 7-membered cycloalkyl), —[C($R^{12}$)$_2$]$_p$-(4 to 7-membered heterocycloalkyl), —[C($R^{12}$)$_2$]$_p$-aryl, —[C($R^{12}$)$_2$]$_p$-heteroaryl, —$C_1$-$C_6$ haloalkyl or —$C_1$-$C_6$ hydroxyalkyl, wherein said 3 to 7-membered cycloalkyl group, said 4 to 7-membered heterocycloalkyl group, said aryl group or said heteroaryl group can be optionally and independently substituted with up to two $R^{13}$ groups, and wherein two $R^{10}$ groups that are attached to a common nitrogen atom, together with the nitrogen atom to which they are attached, can optionally join to form a 4 to 7-membered heterocycloalkyl group;
each occurrence of $R^{12}$ is independently H, halo, —$C_1$-$C_6$haloalkyl, —CN,
—$C_1$-$C_6$ alkyl, —$C_1$-$C_6$ alkylene-OR$^{16}$, —$C_1$-$C_6$ alkylene-N($R^{15}$)$_2$, —C(O)—($C_1$-$C_6$ alkyl), —OR$^{16}$, —NHC(O)—($C_1$-$C_6$ alkyl), 3 to 7-membered cycloalkyl, 3 to 7-membered heterocycloalkyl, aryl or heteroaryl, wherein said 3 to 7-membered cycloalkyl group, said 3 to 7-membered heterocycloalkyl group, said aryl group or said heteroaryl group can be optionally and independently substituted with up to 3 substituents, which can be the same or different, and are selected from $C_1$-$C_6$ alkyl, halo, —$C_1$-$C_6$haloalkyl, —$C_1$-$C_6$ hydroxyalkyl, —OH, —C(O)NH—($C_1$-$C_6$ alkyl), —C(O)N($C_1$-$C_6$alkyl)$_2$, —O—($C_1$-$C_6$ alkyl), —$NH_2$, —NH($C_1$-$C_6$ alkyl), —N($C_1$-$C_6$alkyl)$_2$ and —NHC(O)—($C_1$-$C_6$ alkyl);
each occurrence of $R^{13}$ is independently H, —$C_1$-$C_6$ haloalkyl, —$C_1$-$C_6$ alkyl, —($C_1$-$C_6$ alkylene)-O—($C_1$-$C_6$ alkyl), —C(O)—($C_1$-$C_6$ alkyl), —C(O)O($C_1$-$C_6$ alkyl);

each occurrence of $R^{14}$ is independently H, —$C_1$-$C_6$ alkyl, 3 to 6-membered cycloalkyl or 4 to 6-membered heterocycloalkyl;

each occurrence of $R^{15}$ is independently H, —$C_1$-$C_6$ alkyl, —$C_1$-$C_6$ haloalkyl, 3 to 7-membered cycloalkyl, 4 to 7-membered heterocycloalkyl, aryl or heteroaryl, such that two $R^{15}$ groups that are attached to a common nitrogen atom, together with the nitrogen atom to which they are attached, can optionally join to form a 4 to 7-membered heterocycloalkyl group;

each occurrence of $R^{16}$ is independently H, —$C_1$-$C_6$ alkyl, —$C_1$-$C_6$haloalkyl, 3 to 7-membered cycloalkyl, 4 to 7-membered heterocycloalkyl, aryl or heteroaryl;

each occurrence of m is independently 0 or 1;

each occurrence of p is independently an integer ranging from 0 to 3; and each occurrence of q is independently an integer ranging from 1 to 3.

The Compounds of Formula (I) (also referred to herein as the "Linked Tricyclic Aryl Compounds") and pharmaceutically acceptable salts thereof can be useful, for example, for inhibiting HCV viral replication or replicon activity, and for treating or preventing HCV infection in a patient.

The Tricyclic Compounds or pharmaceutically acceptable salts thereof can also be useful for treating or preventing HCV infection in a patient.

Accordingly, the present invention provides methods for treating or preventing HCV infection in a patient, comprising administering to the patient an effective amount of at least one Tricyclic Compound.

The present invention also provides pharmaceutical compositions comprising an effective amount of at least one Tricyclic Compound or a pharmaceutically acceptable salt thereof, and a pharmaceutically acceptable carrier. The compositions can be useful for treating or preventing HCV infection in a patient.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention provides Linked Tricyclic Aryl Compounds, pharmaceutical compositions comprising at least one Linked Tricyclic Compound, and methods of using the Linked Tricyclic Aryl Compounds for treating or preventing a viral infection or a virus-related disorder in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Fused Aryl Tricyclic Compound and/or an additional therapeutic agent, or a composition thereof that is effective in producing the desired therapeutic, ameliorative, inhibitory or preventative effect when administered to a patient suffering from HCV infection. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In another embodiment, an alkyl group contains from about 1 to about 6 carbon atoms. In another embodiment, an alkyl group contains from about 1 to about 3 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched. The term "$C_1$-$C_6$ alkyl" refers to an alkyl group having from 1 to 6 carbon atoms. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkenyl group is unsubstituted. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkynyl group is unsubstituted. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In one embodiment, an alkylene group has from 1 to about 3 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is unsubstituted. In another embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

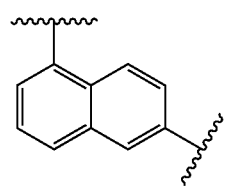

is understood to represent both:

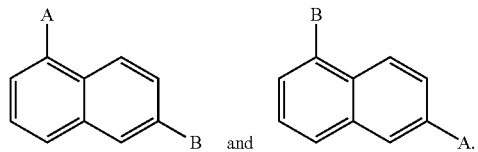

In one embodiment, an arylene group can be optionally fused to a cycloalkyl or cycloalkanoyl group. Non-limiting examples of arylene groups include phenylene and naphthalene. Unless otherwise indicated, an arylene group is unsubstituted. In one embodiment, an arylene group is unsubstituted. In another embodiment, an arylene group is:

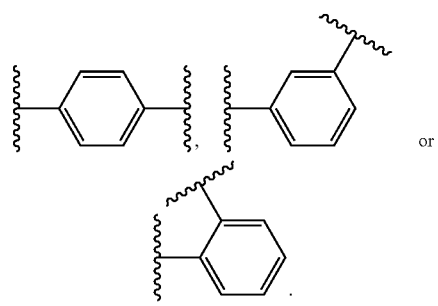

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, that is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. The term "4 to 7-membered cycloalkyl" refers to a cycloalkyl group having from 4 to 7 ring carbon atoms. A ring carbon atom of a cycloalkyl group may be functionalized as a carbonyl group. Unless otherwise indicated, a cycloalkyl group is unsubstituted. An illustrative example of such a cycloalkyl group (also referred to herein as a "cycloalkanoyl" group) includes, but is not limited to, cyclobutanoyl:

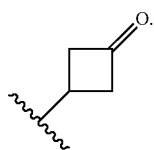 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is unsubstituted. In another embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms. Unless otherwise indicated, a cycloalkenyl group is unsubstituted.

The term "halo," as used herein, means —F, —Cl, —Br or —I. In one embodiment, a halo group is —F or —Cl. In another embodiment, a halo group is —F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms and is substituted with one or more halogen atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms substituted with up to 13 halogen atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl. In another embodiment, a heteroaryl group comprises a 5 ro 6-membered heteroaryl group fused to a benzene ring. The term "3 to 7-membered cycloalkyl" refers to a cycloalkyl group having from 3 to 8 ring carbon atoms. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. In one embodiment, a heteroarylene group has 5 to 10 ring atoms. In another embodiment, a heteroarylene group is monocyclic and has 5 or 6 ring atoms. In another embodiment, a heteroarylene group is bicyclic and has 9 or 10 ring atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, that is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

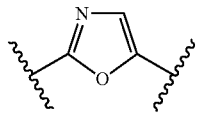 [SMILES: *c1cnc(*)o1]

is understood to represent both:

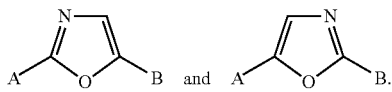

In one embodiment, a heteroarylene group is unsubstituted. In another embodiment, a heteroarylene group is a 5-membered heteroarylene. In another embodiment, a heteroarylene group is a 6-membered heteroarylene. In another embodiment, a heteroarylene group comprises a 5 or 6-membered heteroarylene group fused to a benzene ring. In another embodiment, a heteroarylene group is:

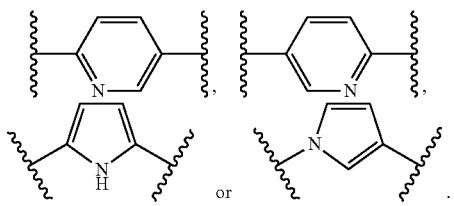

Unless otherwise indicated, a heteroarylene group is unsubstituted.

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. A heterocycloalkyl group can be joined via a ring carbon or ring nitrogen atom. In one embodiment, a heterocycloalkyl group has from about 3 to about 7 ring atoms. In another embodiment, a heterocycloalkyl group has 5 or 6 ring atoms. In another embodiment, a heterocycloalkyl group is monocyclic. In still another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, that is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone and the like, and all isomers thereof. A ring carbon atom of a heterocycloalkyl group may be functionalized as a carbonyl group. An illustrative example of such a heterocycloalkyl group is pyrrolidonyl:

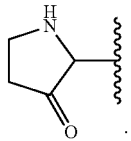

In one embodiment, a heterocycloalkyl group is unsubstituted. In another embodiment, a heterocycloalkyl group is a 5-membered heterocycloalkyl. In another embodiment, a heterocycloalkyl group is a 6-membered heterocycloalkyl. The term "3 to 7-membered cycloalkyl" refers to a heterocycloalkyl group having from 3 to 7 ring atoms. The term "4 to 7-membered cycloalkyl" refers to a heterocycloalkyl group having from 4 to 7 ring atoms. Unless otherwise indicated, a heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. In one embodiment, a heterocycloalkenyl group is unsubstituted. In another embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen atom attached to the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, hydroxy, hydroxyalkyl, haloalkyl, —O-alkyl, —O-haloalkyl, -alkylene-O-alkyl, —O-aryl, aralkoxy, acyl, aroyl, halo, nitro, cyano, —SF$_5$, carboxy, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), $Y_1Y_2N$—, $Y_1Y_2N$-alkyl-, $Y_1Y_2NC(O)$—, and $Y_1Y_2NS(O)_2$—, wherein $Y_1$ and $Y_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

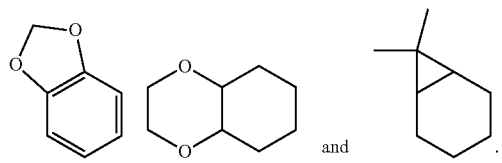

The term "substituted" means that one or more hydrogens on a designated atom is replaced with a selection from an indicated list of substituents, provided that the designated atom's normal valency under the existing circumstances is not exceeded, and that the substitution results in a stable compound. Combinations of substituents and/or variables are permissible only if such combinations result in stable compounds. The term "stable compound' or "stable structure" refers to a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Linked Tricyclic Aryl Compound or a pharmaceutically acceptable salt, hydrate or solvate of the compound. The transformation may occur by various mechanisms (e.g., by metabolic or chemical processes), such as, for example, through hydrolysis in blood.

For example, if a Linked Tricyclic Aryl Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a Linked Tricyclic Aryl Compound contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O$(C_1-C_6)$alkyl), or glycosyl (the radical resulting from the removal of a hydroxyl group of the hemiacetal form of a carbohydrate), and the like.

If a Linked Tricyclic Aryl Compound incorporates an amine functional group, a prodrug can be formed by the replacement of a hydrogen atom in the amine group with a group such as, for example, R-carbonyl-, RO-carbonyl-, NRR'-carbonyl—wherein R and R' are each independently $(C_1-C_{10})$alkyl, $(C_3-C_7)$cycloalkyl, benzyl, a natural □-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl; carboxy$(C_1-C_6)$alkyl; amino$(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or —O—$C_{1-4}$alkyl or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Linked Tricyclic Aryl Compounds can form salts which are also within the scope of this invention. Reference to a Linked Tricyclic Aryl Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Linked Tricyclic Aryl Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Linked Tricyclic Aryl Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Linked Tricyclic Aryl Compounds may be atropisomers (e.g., substituted biaryls) and are considered as part of this invention. Enantiomers can also be directly separated using chiral chromatographic techniques.

It is also possible that the Linked Tricyclic Aryl Compounds may exist in different tautomeric forms, and all such forms are embraced within the scope of the invention. For example, all keto-enol and imine-enamine forms of the compounds are included in the invention. It should also be noted that tautomeric forms such as, for example, the moieties:

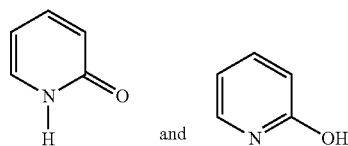 [SMILES: O=c1cccc[nH]1 ; Oc1ccccn1]

are considered equivalent in certain embodiments of this invention.

All stereoisomers (for example, geometric isomers, optical isomers and the like) of the present compounds and salts thereof, such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). If a Linked Tricyclic Aryl Compound incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Linked Tricyclic Aryl Compounds, and of the salts of the Linked Tricyclic Aryl Compounds, are intended to be included in the present invention.

The following abbreviations are used below and have the following meanings: AcCl is acetyl chloride; BOC or Boc is tert-butyloxycarbonyl; BOC-HYP-OH is BOC protected L-hydroxyproline; DCC is dicyclohexylcarbodiimide; DIPEA is N,N-Diisopropylethylamine; DMAP is dimethylaminopyridine; DME is dimethoxyethane; DMF is dimethylformamide; DMSO is dimethyl sulfoxide; EDCI is 1-(3-dimethylaminopropyl)-3-ethylcarbodiimide; ESI is electrospray ionization; EtOAc is ethyl acetate; FABMS is fast atom bombardment mass spectrometry; HATU is O-(7-azabenzotriazol-1-yl)-N,N,N',N'-tetramethyluronium hexafluorophosphate; HOBT is 1-hydroxybenzotriazole; HPLC is high performance liquid chromatography; HRMS is high resolution mass spectrometry; LDA is lithium diisopropylamide; LRMS is low resolution mass spectrometry; MeOH is methanol; NBS is N-bromosuccinimide; NH$_4$OAc is ammonium acetate; Pd(PPh$_3$)$_4$ is tetrakis(triphenylphosphine)palladium(0); Ph is phenyl; PYBROP is bromotripyrrolidinophosphonium hexafluorophosphate; RPLC is reverse-phase liquid chromatography; SEM is β-(trimethylsilyl)ethoxy]methyl; SEMCl is β-(trimethylsilyl)ethoxy]methyl chloride; Tf is trifluormethanesulfonate; TFA is trifluoroacetic acid; THF is tetrahydrofuran; and TLC is thin-layer chromatography.

The Compounds of Formula (I)

The present invention provides Linked Tricyclic Aryl Compounds of Formula (I):

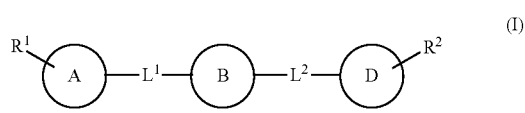

and pharmaceutically acceptable salts thereof, wherein A, B, D, L$^1$, L$^2$, R$^1$ and R$^2$ are defined above for the Compounds of Formula (I).

In one embodiment, A is 5-membered monocyclic heteroarylene.

In another embodiment, A is bicyclic heteroarylene.

In another embodiment, A is a 9-membered bicyclic heteroarylene.

In still another embodiment, A is selected from

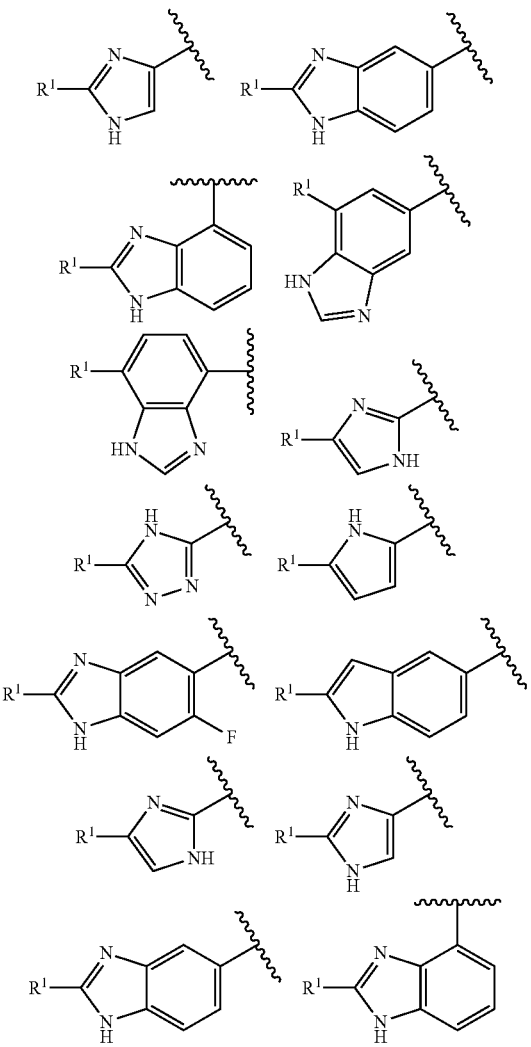

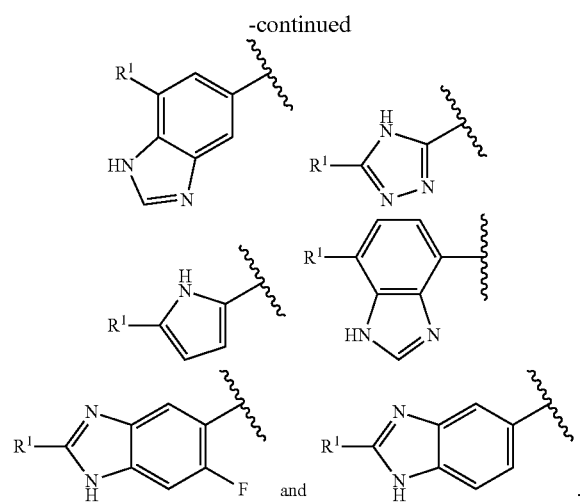

In one embodiment, A is imidazolyl.
In another embodiment, A is benzimidazolyl.
In another embodiment, A is:

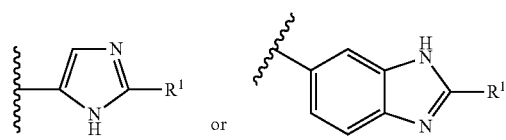

In still another embodiment, A is:

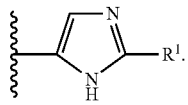

In another embodiment, A is:

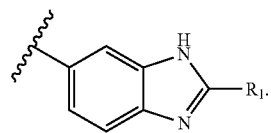

In one embodiment. B is heteroarylene.
In another embodiment, B is 5-membered monocyclic heteroarylene.
In another embodiment, B is arylene.
In another embodiment, B is phenylene.
In a further embodiment, B is naphthylene.
In another embodiment, B is bicyclic heteroarylene.
In still another embodiment, B is selected from the following groups, wherein either one of the two available bonds of each depicted group can be connected to either of the two groups flanking B:

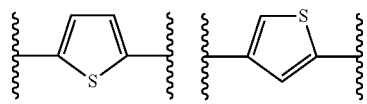

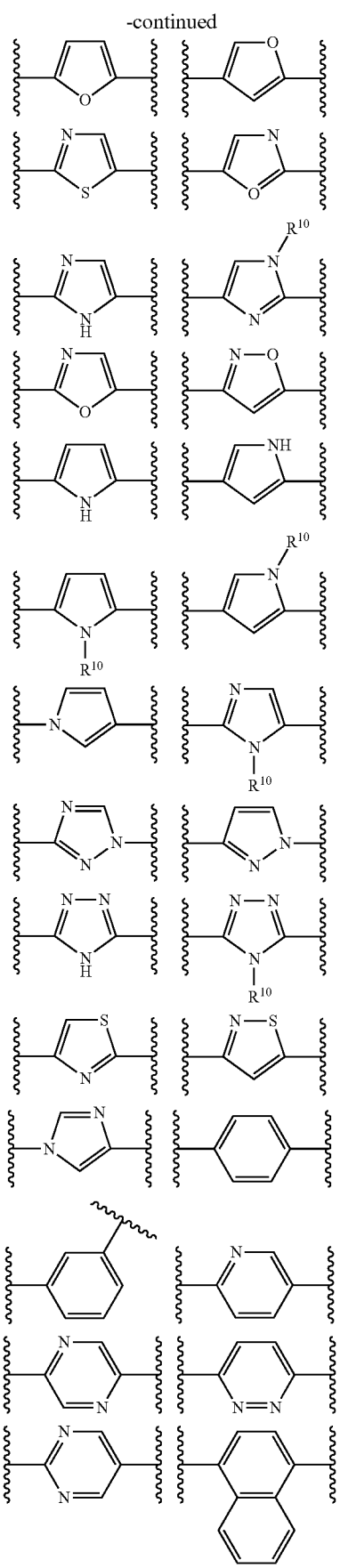

-continued

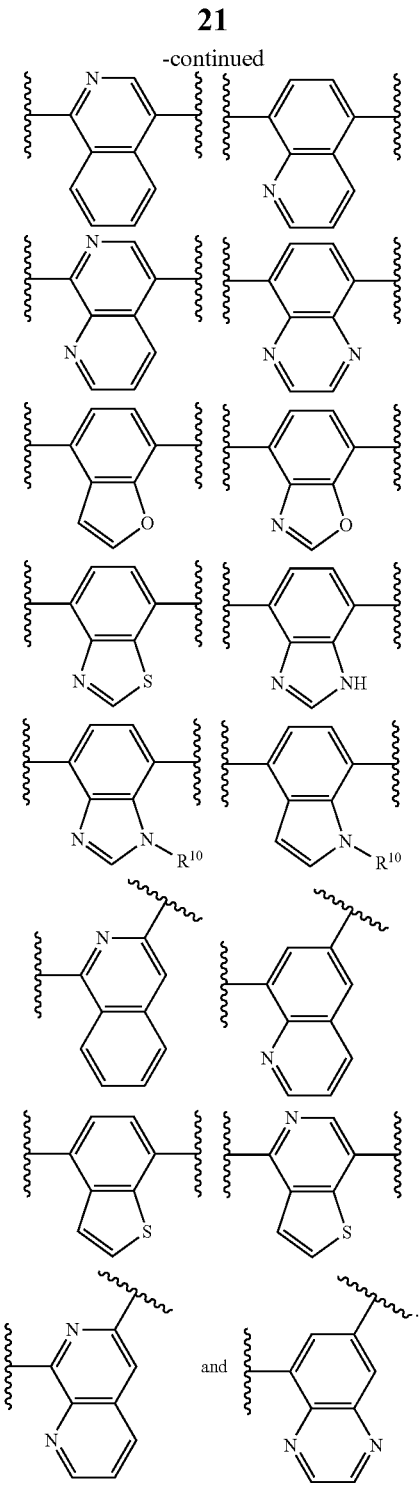

In another embodiment, B is selected from the following groups, wherein either one of the two available bonds of each depicted group can be connected to either of the two groups flanking B:

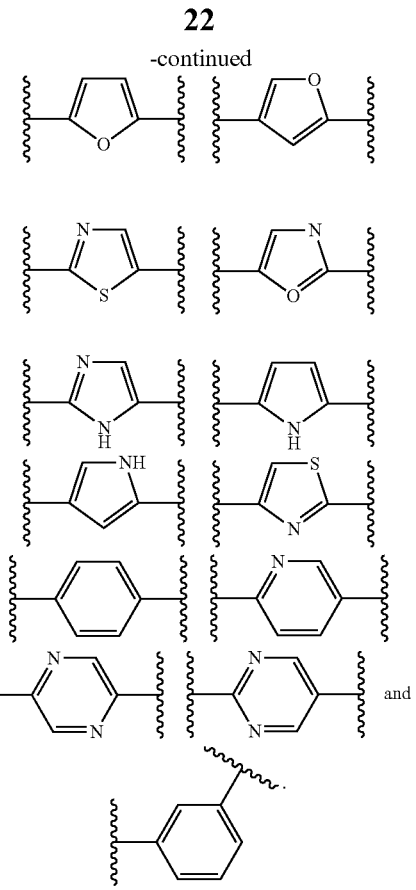

In another embodiment, B is selected from the following groups, wherein either one of the two available bonds of each depicted group can be connected to either of the two groups flanking B:

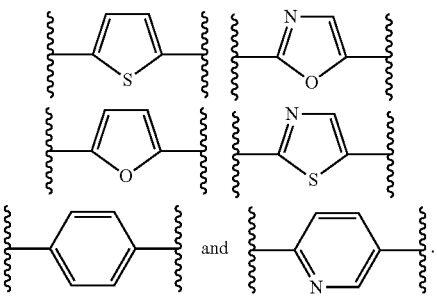

In another embodiment, B is:

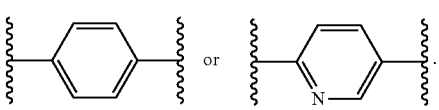

In a further embodiment, B is:

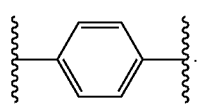

In embodiments wherein B is a multicyclic group (e.g., naphthylene, isoquinolinylene, benzocycloheptenylene, etc. . . . ) the $L^1$ and $L^2$ groups are each bonded to a common ring of B. By way of example, where B is an isoquinolinylene, B includes, for example, the groups represented by the following structures, wherein either of the two illustrated bonds of each group are connected to $L^1$ and $L^2$:

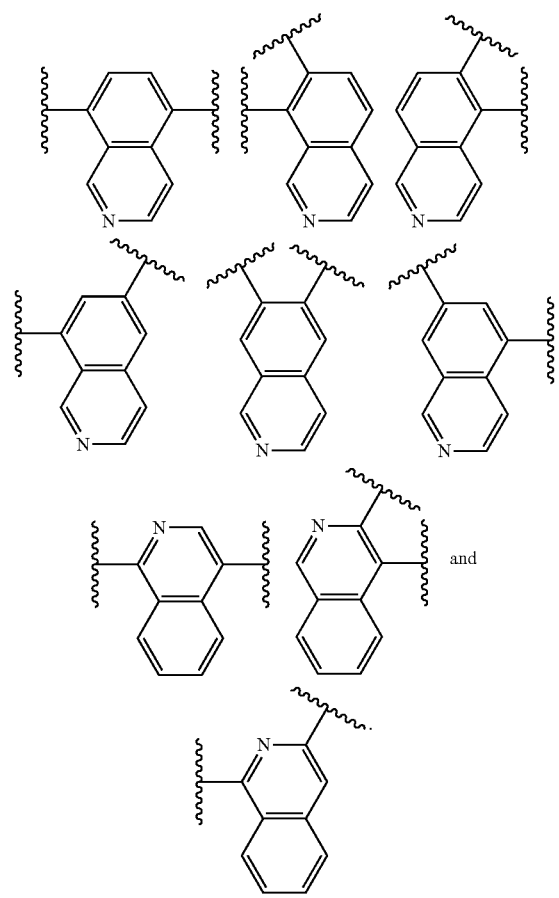

In one embodiment, D is 5-membered monocyclic heteroarylene.

In another embodiment, D is bicyclic heteroarylene.

In another embodiment, D is a 9-membered bicyclic heteroarylene.

In still another embodiment, D is selected from

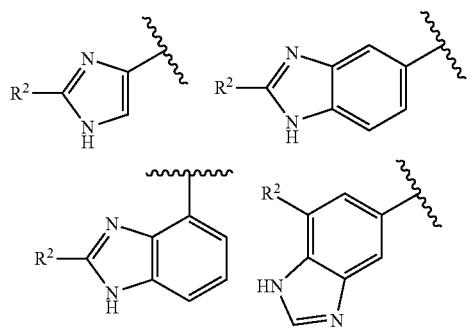

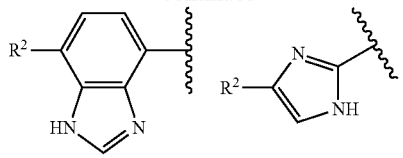

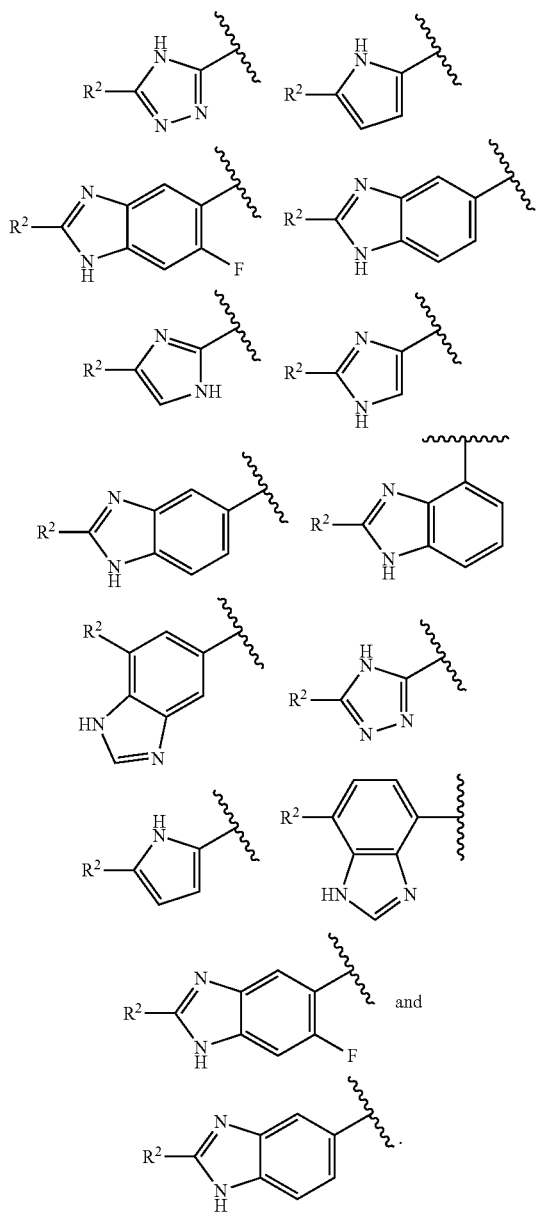

In one embodiment, D is imidazolyl.
In another embodiment, D is benzimidazolyl.
In another embodiment, D is:

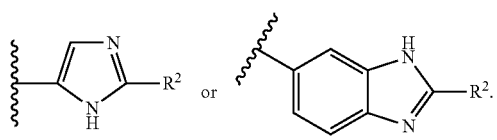

In still another embodiment, D is:

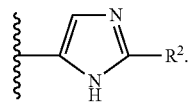

In another embodiment, D is:

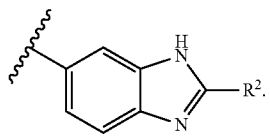

In one embodiment, $L^1$ is —CH$_2$—.
In another embodiment, $L^1$ is —CH$_2$CH$_2$—.
In another embodiment, $L^1$ is —C≡C—.
In another embodiment, $L^1$ is —C≡C—C≡C—.
In still another embodiment, $L^1$ is —CH=CH—.
In another embodiment, $L^1$ is —CH=CH— and the double bond is in the cis configuration.
In another embodiment, $L^1$ is —CH=CH— and the double bond is in the trans configuration.
In a further embodiment, $L^1$ is —C(O)—.
In another embodiment, $L^1$ is —CH$_2$—C(O)—.
In one embodiment, $L^2$ is —CH$_2$—.
In another embodiment, $L^2$ is —C≡C—.
In another embodiment, $L^2$ is —C≡C—C≡C—.
In still another embodiment, $L^2$ is —CH=CH—.
In another embodiment, $L^2$ is —CH=CH— and the double bond is in the cis configuration.
In another embodiment, $L^2$ is —CH=CH— and the double bond is in the trans configuration.
In a further embodiment, $L^2$ is —C(O)—.
In one embodiment, $L^1$ is a bond and $L^2$ is other than a bond.
In another embodiment, $L^1$ is a bond and $L^2$ is —CH$_2$—, —CH=CH—, —CF$_2$— or —C(NR$^{14}$)—.
In one embodiment, $L^2$ is a bond and $L^1$ is other than a bond.
In another embodiment, $L^2$ is a bond and $L^1$ is —CH$_2$—, —CH=CH—, —C(O)—, —CF$_2$— or —C(NR$^{14}$)—.
In another embodiment, neither $L^1$ nor $L^2$ is a bond.
In still another embodiment, $L^1$ is a bond, —CH$_2$—, —CH$_2$—CH$_2$—, —CH$_2$—C(O)—, —NHCH$_2$—, —NH, —C(O)—, —N(CH$_3$)—, —CH=CH— or —C≡C—.
In another embodiment, $L^2$ is a bond, —CH$_2$—, —CH$_2$—CH$_2$—, —C≡C—, —NH, —C(O)— or —N(CH$_3$)—.
In a further embodiment, $L^1$ is a bond, —CH$_2$—, —CH$_2$—CH$_2$—, —CH$_2$—C(O)—, —NHCH$_2$—, —NH, —C(O)—, —N(CH$_3$)—, —CH=CH— or —C≡C—, and $L^2$ is a bond, —CH$_2$—, —CH$_2$—CH$_2$—, —C≡C—, —NH, —C(O)— or —N(CH$_3$)—, such that at least one of $L^1$ and $L^2$ is other than a bond.
In one embodiment $L^1$ and $L^2$ are each independently selected from a bond,

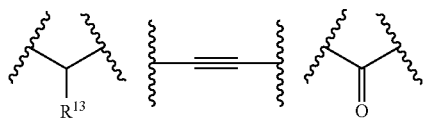

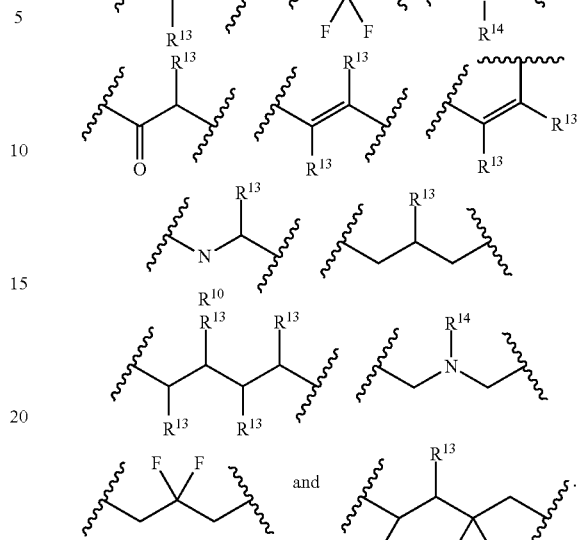

In still another embodiment, $L^1$ and $L^2$ are each independently selected from:

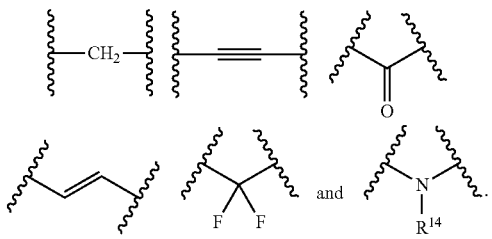

In still another embodiment, $L^1$ and $L^2$ are each independently selected from a bond,

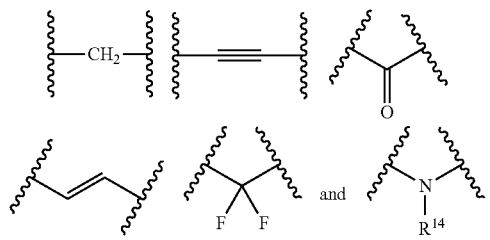

such that at least one of $L^1$ and $L^2$ is other than a bond.

In still another embodiment, one of $L^1$ and $L^2$ is a bond and the other is selected from:

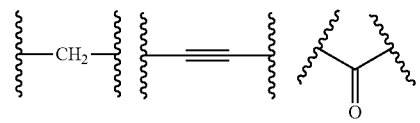

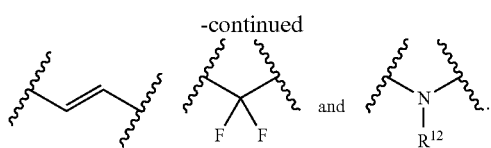

In one embodiment, one of $L^1$ and $L^2$ is a bond and the other of $L^1$ and $L^2$ is selected from:

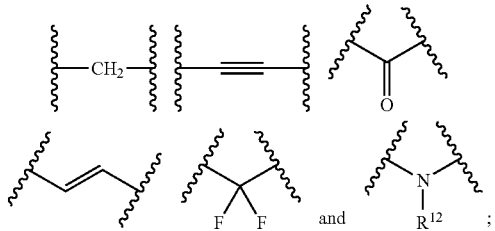

and B is selected from the following groups, wherein either one of the two available bonds of each group can be connected to any adjacent ring:

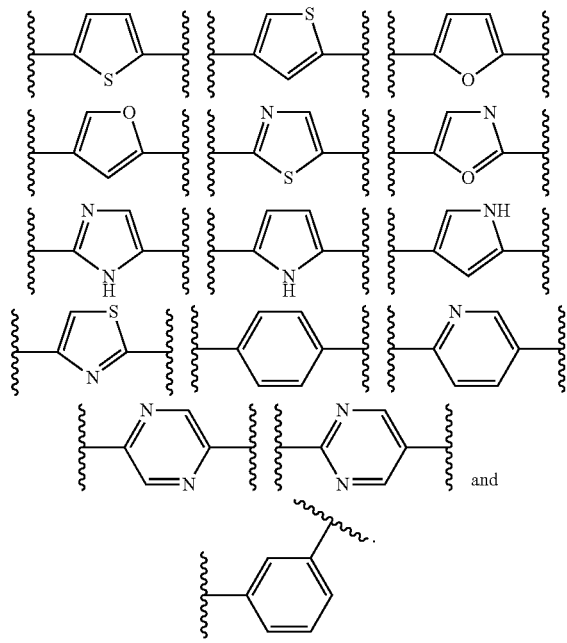

In one embodiment, A and D are each independently 5-membered monocyclic heteroaryl or bicyclic heteroaryl.

In another embodiment, A and D are each independently 5-membered monocyclic heteroaryl or 9-membered bicyclic heteroaryl.

In another embodiment, one of A and D is a 5-membered monocyclic heteroaryl and the other is a 9-membered bicyclic heteroaryl.

In one embodiment, A and D are each independently imidazolyl or benzimidazolyl.

In another embodiment, each of A and D is imidazolyl.

In another embodiment, each of A and D is benzimidazolyl.

In still another embodiment, one of A and D is imidazolyl and the other is benzimidazolyl.

In another embodiment, A and D are each independently selected from

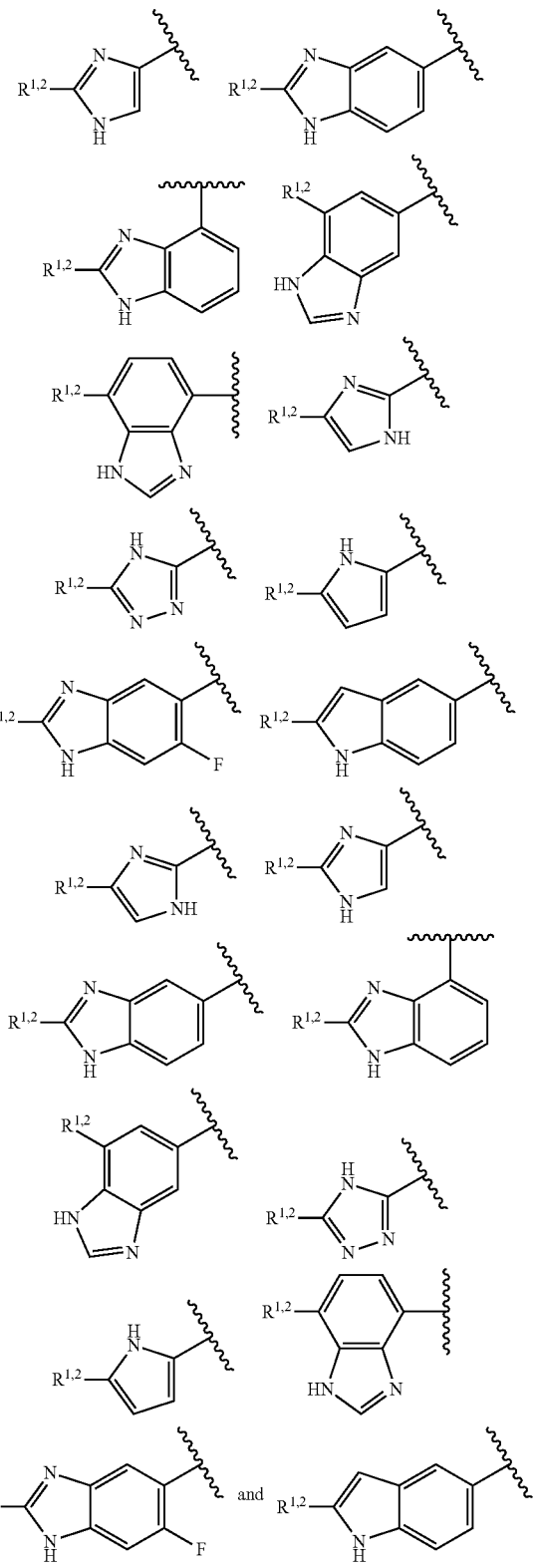

wherein $R^{1,2}$ represents substitution by either an $R^1$ group (attached to A) or an $R^2$ group (attached to D).

In another embodiment, A is:

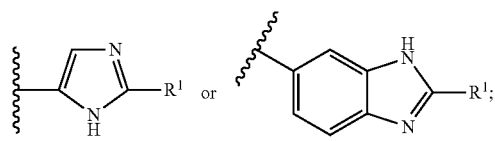

and
D is:

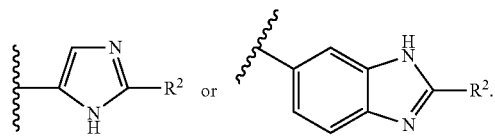

In one embodiment, $R^1$ and $R^2$ are each independently selected from:

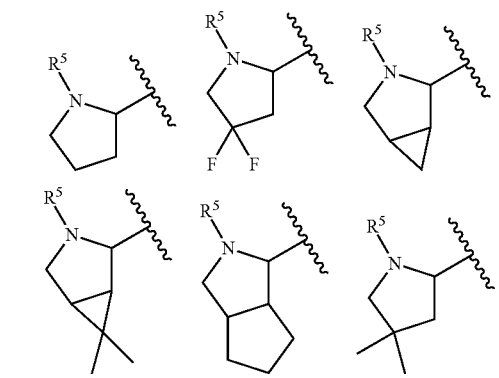

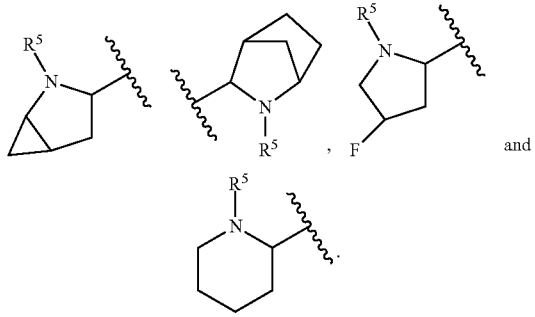

In another embodiment, $R^1$ and $R^2$ are each independently selected from:

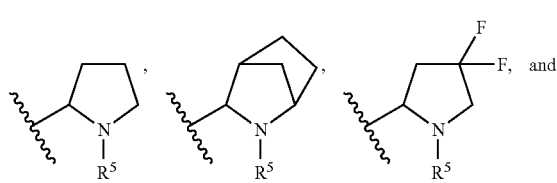

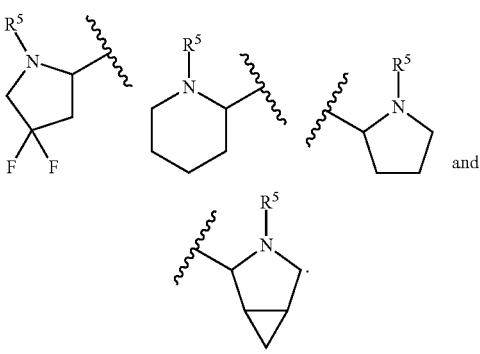

In another embodiment, $R^1$ and $R^2$ are each independently selected from:

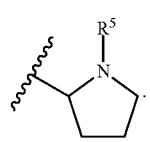

In still another embodiment, $R^1$ and $R^2$ are each

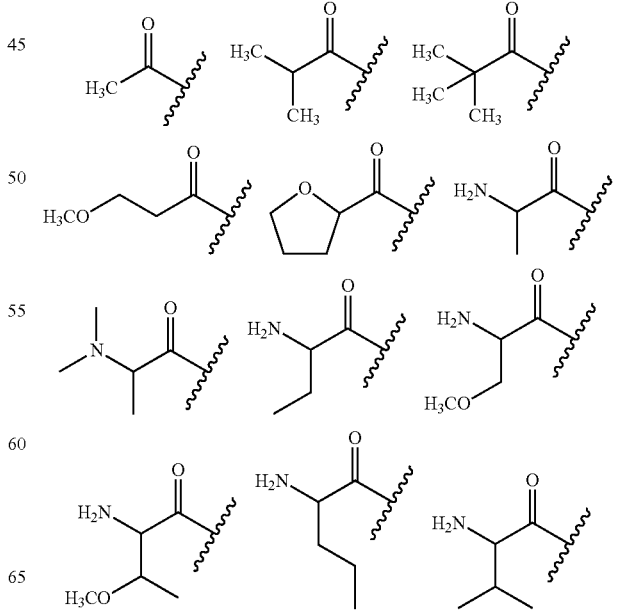

In one embodiment, each occurrence of $R^5$ is independently selected from:

-continued

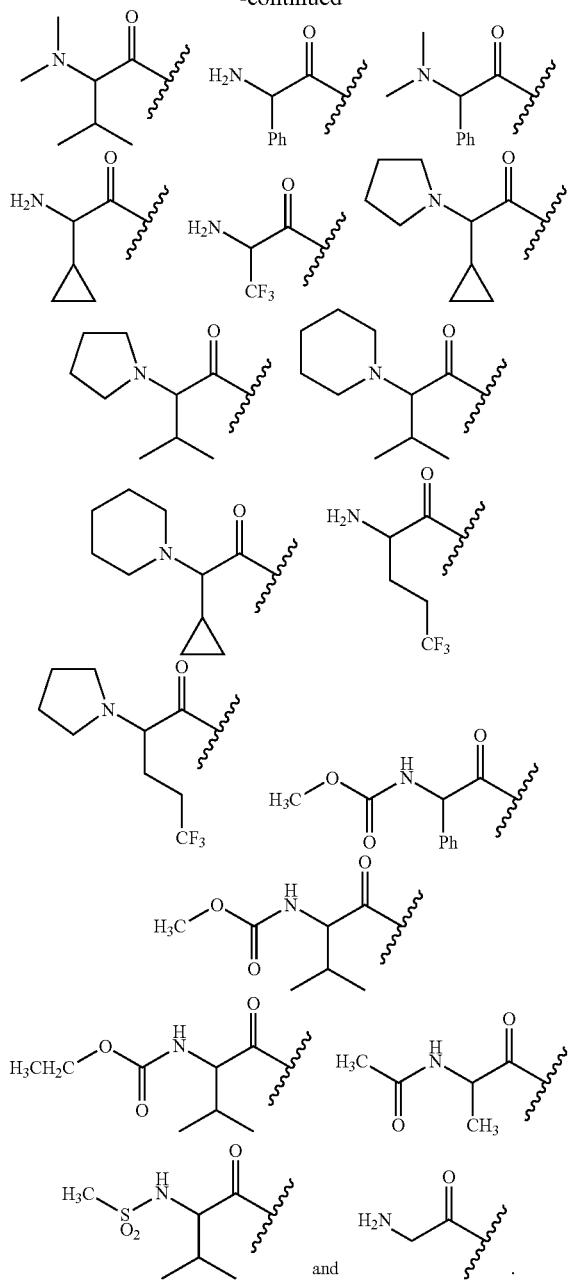

In another embodiment, each occurrence of $R^5$ is independently selected from:

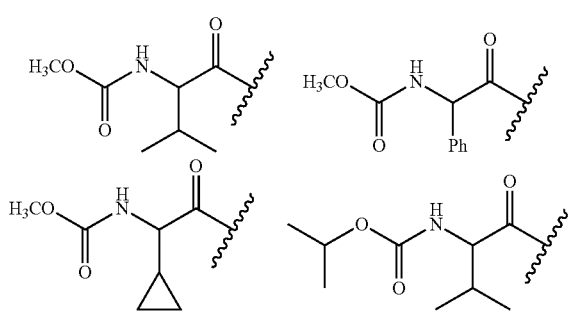

-continued

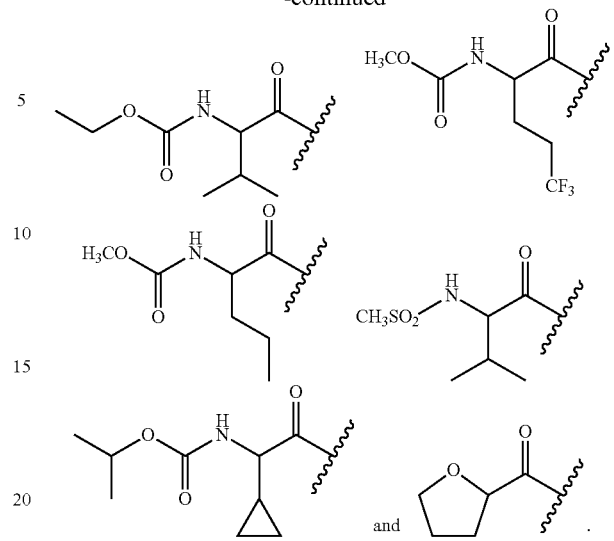

In another embodiment, each occurrence of $R^5$ is independently —C(O)—C($R^{21}$)—NHC(O)O-alkyl, —C(O)—C(alkyl)-NHC(O)N($R^{20}$)$_2$, —C(O)—C($R^{20}$)—N($R^{20}$)$_2$, —C(O)-alkyl, —C(O)O-alkyl or —C(O)—C(alkyl)-NHS(O)$_2$-alkyl, wherein each occurrence of $R^{20}$ is independently H or —$C_1$-$C_4$ alkyl; and each occurrence of $R^{21}$ is independently phenyl or —$C_1$-$C_4$ alkyl.

In another embodiment, each occurrence of $R^5$ is independently:

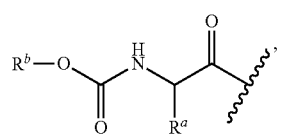

wherein $R^a$ is H, alkyl, haloalkyl, cycloalkyl or aryl, and $R^b$ is alkyl.

In another embodiment, each occurrence of $R^5$ is independently:

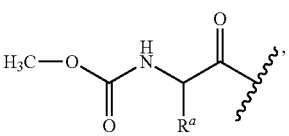

wherein $R^a$ is H, methyl, ethyl, propyl, isopropyl, t-butyl, cyclopropyl, —CH$_2$CH$_2$CF$_3$ or phenyl.

In another embodiment, each occurrence of $R^5$ is independently:

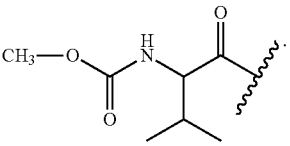 [SMILES: *C(=O)C(NC(=O)OC)C(C)C]

In one embodiment, A is
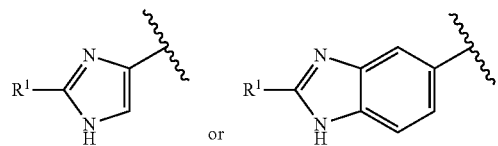
and D is
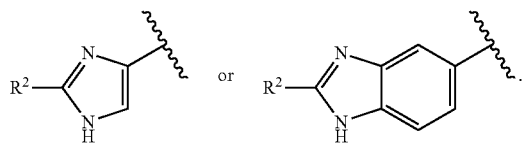
and each occurrence of $R^5$ is
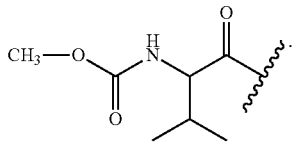 [SMILES: *C(=O)C(NC(=O)OC)C(C)C]
In one embodiment, $R^1$ and $R^2$ are each independently selected from:
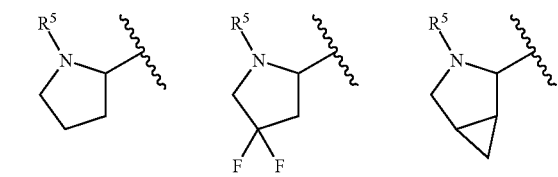
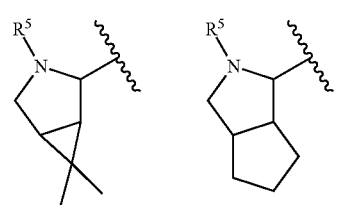
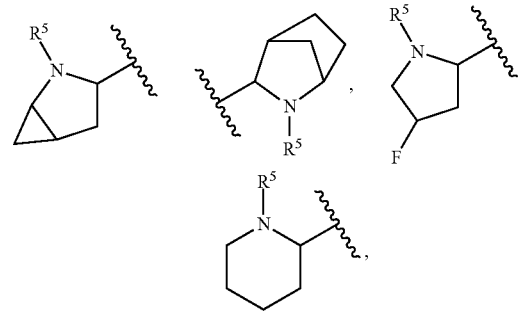
and each occurrence of $R^5$ is independently selected from:
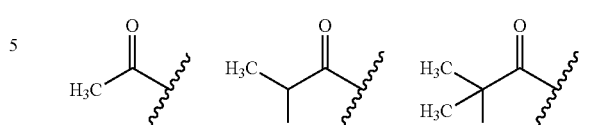
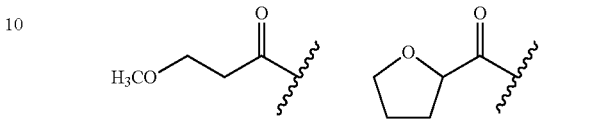
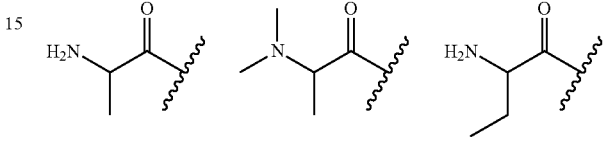
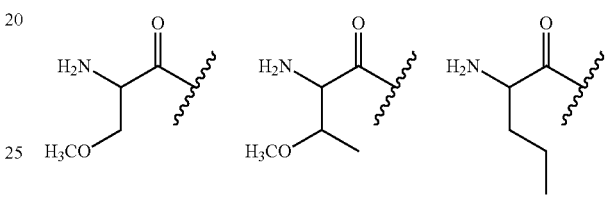
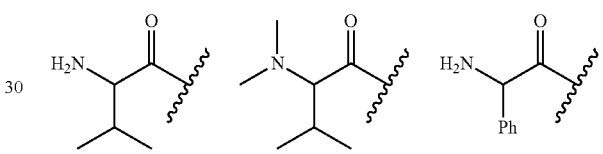
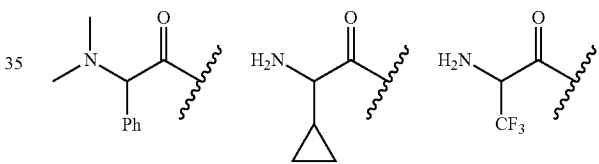
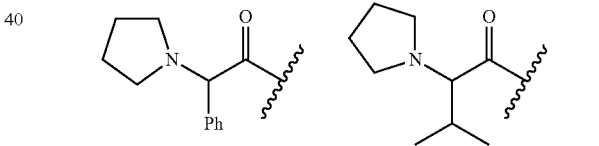
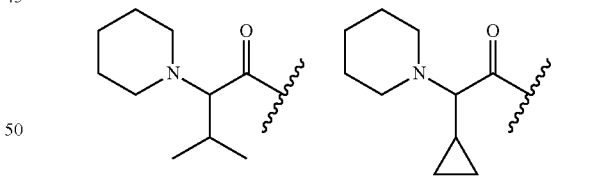
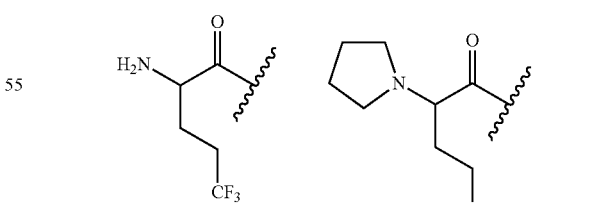
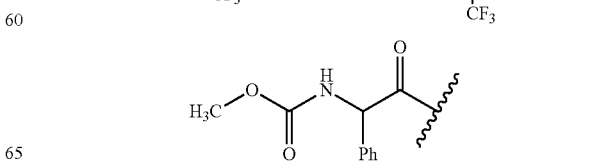

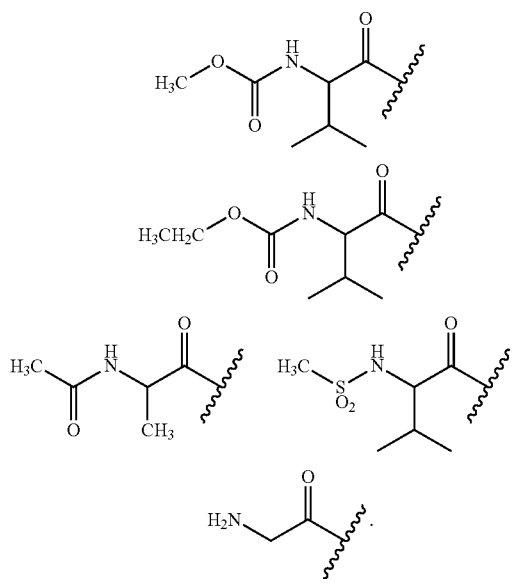
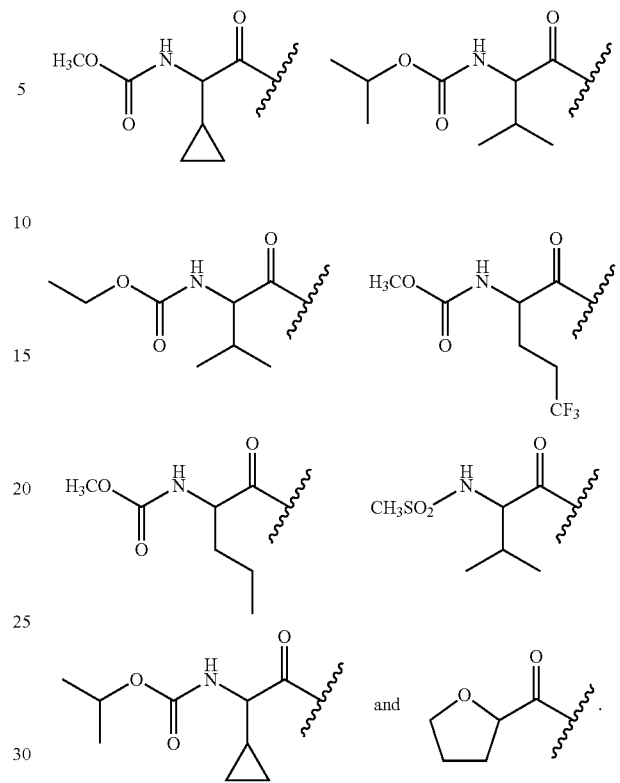
In another embodiment, $R^1$ and $R^2$ are each independently selected from:
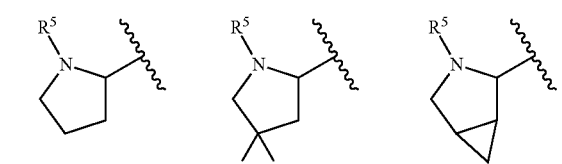
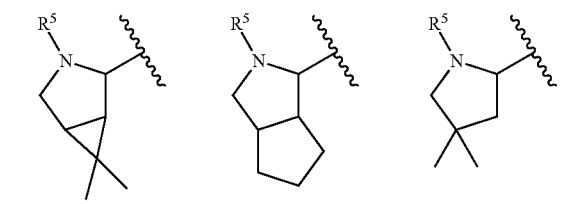
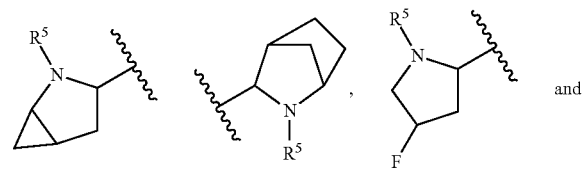
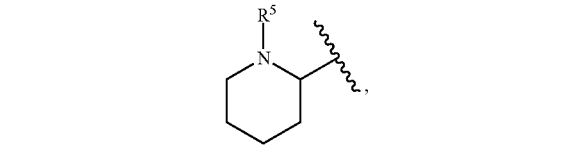
and each occurrence of $R^5$ is independently selected from:
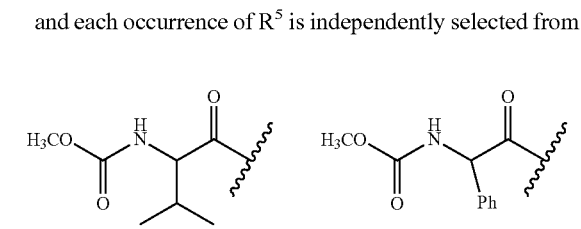
In another embodiment, $R^1$ and $R^2$ are each independently selected from:
and each occurrence of $R^5$ is independently selected from:
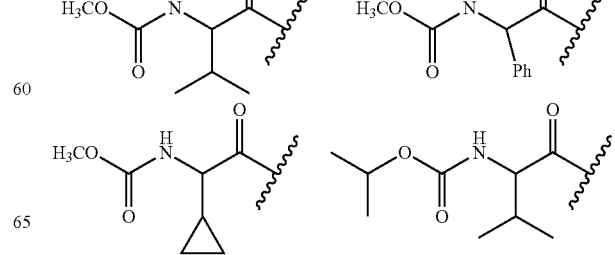

-continued

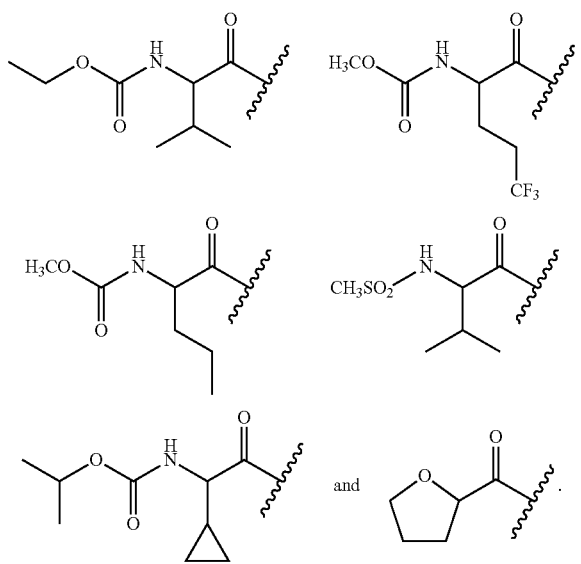

In still another embodiment, $R^1$ and $R^2$ are each independently selected from:

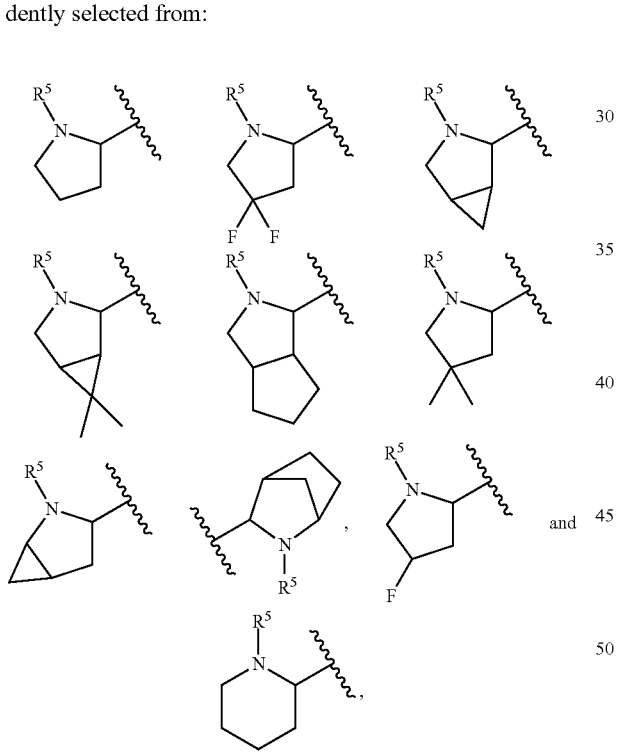

and each occurrence of $R^5$ is independently:

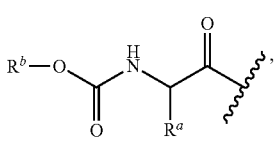

wherein $R^a$ is H, alkyl, haloalkyl, cycloalkyl or aryl, and $R^b$ is alkyl.

In another embodiment, $R^1$ and $R^2$ are each:

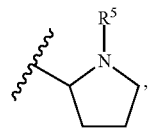

and each occurrence of $R^5$ is:

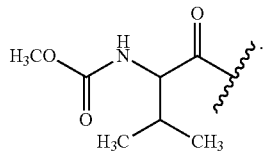 [SMILES: *C(=O)C(NC(=O)OC)C(C)C]

In one embodiment, A-$R^1$ and D-$R^2$ are each independently selected from:

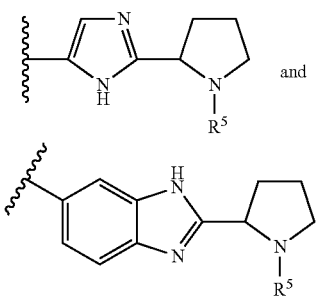

In another embodiment, A-$R^1$ and D-$R^2$ are each:

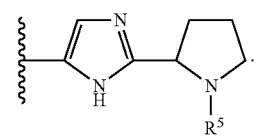

In another embodiment, A-$R^1$ and D-$R^2$ are each:

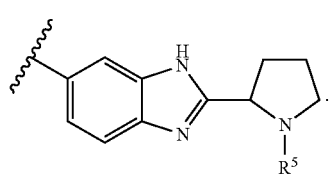

In still another embodiment, one of A-$R^1$ and D-$R^2$ is:

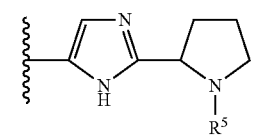

and the other of A-R$^1$ and D-R$^2$ is:

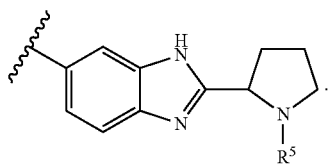

In one embodiment, A-R$^1$ and D-R$^2$ are each independently selected from

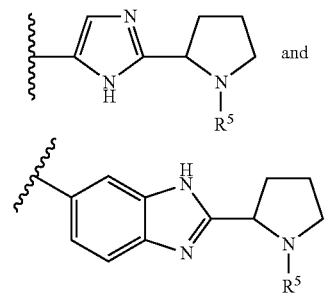

and each occurrence of R$^5$ is independently

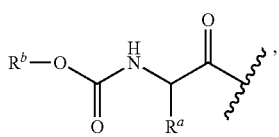

wherein R$^a$ is H, alkyl, haloalkyl, cycloalkyl or aryl, and R$^b$ is alkyl.

In another embodiment, A-R$^1$ and D-R$^2$ are each independently selected from

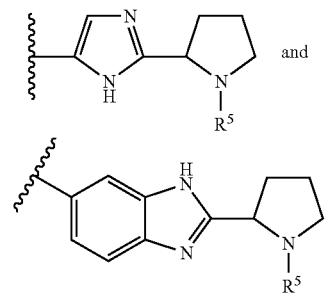

and each occurrence of R$^5$ is independently

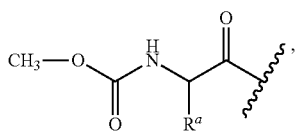

wherein R$^a$ is H, methyl, ethyl, propyl, isopropyl, t-butyl, cyclopropyl, —CH$_2$CH$_2$CF$_3$ or phenyl.

In another embodiment, A-R$^1$ and D-R$^2$ are each independently selected from

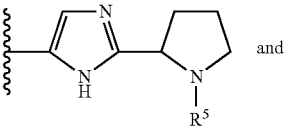

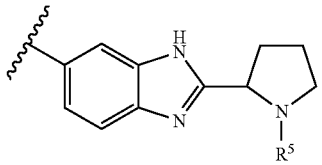

and each occurrence of R$^5$ is independently

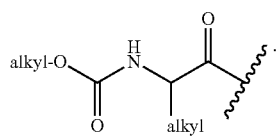

In one embodiment, A-R$^1$ and D-R$^2$ are each independently selected from

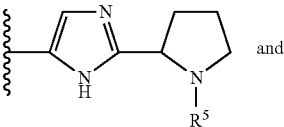

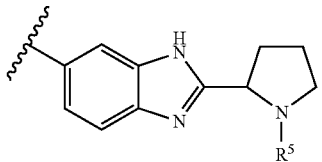

and each occurrence of R$^5$ is

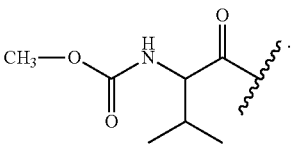

In one embodiment, A-R$^1$ and D-R$^2$ are each

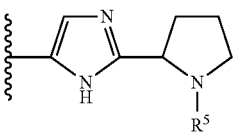

and each occurrence of R$^5$ is

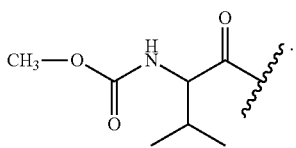 [SMILES: *C(=O)C(NC(=O)OC)C(C)C]
In another embodiment, A-R$^1$ and D-R$^2$ are each
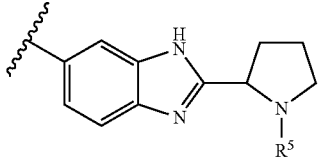
and each occurrence of R$^5$ is
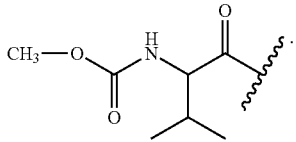 [SMILES: *C(=O)C(NC(=O)OC)C(C)C]
In one embodiment, A-R$^1$ and D-R$^2$ are each independently selected from
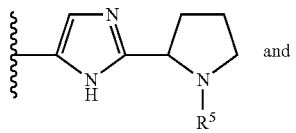
and
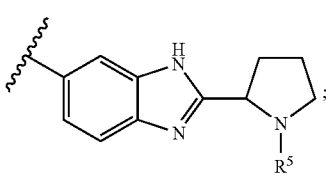
each occurrence of R$^5$ is independently selected from:
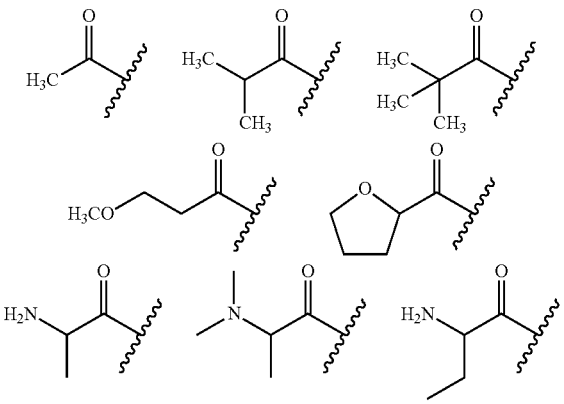
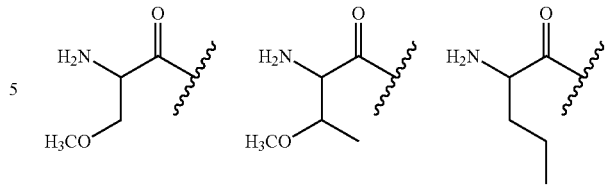
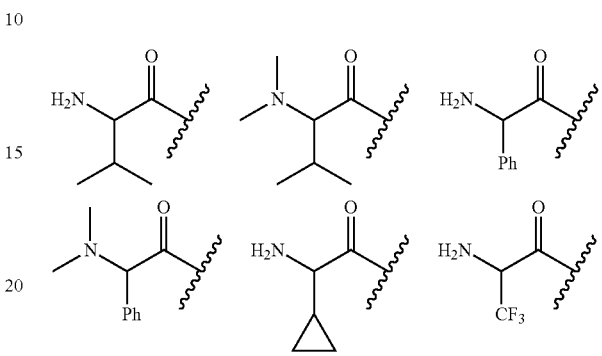
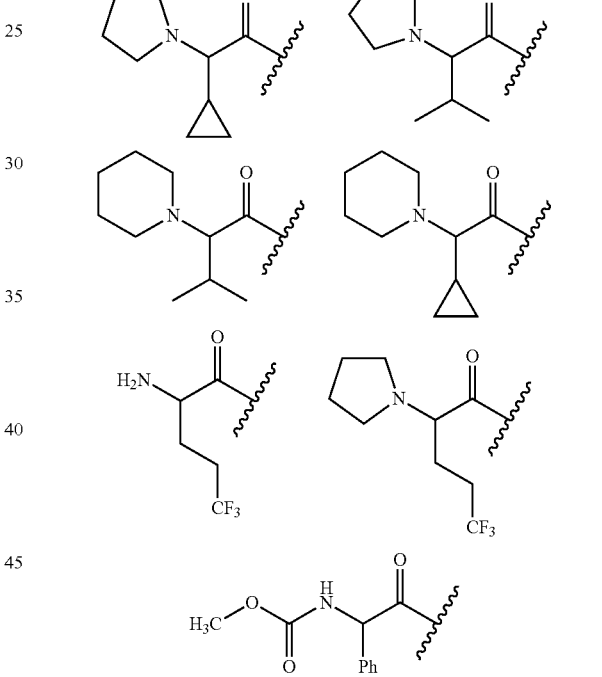
and

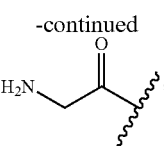

B is selected from the following groups, wherein either one of the two available bonds of each depicted group can be connected to either of the two groups flanking B:

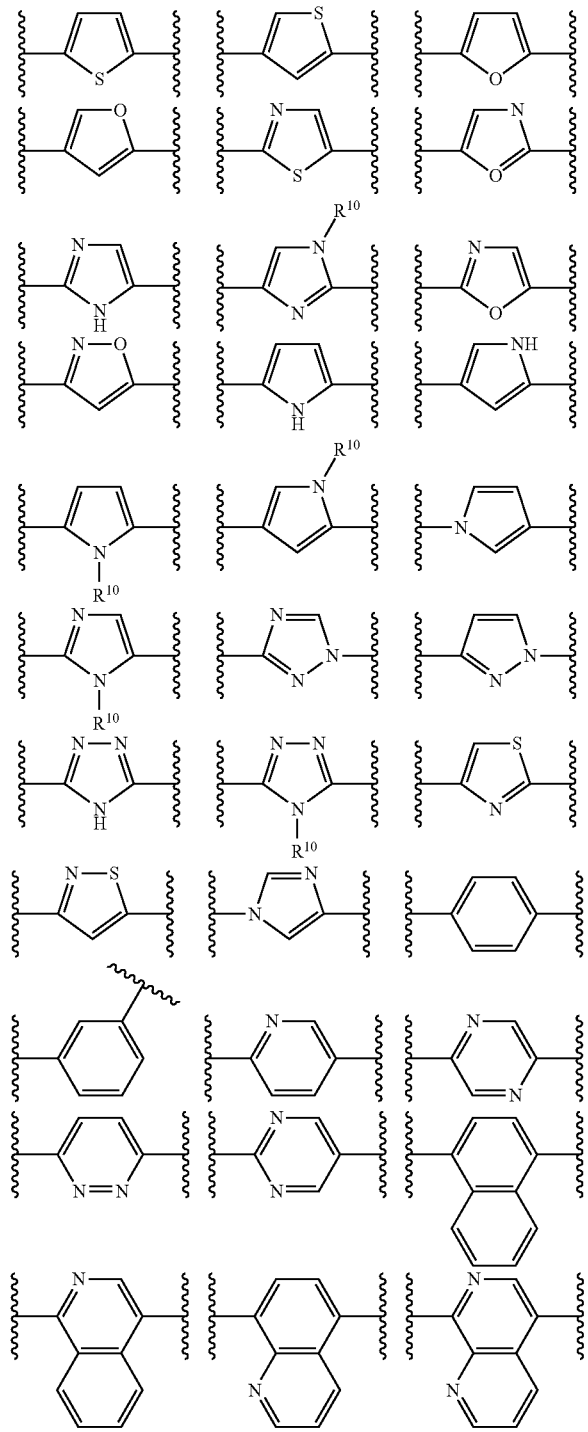

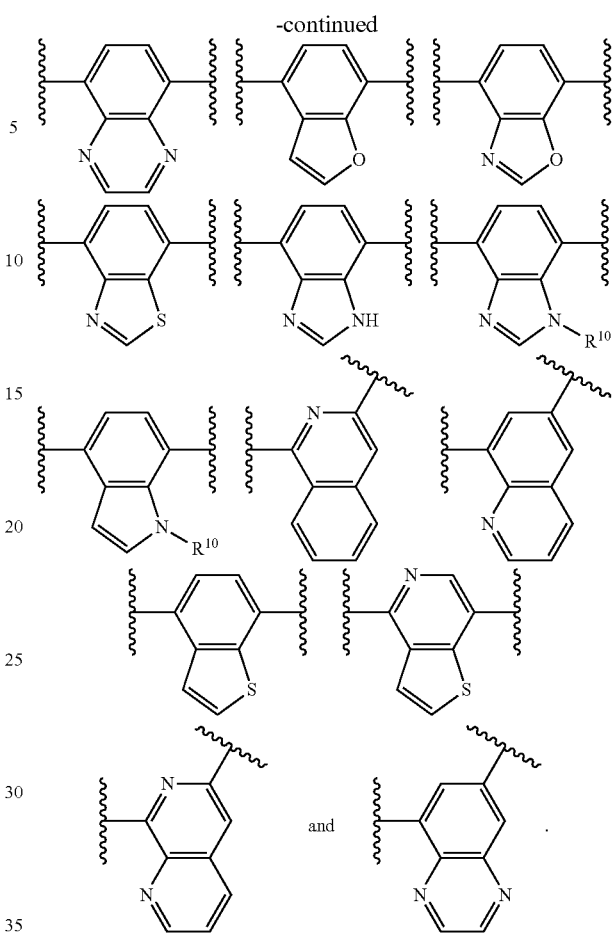

In another embodiment, A-R$^1$ and D-R$^2$ are each independently selected from

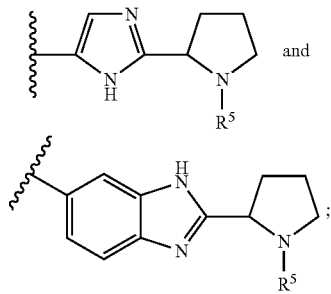

each occurrence of R$^5$ is independently selected from:

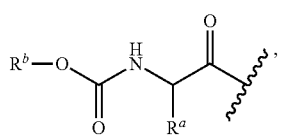

wherein R$^a$ is H, alkyl, haloalkyl, cycloalkyl or aryl, and R$^b$ is alkyl; and B is selected from the following groups, wherein either one of the two available bonds of each depicted group can be connected to either of the two groups flanking B:

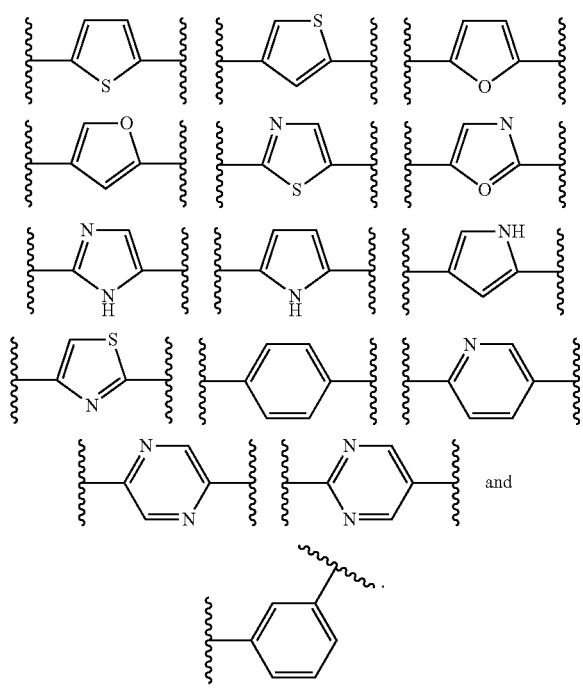

In another embodiment, A-R$^1$ and D-R$^2$ are each independently selected from

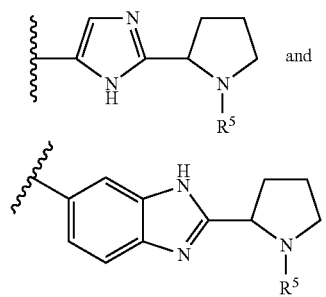

each occurrence of R$^5$ is independently selected from:

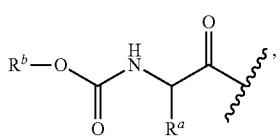

wherein R$^a$ is H, alkyl, haloalkyl, cycloalkyl or aryl, and R$^b$ is alkyl;

B is selected from the following groups, wherein either one of the two available bonds of each depicted group can be connected to either of the two groups flanking B:

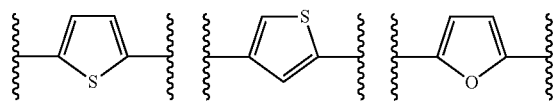

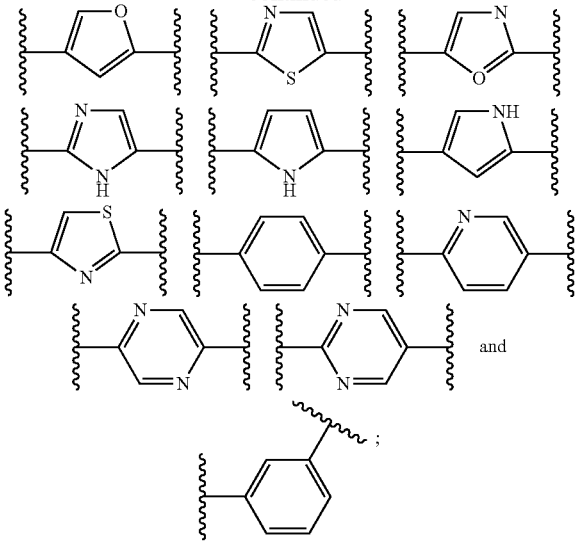

and

L$^2$ are each independently selected from:

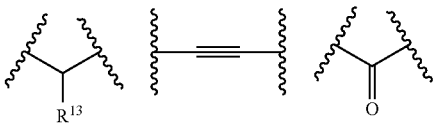

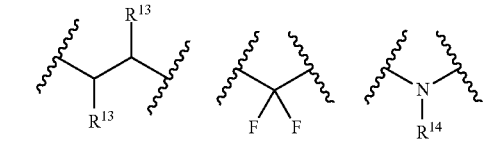

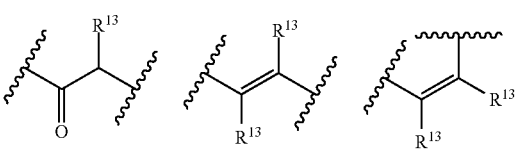

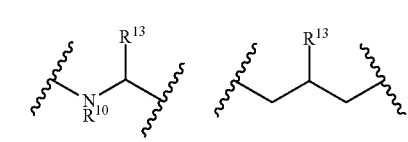

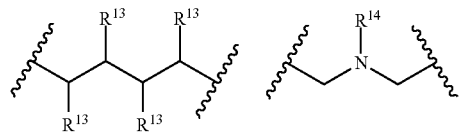

In one embodiment, A is:

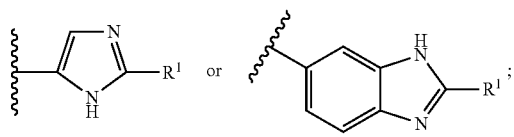

D is:

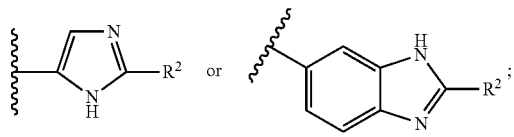

and
B is selected from the following groups, wherein either one of the two available bonds of each depicted group can be connected to either of the two groups flanking B:

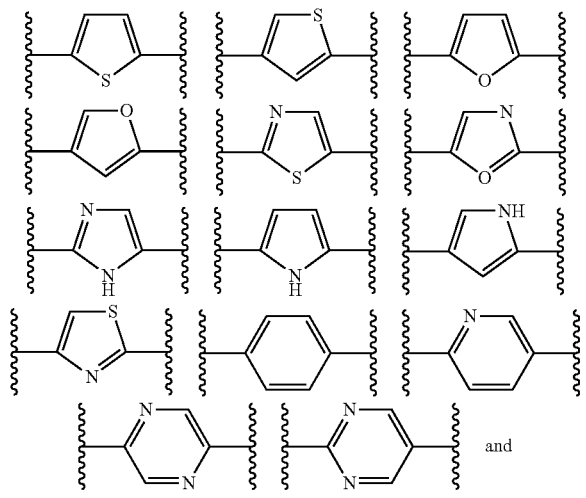

In another embodiment, A-$R^1$ and D-$R^2$ are each independently selected from

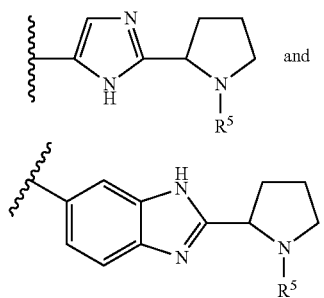

B is selected from the following groups, wherein either one of the two available bonds of each depicted group can be connected to either of the two groups flanking B:

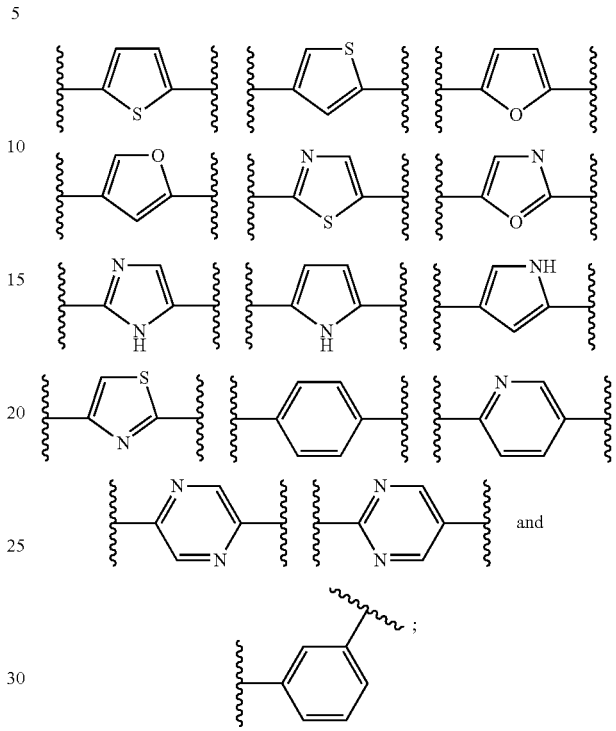

$L^1$ is a bond, —$CH_2$—, —$CH_2$—$CH_2$—, —$CH_2$—C(O)—, —$NHCH_2$—, —NH, —C(O)—, —N($CH_3$)—, —CH=CH— or —C≡C—, and $L^2$ is a bond, —$CH_2$—, —$CH_2$—$CH_2$—, —C≡C—, —NH, —C(O)— or —N($CH_3$)—, such that at least one of $L^1$ and $L^2$ is other than a bond; and each occurrence of $R^5$ is independently selected from:

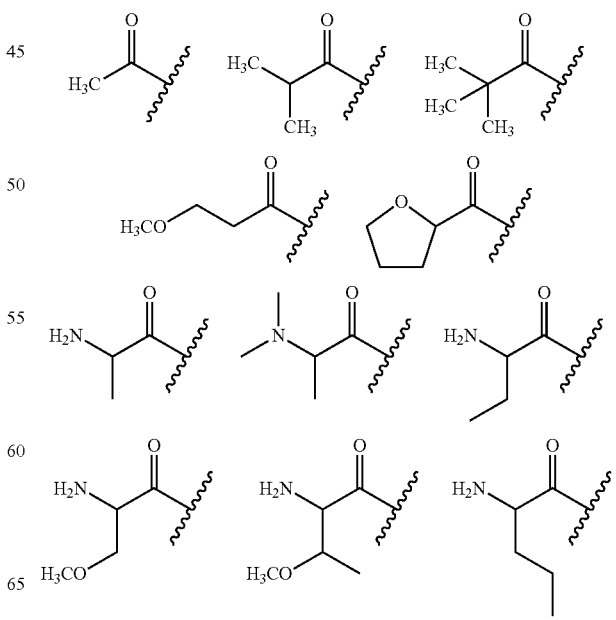

-continued

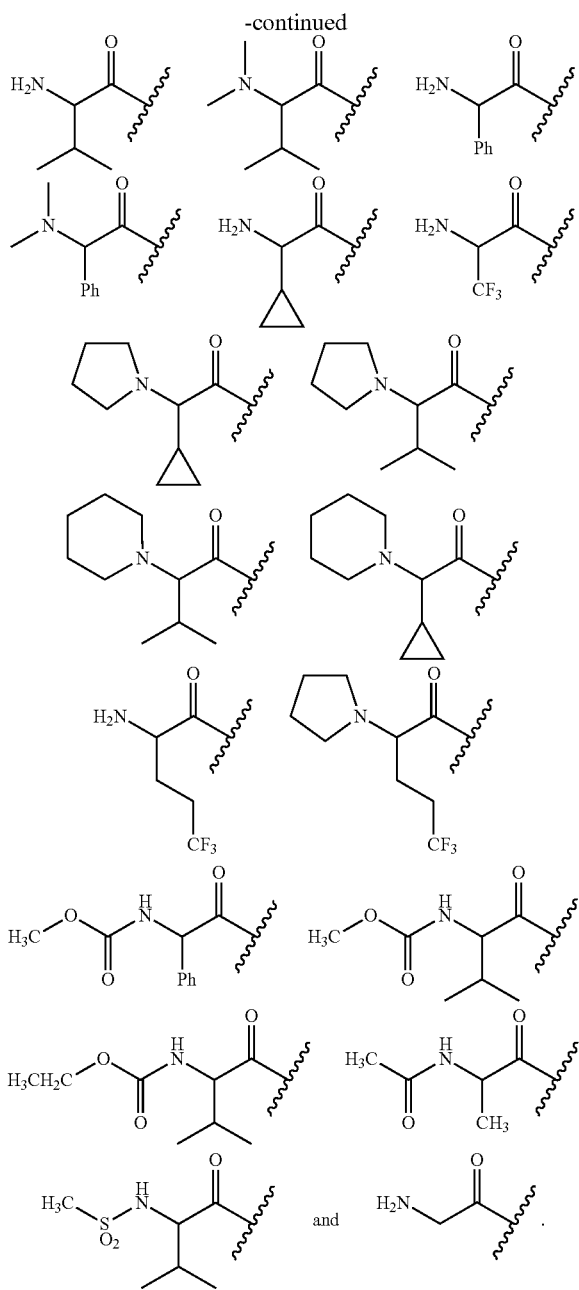

In another embodiment, A-R$^1$ and D-R$^2$ are each independently selected from

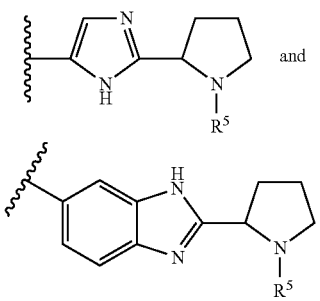

B is selected from the following groups, wherein either one of the two available bonds of each depicted group can be connected to either of the two groups flanking B:

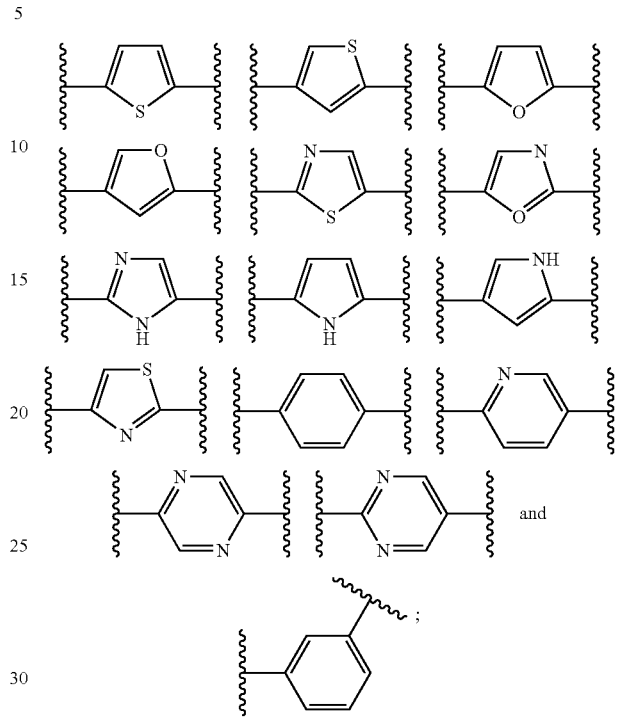

L$^1$ is a bond, —CH$_2$—, —CH$_2$—CH$_2$—, —CH$_2$—C(O)—, —NHCH$_2$—, —NH, —C(O)—, —N(CH$_3$)—, —CH═CH— or —C≡C—, and L$^2$ is a bond, —CH$_2$—, —CH$_2$—CH$_2$—, —C≡C—, —NH, —C(O)— or —N(CH$_3$)—, such that at least one of L$^1$ and L$^2$ is other than a bond; and each occurrence of R$^5$ is:

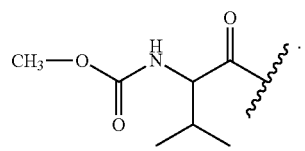 [SMILES: *C(=O)C(NC(=O)OC)C(C)C]

In one embodiment, one or more hydrogen atoms of a Compound of Formula (I) is replaced with a deuterium atom.

In another embodiment, for the Compounds of Formula (I), variables A, B, D, L$^1$, L$^2$, R$^1$ and R$^2$ are selected independently from each other.

In another embodiment, a Compound of Formula (I) is in substantially purified form.

In one embodiment, the Compounds of Formula (I) have the Formula (Ia):

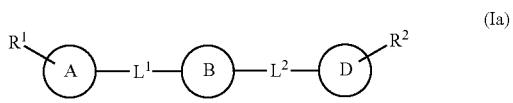

(Ia)

and pharmaceutically acceptable salts thereof, wherein:

A is

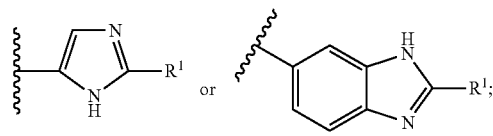

B is selected from:

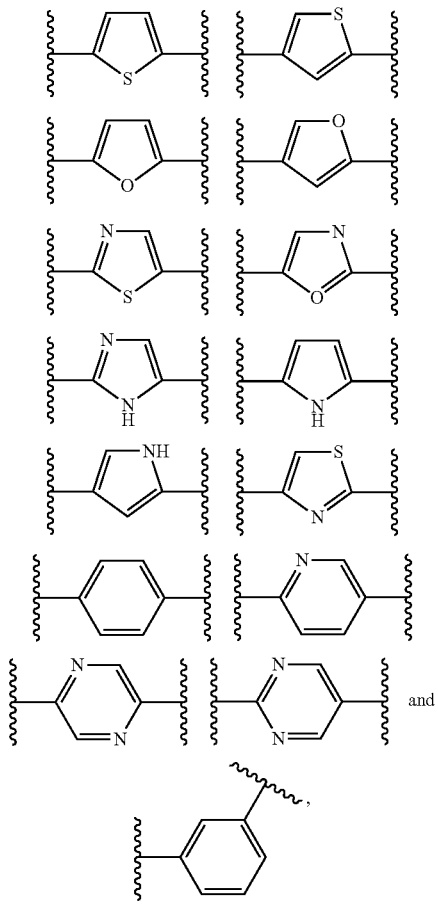

wherein either one of the two available bonds of each depicted group can be connected to either of the two groups flanking B;

D is:

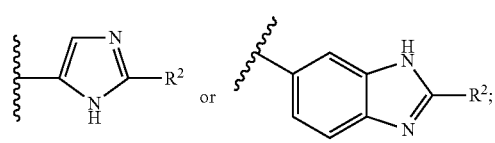

L¹ is a bond, —CH₂—, —CH₂—CH₂—, —CH₂—C(O)—, —NHCH₂—, —NH, —C(O)—, —N(CH₃)—, —CH=CH— or —C≡C—;

L² is a bond, —CH₂—, —CH₂—CH₂—, —C≡C—, —NH, —C(O)— or —N(CH₃)—, such that at least one of L¹ and L² is other than a bond;

R¹ is:

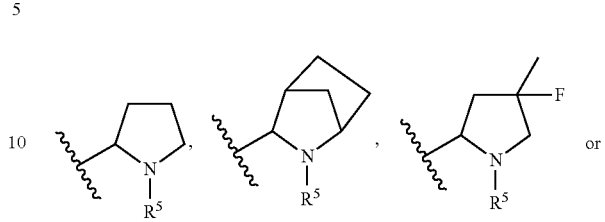

R² is:

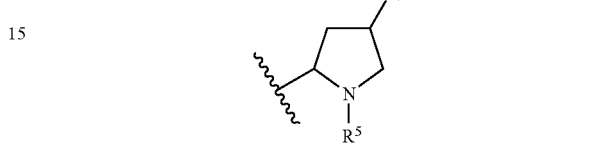

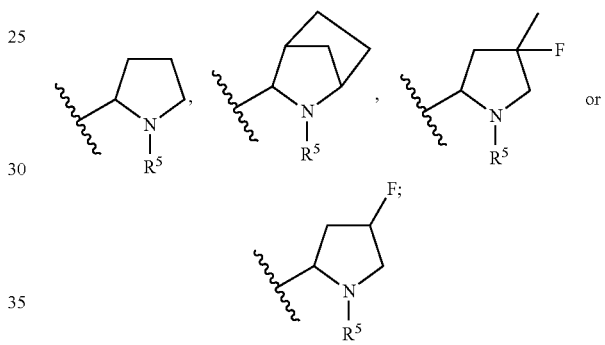

each occurrence of $R^5$ is independently —C(O)—C($R^{21}$)—NHC(O)O-alkyl, —C(O)—) C(alkyl)-NHC(O)N($R^{20}$)₂, —C(O)—C($R^{20}$)—N($R^{20}$)₂, —C(O)-alkyl, —C(O)O-alkyl or —C(O)—C(alkyl)-NHS(O)₂-alkyl;

each occurrence of $R^{20}$ is independently H or —$C_1$-$C_4$ alkyl; and each occurrence of $R^{21}$ is independently phenyl or —$C_1$-$C_4$ alkyl.

In one embodiment, for the Compounds of Formula (Ia), A is:

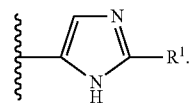

In another embodiment, for the Compounds of Formula (Ia), A is:

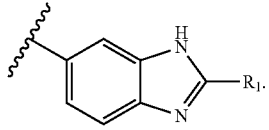

In one embodiment, for the Compounds of Formula (Ia), B is:

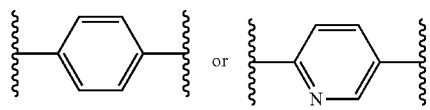

In another embodiment, for the Compounds of Formula (Ia), B is:

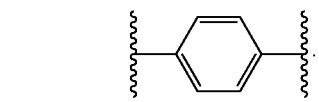

In one embodiment, for the Compounds of Formula (Ia), D is:

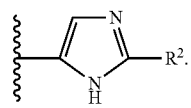

In another embodiment, for the Compounds of Formula (Ia), D is:

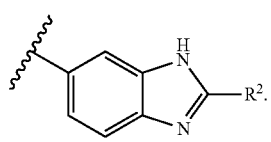

In one embodiment, for the Compounds of Formula (Ia), $L^1$ is a bond and $L^2$ is other than a bond.

In another embodiment, for the Compounds of Formula (Ia), $L^1$ is a bond and $L^2$ is —CH$_2$—, —CH$_2$—CH$_2$—, —C≡C—, —NH, —C(O)— or —N(CH$_3$)—.

In one embodiment, for the Compounds of Formula (Ia), $L^2$ is a bond and $L^1$ is other than a bond.

In another embodiment, for the Compounds of Formula (Ia), $L^2$ is a bond and $L^1$ is —CH$_2$—, —CH$_2$—CH$_2$—, —CH$_2$—C(O)—, —NHCH$_2$—, —NH, —C(O)—, —N(CH$_3$)—, —CH=CH— or —C≡C—.

In another embodiment, for the Compounds of Formula (Ia), neither of $L^1$ and $L^2$ is a bond.

In one embodiment, for the Compounds of Formula (Ia), one, but not both, of $R^1$ and $R^2$ is

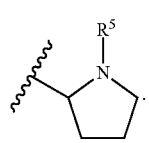

In another embodiment, for the Compounds of Formula (Ia), each of $R^1$ and $R^2$ is

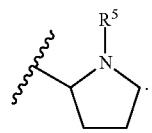

In one embodiment, for the Compounds of Formula (Ia), each occurrence of $R^5$ is independently selected from:

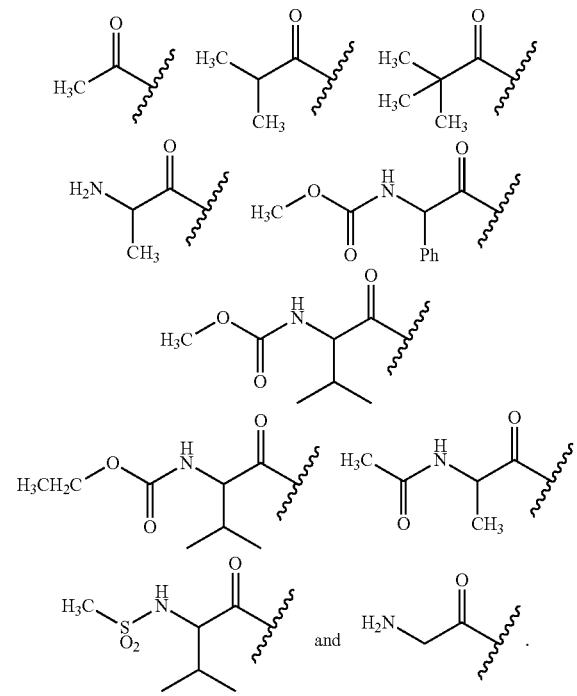

In another embodiment, for the Compounds of Formula (Ia), each occurrence of $R^5$ is independently:

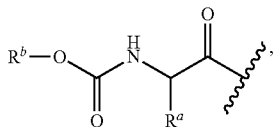

wherein $R^a$ is H, alkyl, haloalkyl, cycloalkyl or aryl, and $R^b$ is alkyl.

In another embodiment, for the Compounds of Formula (Ia), each occurrence of $R^5$ is:

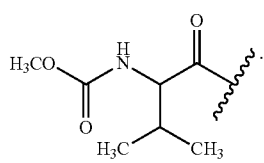 [SMILES: *C(=O)C(NC(=O)OC)C(C)C]

In one embodiment, for the Compounds of Formula (Ia), A-R¹ and D-R² are each independently selected from

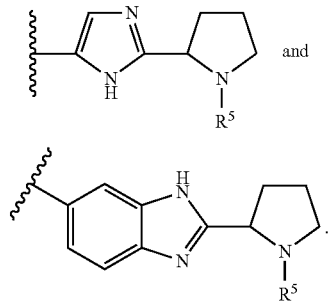 and

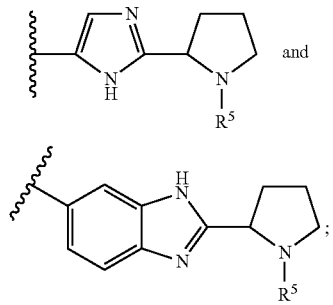

In another embodiment, for the Compounds of Formula (Ia), A-R¹ and D-R² are each independently selected from

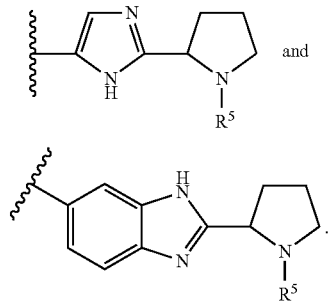 and

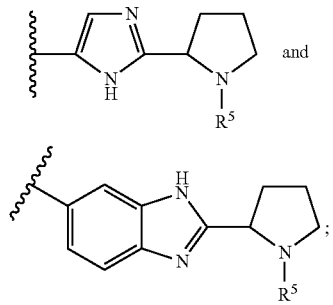;

and each occurrence of $R^5$ is independently selected from:

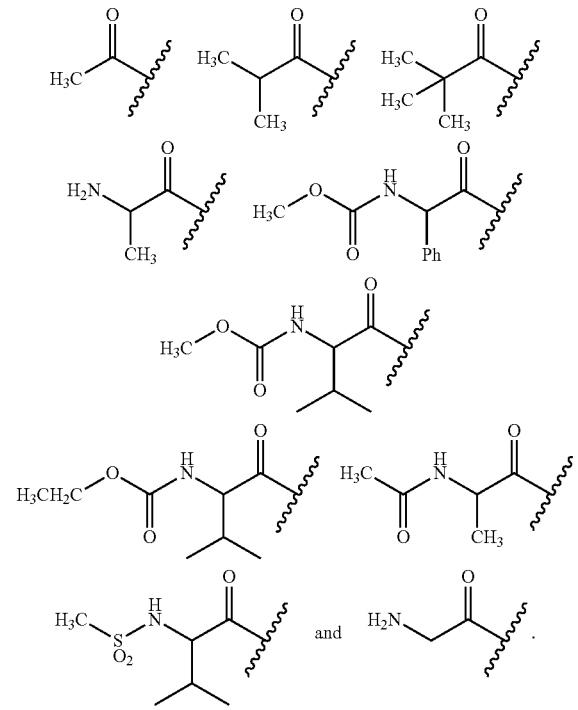

In another embodiment, for the Compounds of Formula (Ia), each occurrence of $R^5$ is independently:

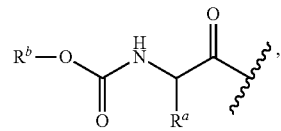, wherein $R^a$ is H, alkyl, haloalkyl, cycloalkyl or aryl, and $R^b$ is alkyl.

In another embodiment, for the Compounds of Formula (Ia), each occurrence of $R^5$ is independently

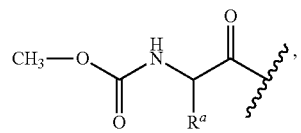, wherein $R^a$ is H, methyl, ethyl, propyl, isopropyl, t-butyl, cyclopropyl, —CH₂CH₂CF₃ or phenyl.

In a further embodiment, for the Compounds of Formula (Ia), each occurrence of $R^5$ is:

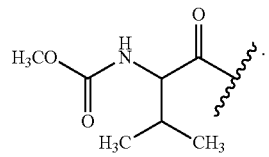.

In another embodiment, for the Compounds of Formula (Ia), A-R¹ and D-R² are each independently selected from

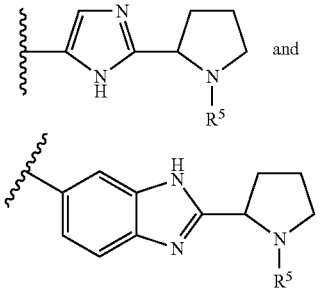

and each occurrence of $R^5$ is independently

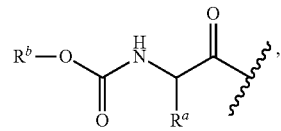, wherein $R^a$ is H, alkyl, haloalkyl, cycloalkyl or aryl, and $R^b$ is alkyl.

In another embodiment, for the Compounds of Formula (Ia), A-R¹ and D-R² are each independently selected from

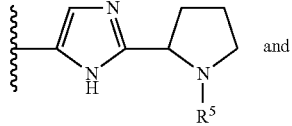

and

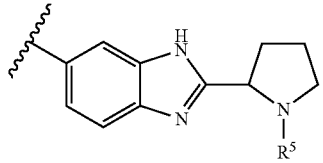

and each occurrence of R⁵ is independently

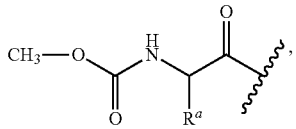

wherein Rᵃ is H, methyl, ethyl, propyl, isopropyl, t-butyl, cyclopropyl, —CH₂CH₂CF₃ or phenyl.

In another embodiment, for the Compounds of Formula (Ia), A-R¹ and D-R² are each independently selected from

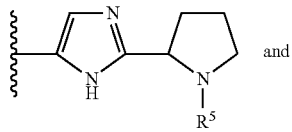

and

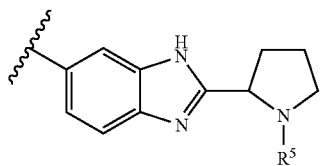

and each occurrence of R⁵ is independently

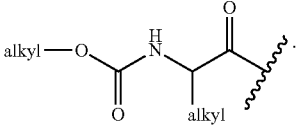

In one embodiment, for the Compounds of Formula (Ia), A-R¹ and D-R² are each independently selected from

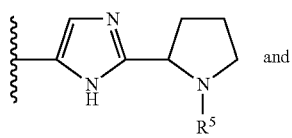

and

-continued

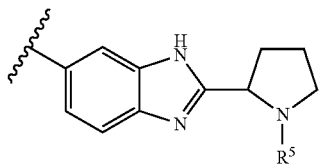

and each occurrence of R⁵ is

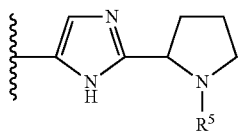

In one embodiment, for the Compounds of Formula (Ia), A-R¹ and D-R² are each

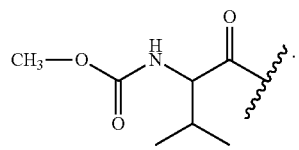 [SMILES: *C(=O)C(NC(=O)OC)C(C)C]

and each occurrence of R⁵ is

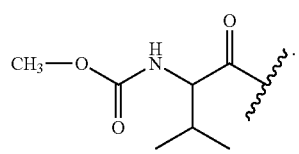 [SMILES: *C(=O)C(NC(=O)OC)C(C)C]

In one embodiment, for the Compounds of Formula (Ia), A-R¹ and D-R² are each

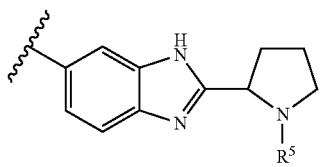

and each occurrence of R⁵ is

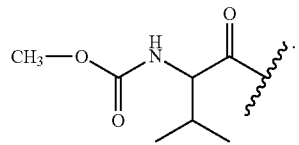 [SMILES: *C(=O)C(NC(=O)OC)C(C)C]

In another embodiment, for the Compounds of Formula (Ia), A-R¹ and D-R² are each independently selected from

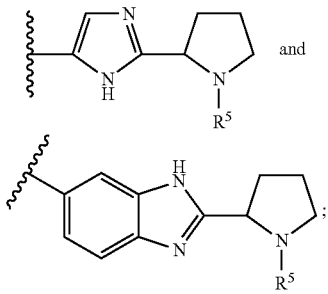

B is:

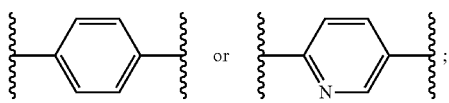

and each occurrence of R⁵ is independently selected from:

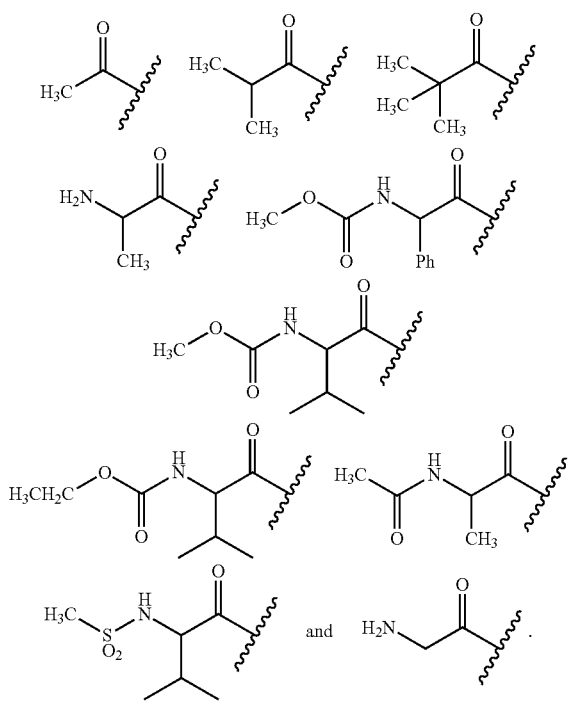

Other embodiments of the present invention include the following:
(a) A pharmaceutical composition comprising an effective amount of a Compound of Formula (I) and a pharmaceutically acceptable carrier.
(b) The pharmaceutical composition of (a), further comprising a second therapeutic agent selected from the group consisting of HCV antiviral agents, immunomodulators, and anti-infective agents.
(c) The pharmaceutical composition of (b), wherein the HCV antiviral agent is an antiviral selected from the group consisting of HCV protease inhibitors and HCV NS5B polymerase inhibitors.
(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV NS5A, or for treating HCV infection and/or reducing the likelihood or severity of symptoms of HCV infection.
(e) The combination of (d), wherein the HCV antiviral agent is an antiviral selected from the group consisting of HCV protease inhibitors and HCV NS5B polymerase inhibitors.
(f) A method of inhibiting HCV NS5A in a subject in need thereof which comprises administering to the subject an effective amount of a Compound of Formula (I).
(g) A method of treating HCV infection and/or reducing the likelihood or severity of symptoms of HCV infection in a subject in need thereof which comprises administering to the subject an effective amount of a Compound of Formula (I).
(h) The method of (g), wherein the Compound of Formula (I) is administered in combination with an effective amount of at least one second therapeutic agent selected from the group consisting of HCV antiviral agents, immunomodulators, and anti-infective agents.
(i) The method of (h), wherein the HCV antiviral agent is an antiviral selected from the group consisting of HCV protease inhibitors and HCV NS5B polymerase inhibitors.
(j) A method of inhibiting HCV NS5A in a subject in need thereof which comprises administering to the subject the pharmaceutical composition of (a), (b), or (c) or the combination of (d) or (e).
(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

The present invention also includes a compound of the present invention for use (i) in, (ii) as a medicament for, or (iii) in the preparation of a medicament for: (a) inhibiting HCV NS5A, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 1-58 as set forth below:

7
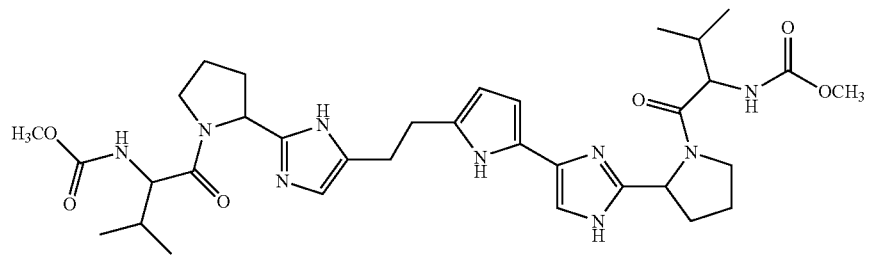
8
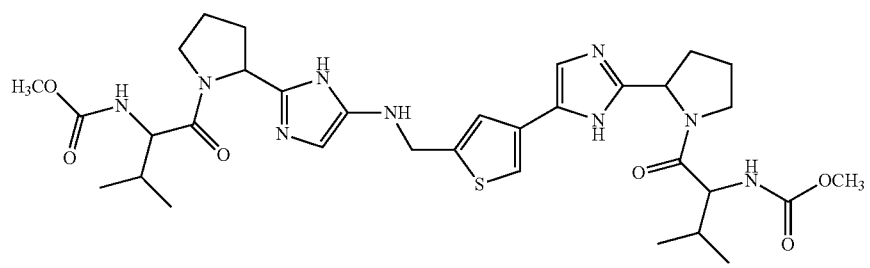
9
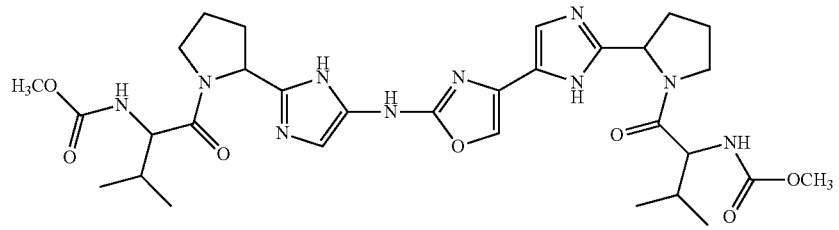
10
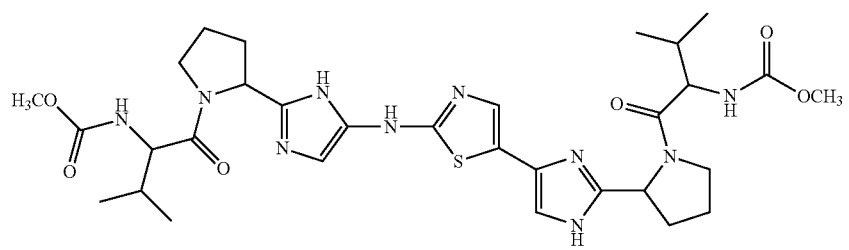
11
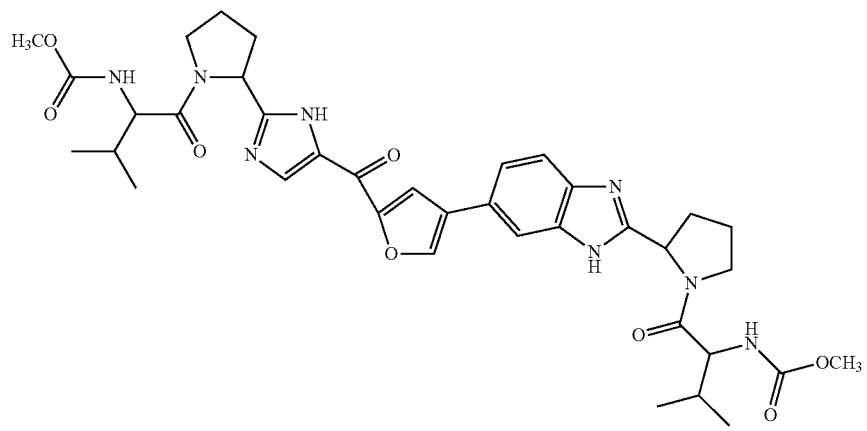

12
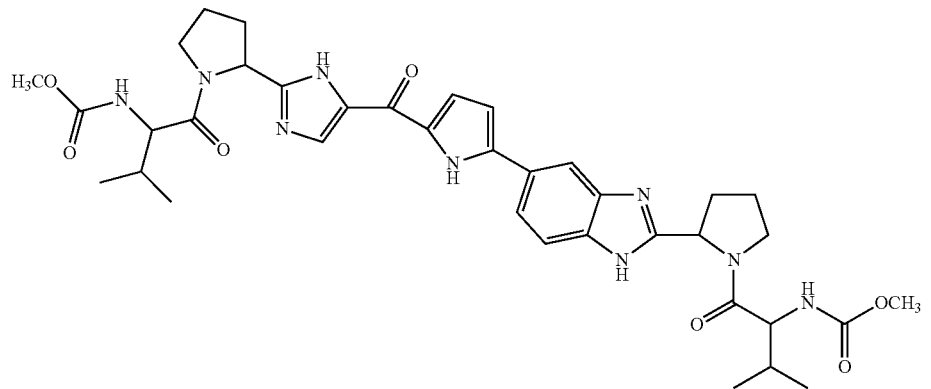
13
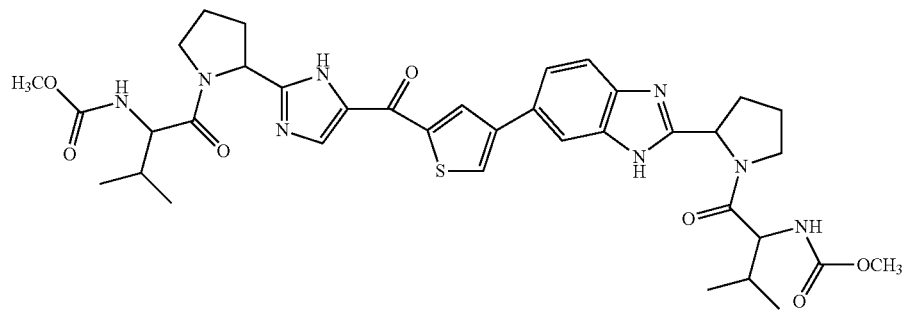
14
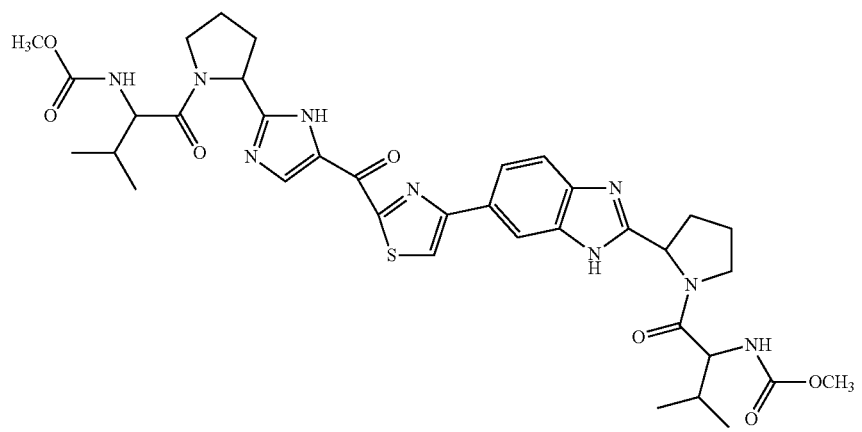
15
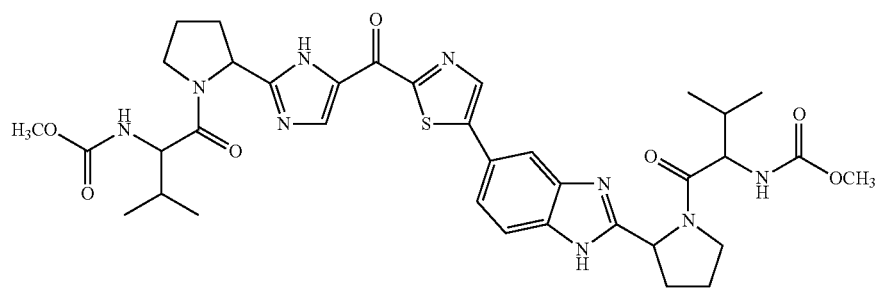

16
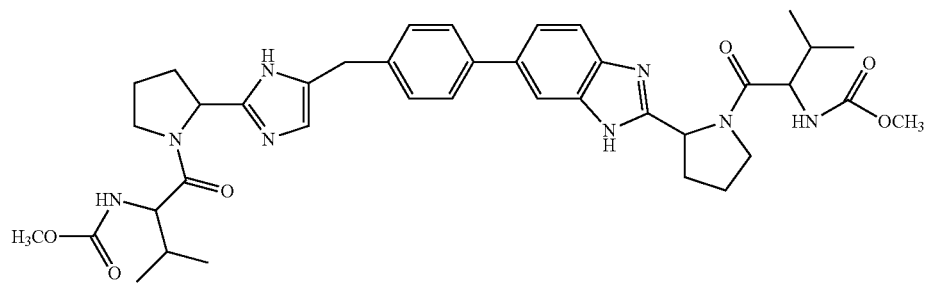
17
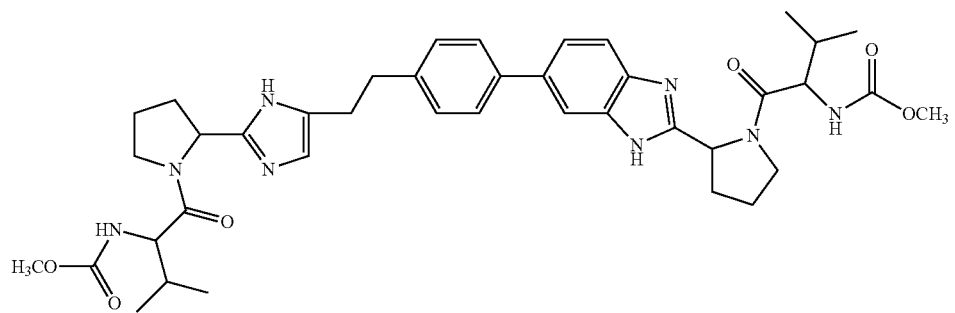
18
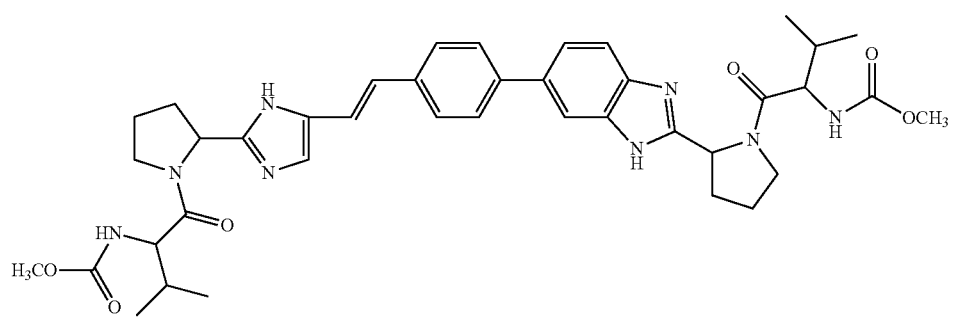
19
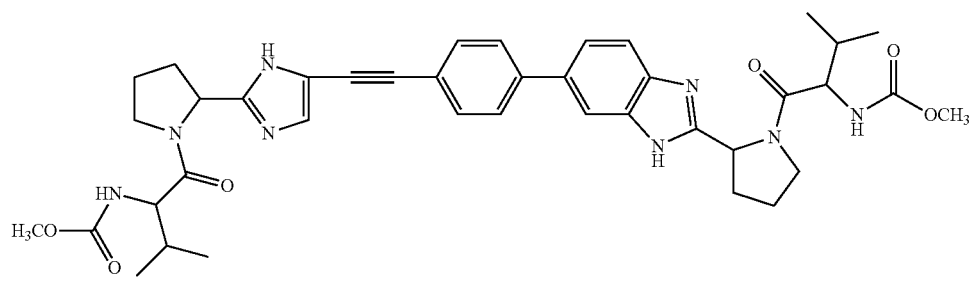
20
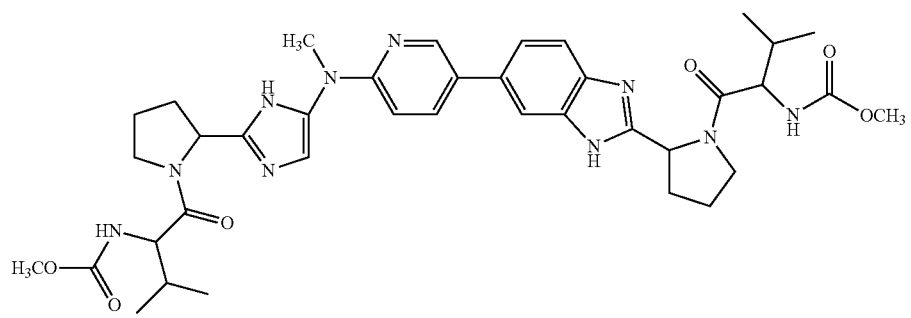

21
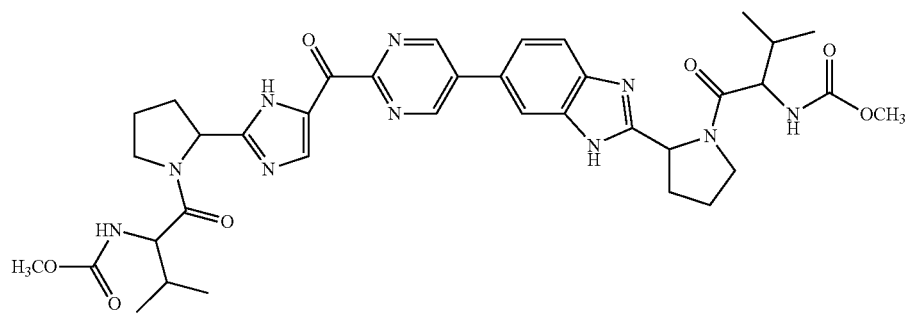
22
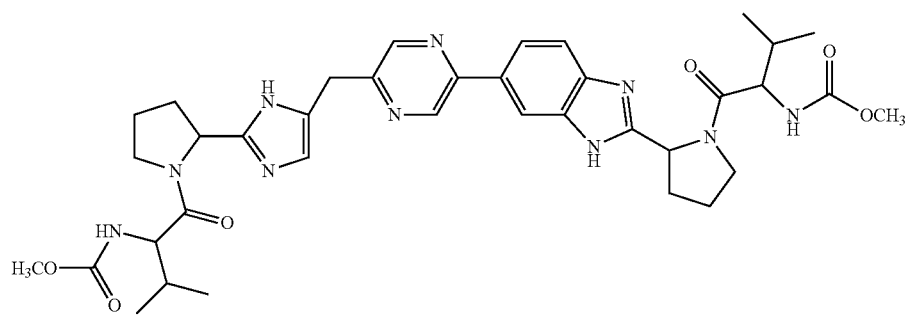
23
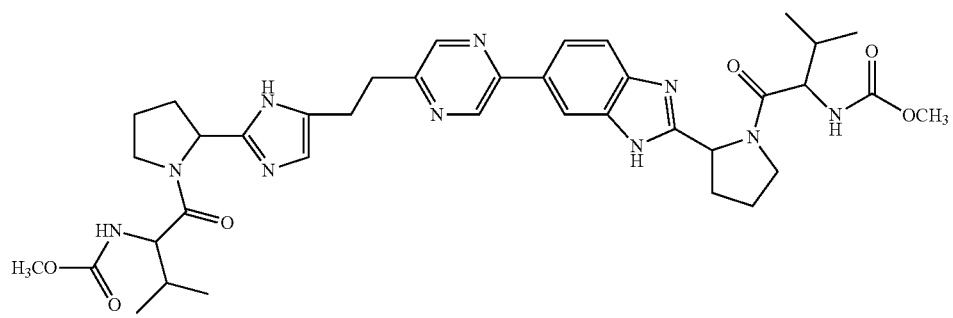
24
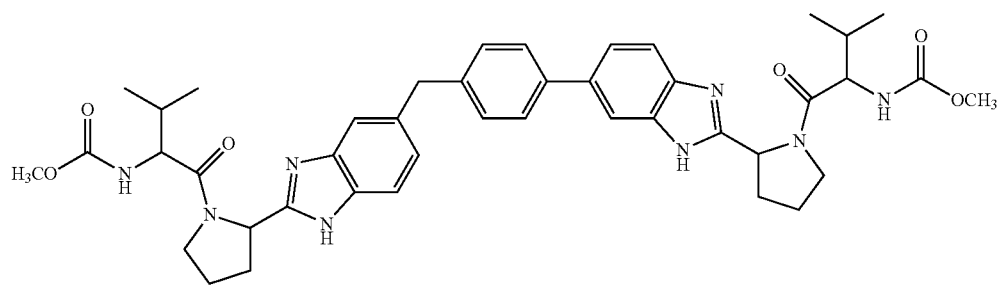
25
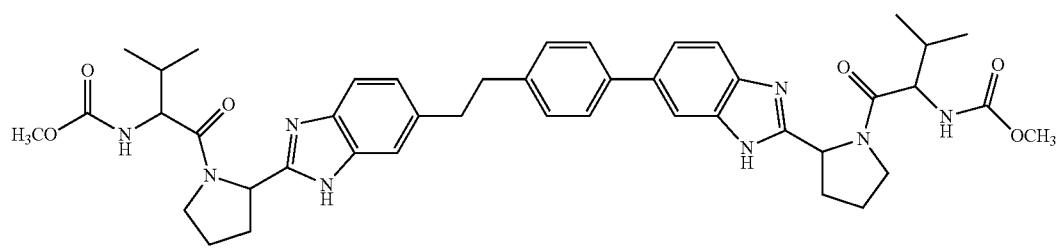

26
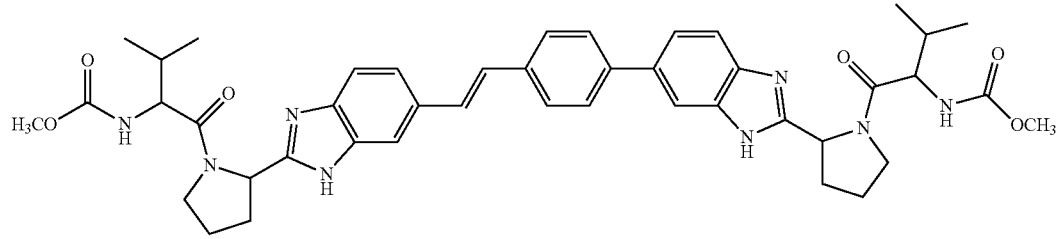
27
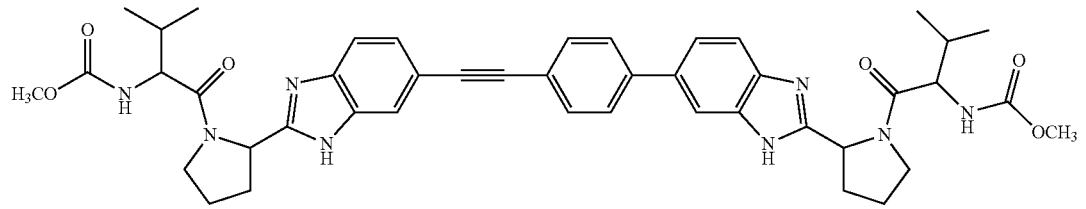
28
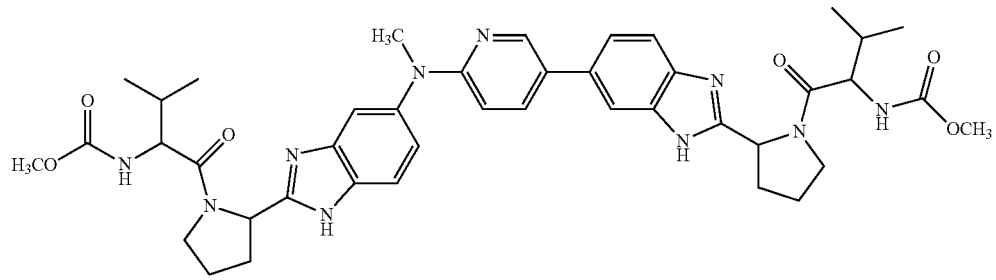
29
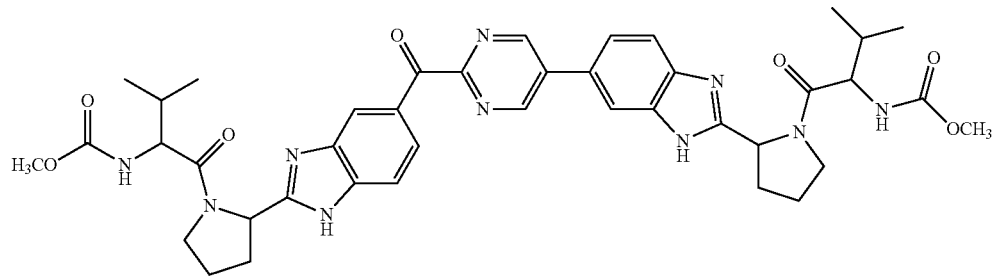
30
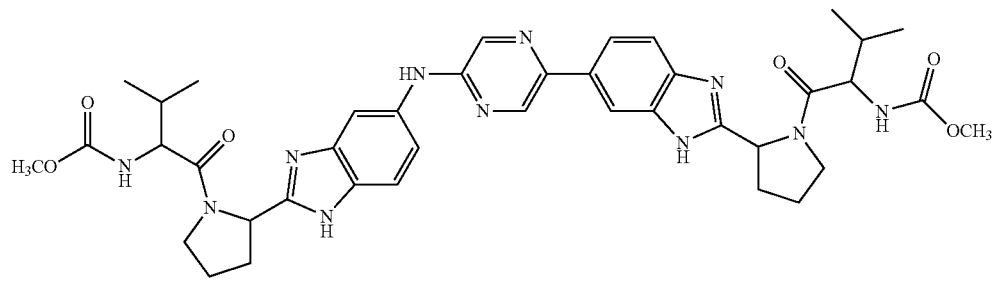
31
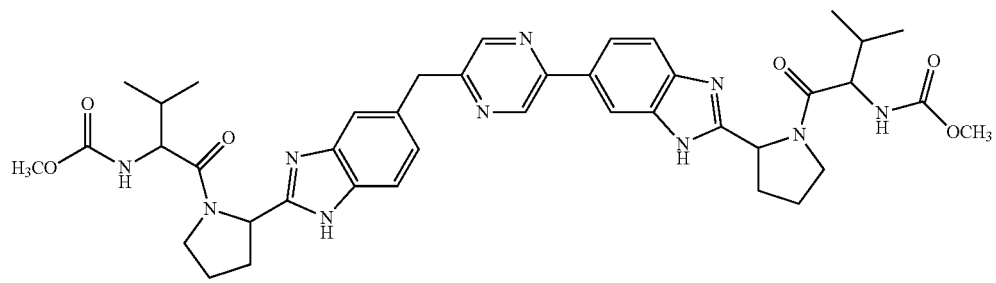

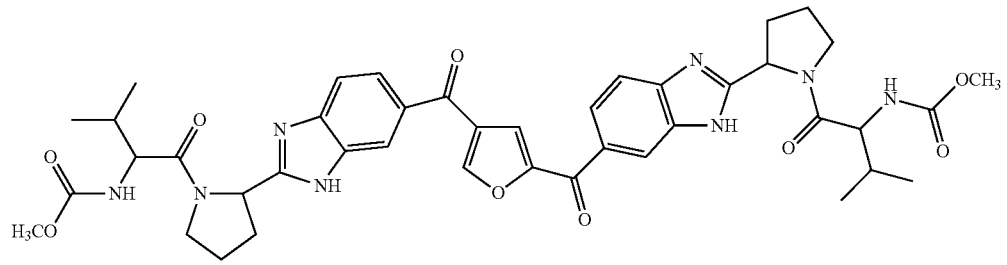
32
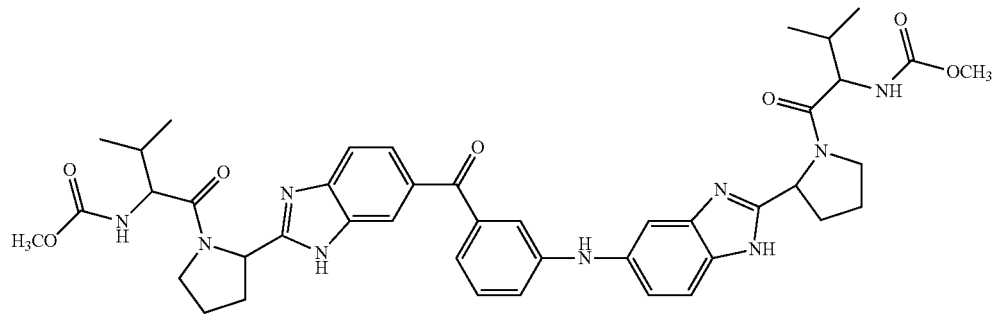
33
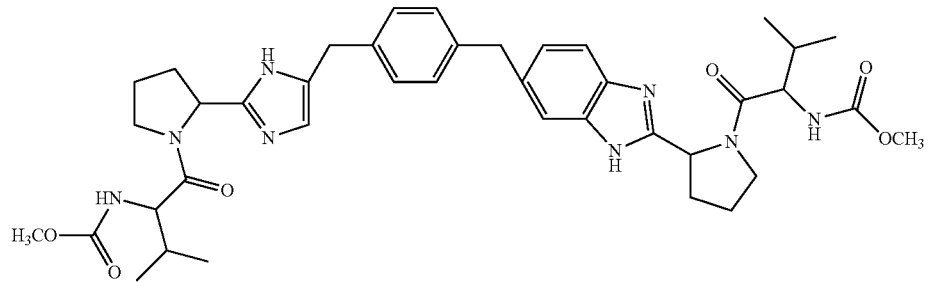
34
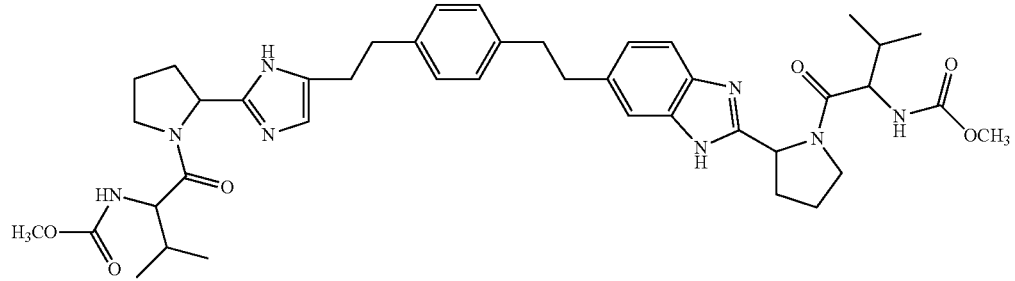
35
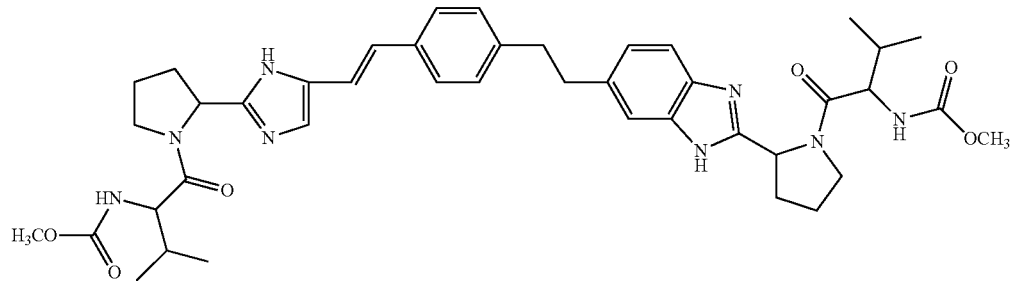
36

-continued
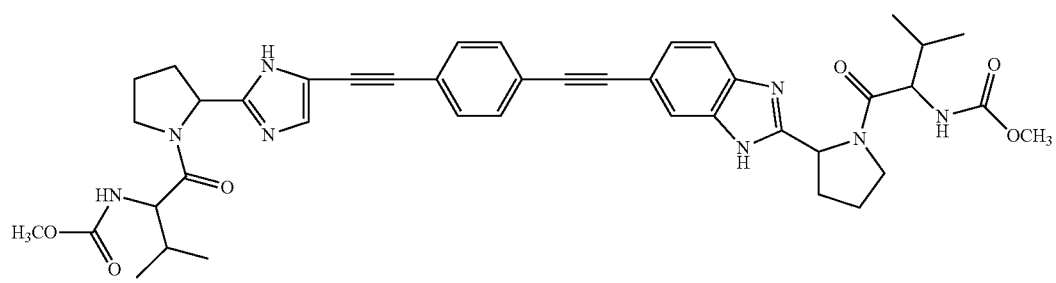
37
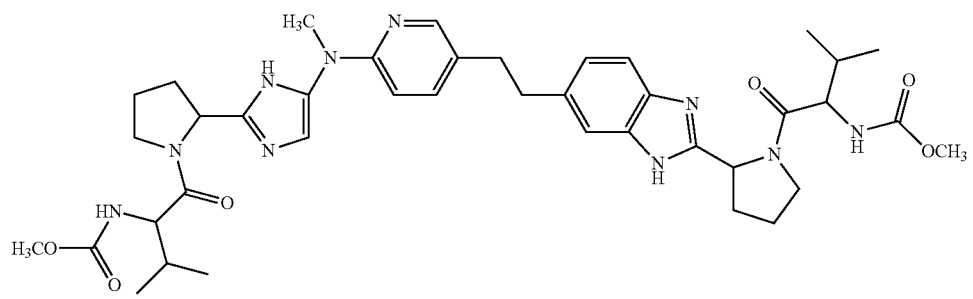
38
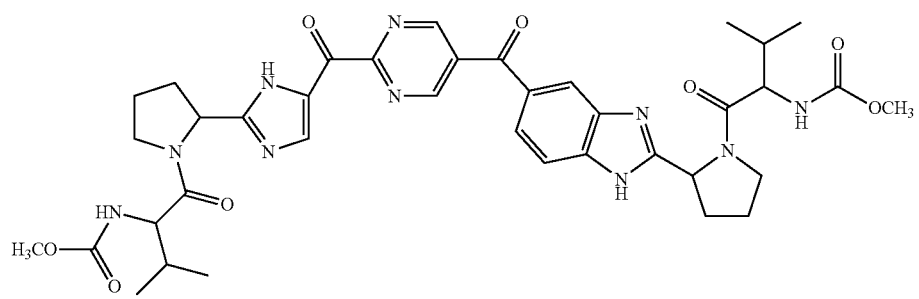
39
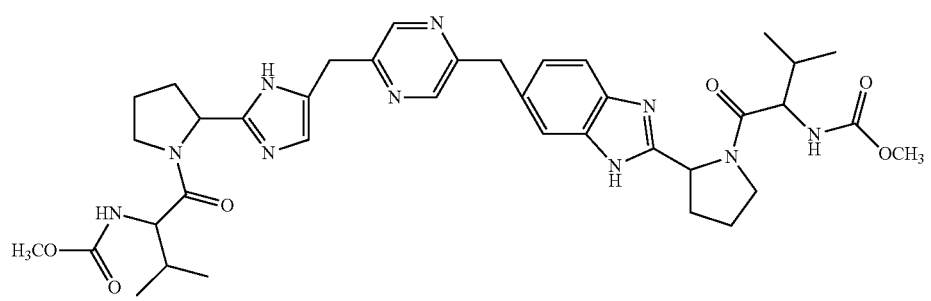
40
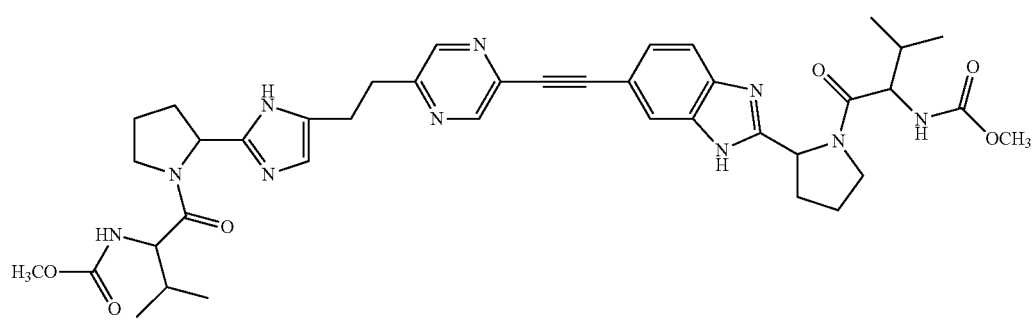
41

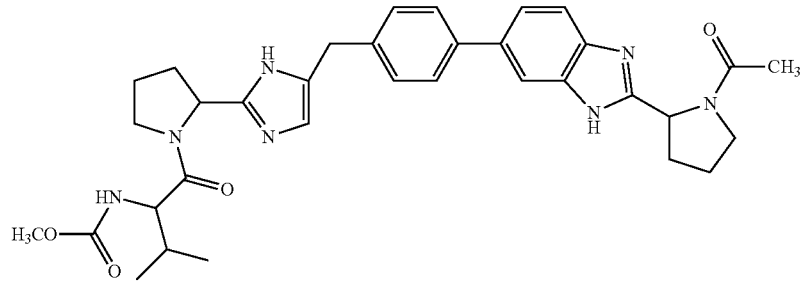
42
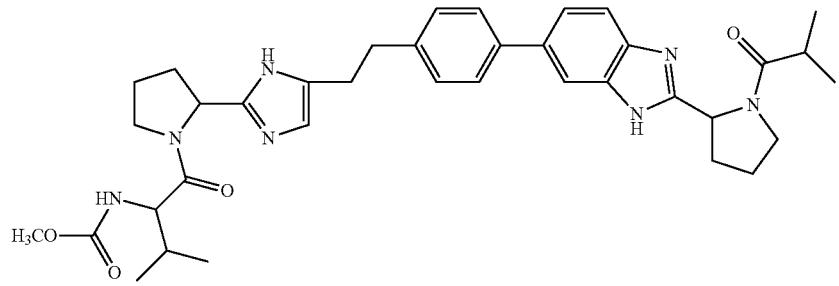
43
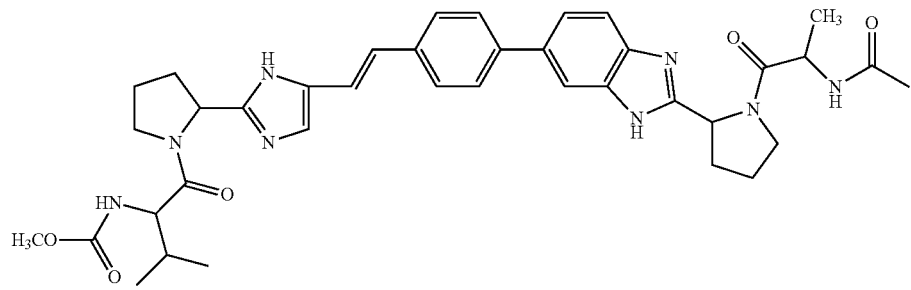
44
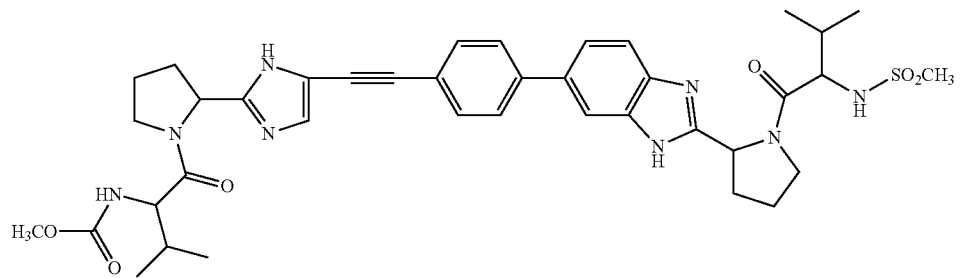
45
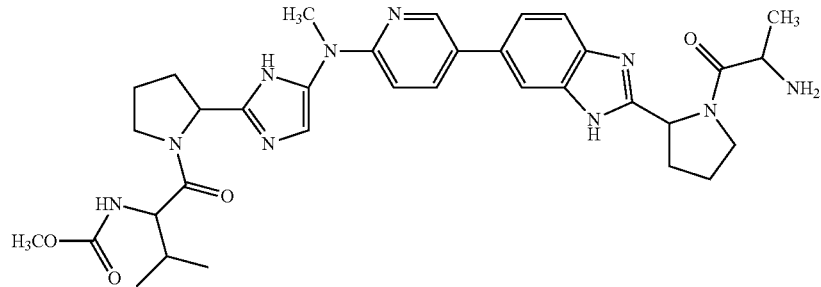
46

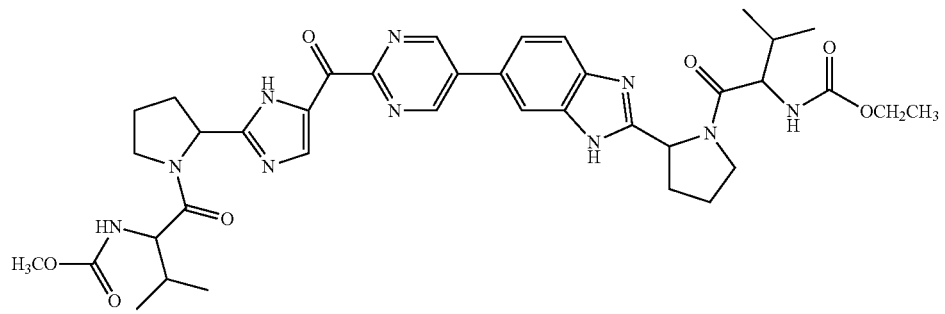
47
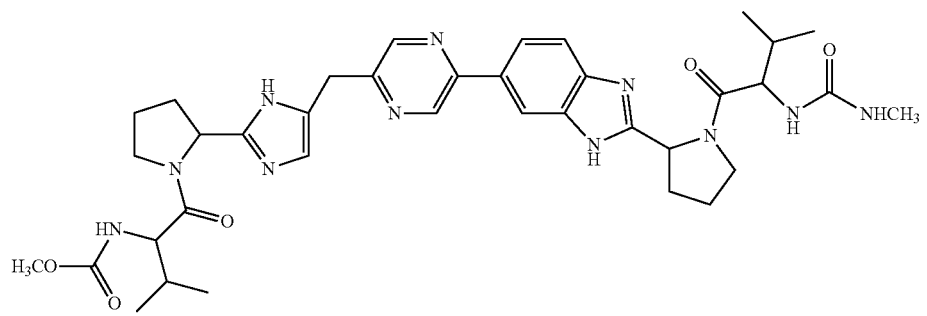
48
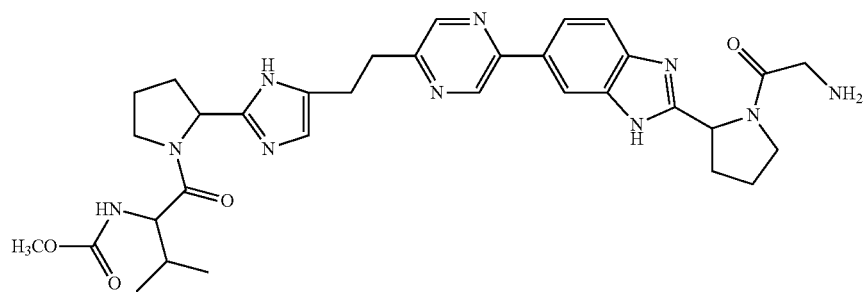
49
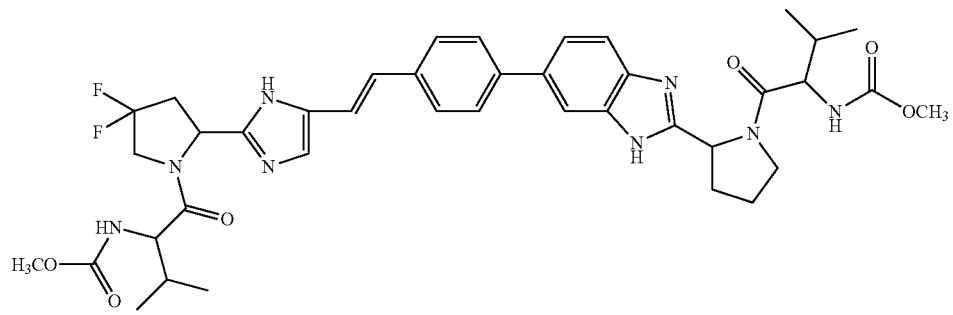
50
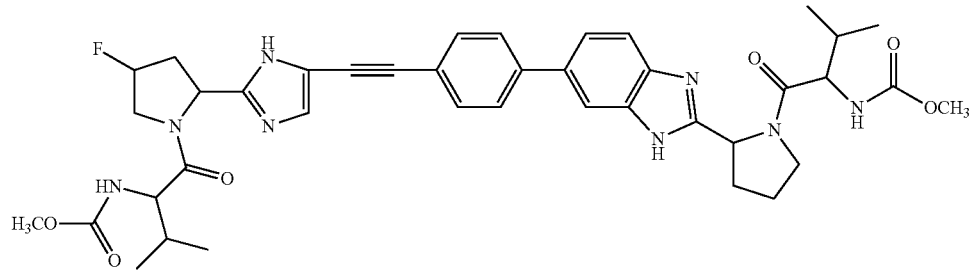
51

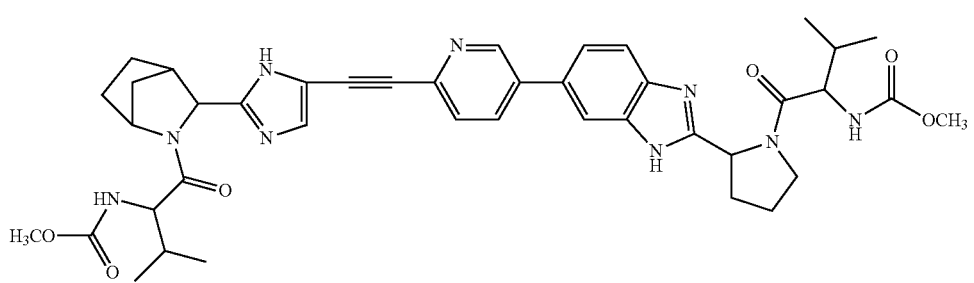
52
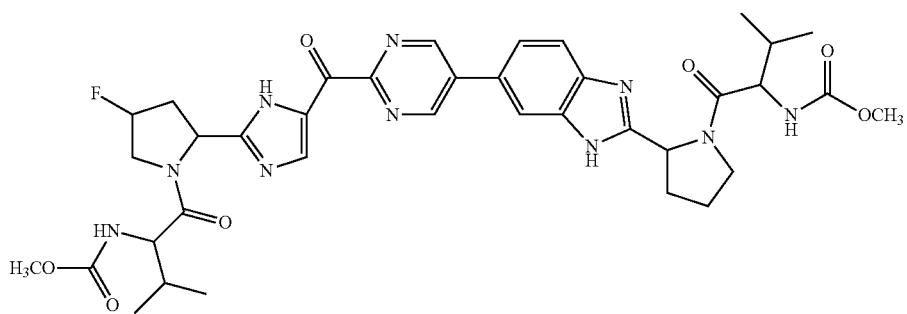
53
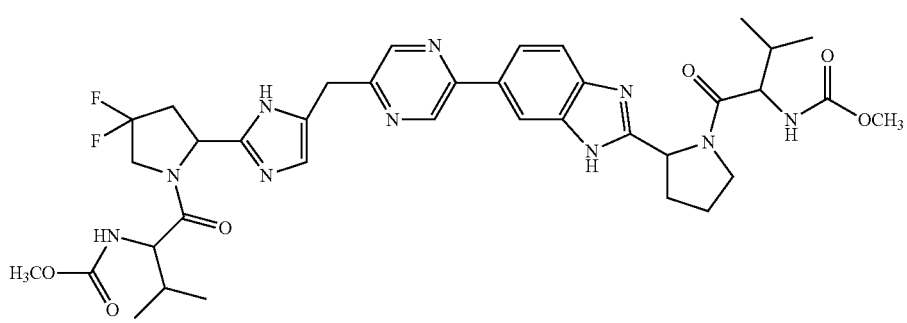
54
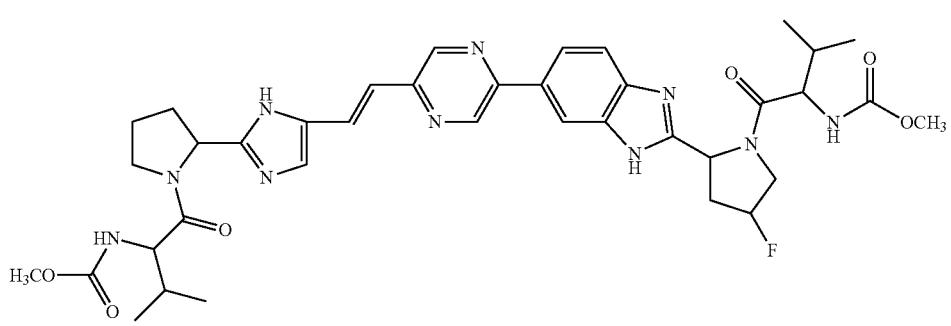
55
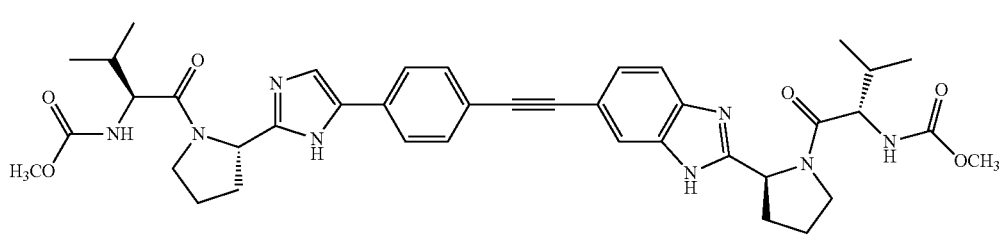
56

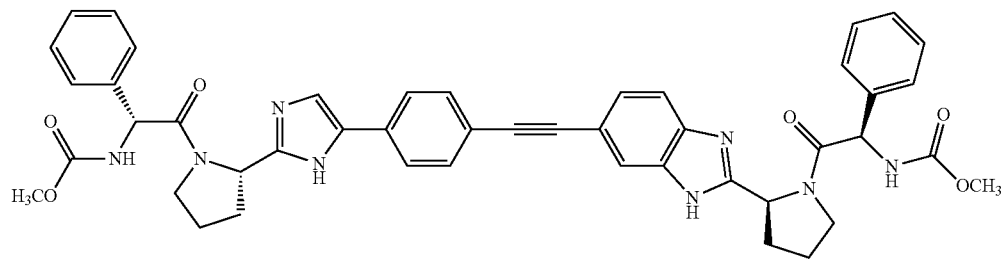

57

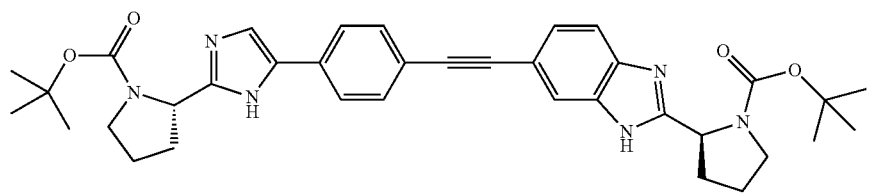

58 and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in schemes 1-6 below. Alternative synthetic pathways and analogous structures will be apparent to those skilled in the art of organic synthesis. All stereoisomers and tautomeric forms of the compounds are contemplated.

Scheme 1 illustrates a method useful for making the compounds of formula A3, which are useful intermediates for making the Compounds of Formula (I).

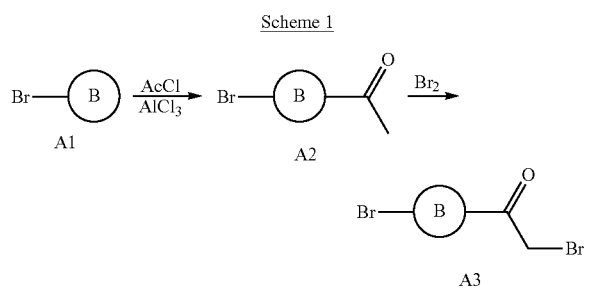

wherein B is defined above for the Compounds of Formula (I).

When a bromoacetyl derivative of formula A3 is not readily available, it can be prepared via a Friedel-Crafts acylation on an aryl bromide or heteroaryl bromide of formula A1 using well-known methods, (e.g., those described in Kricka et al., *J. Chem. Soc. Perkin Trans I*, 859-863 (1973), and Kricka et al., *Chem. Rew.*, 74, 101-123, (1974)) to provide the acylated products of formula A2. A compound of formula A2 can then be brominated (using, for example, bromine in acetic acid; N-bromosuccinimide; CuBr$_2$; or trimethylphenylammonium tribromide) to provide Compounds of formula A3.

Scheme 2 illustrates an alternative method useful for making the compounds of formula A3, which are useful intermediates for making the Compounds of Formula (I).

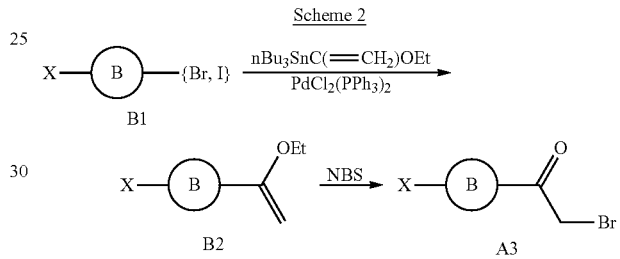

wherein B is defined above for the Compounds of Formula (I).

The bromo or iodo group of a compound of formula B1 can be converted to an ethoxy vinyl derivative of formula B2, by the reaction of B1 with commercially available (alpha-ethoxyvinyl) tributylstannane in the presence of palladium(II). A compound of formula B2 can then be brominated (using, for example, bromine in acetic acid; N-bromosuccinimide; CuBr$_2$; or trimethylphenylammonium tribromide) to provide Compounds of formula A3.

Scheme 3 illustrates an alternative method useful for making the compounds of formula C4, which are useful intermediates for making the Compounds of Formula (I).

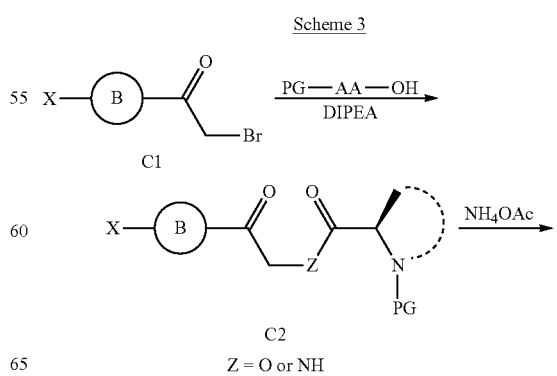

Z = O or NH

-continued

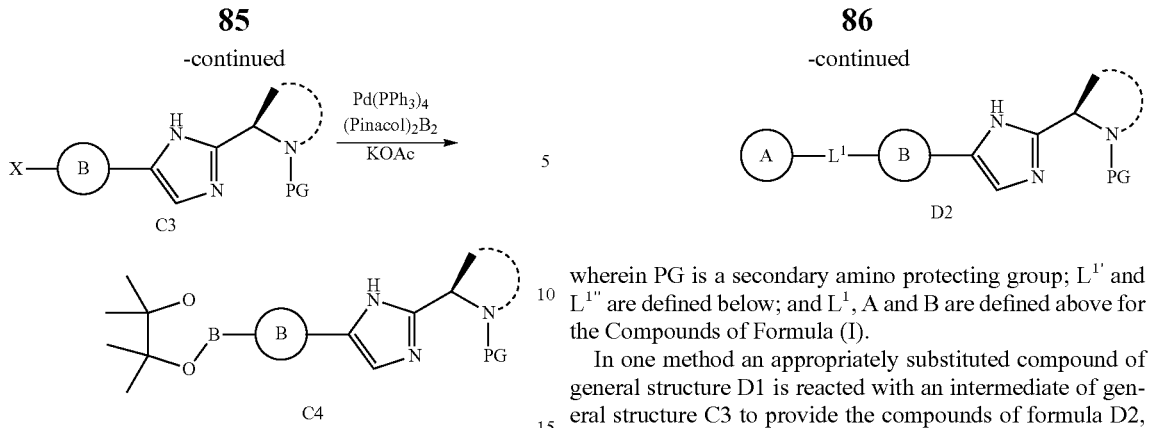

wherein X is a halide or —OTf; Z is —O— or —NH—; PG is a secondary amine protecting group; and B is defined above for the Compounds of Formula (I).

A bromoacetyl functionalized compound of formula C1 (commercially available or made using the methods described in Schemes 1 and 2) can be reacted with an N-protected amino acid (to provide compounds of C2 wherein Z=O) or an amide derivative (to provide compounds of C2 wherein Z=NH) in the presence of a tertiary amine base to provide a compound of formula C2. A compound of formula C2, when heated in the presence of an ammonia source such as ammonium acetate, can provide the imidazole Compounds of formula C3. A compound of formula C3 can then be converted to an organometallic such as the boronic acid compound of formula C4 using, for example, bis(pinocolato) diboron in the presence of a palladium catalyst such as $Pd_2(dba)_3$.

Scheme 4 shows methods useful for the preparation of the Compounds of Formula (I) wherein ring D is an imidazole, $L^2$ is a bond, and $R^4$ is a nitrogen containing heterocycloalkyl ring.

Scheme 4

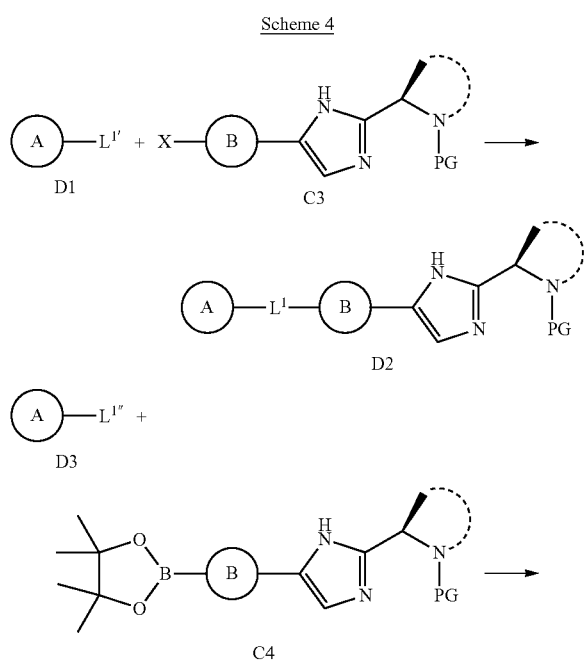

-continued

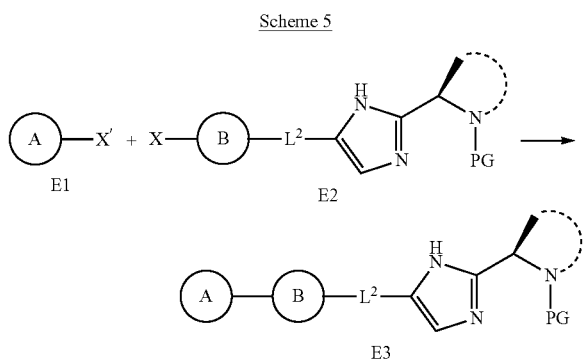

wherein PG is a secondary amino protecting group; $L^{1'}$ and $L^{1'''}$ are defined below; and $L^1$, A and B are defined above for the Compounds of Formula (I).

In one method an appropriately substituted compound of general structure D1 is reacted with an intermediate of general structure C3 to provide the compounds of formula D2, which correspond to the Compounds of Formula (I) wherein ring D is an imidazole, $L^2$ is a bond, and $R^4$ is a nitrogen containing heterocycloalkyl ring. When the linker $L^1$ is attached to ring B through a —C($R^{13}$)=C($R^{13}$)— or an acetylene, a compound of general structure D2 can be prepared by reaction of a compound of formula C4 with a compound of formula D3, wherein L1' is a —C($R^{13}$)=C($R^{13}$)H or a terminal acetylene using the known Castro-Stevens reaction (i.e., Pd(O), Cu(I), amine; see Castro et al. *J. Organic Chem.* 1963, 28, 3136 and Sonogashira, Comprehensive Organic Synthesis, Vol 3, Chapter 2). When the linker $L^1$ is an alkylene group, it can be prepared by reduction of the corresponding alkenylene or alkynylene analog by reduction methods such as exposure to hydrogen under pressure in the presence of a palladium catalyst. When the linker $L^1$ is attached to ring B through a nitrogen atom, oxygen atom or an chain terminating in a nitrogen or oxygen atom, and intermediate of general structure D1 can be coupled to a compound of general structure C3 to provide Compound of general structure D2 by direct methods, such as heating the corresponding amine or alcohol with an aryl halide mediated by a transition metal (Buchwald, J. Am. Chem. Soc. 1996, 118, 7215). An alternate method to prepare nitrogen or oxygen linked compounds is use a starting material for the preparation of C3 wherein X is —OH, or —$NH_2$ and then alkylated to provide Compounds of structure D2. Alternate methods are known where group X is a halide in C3 is then converted into a hydroxyl or an amine group and then alkylated to provide Compounds of structure D2. One such method for the hydrolysis of an aryl diazonium salt to a phenol (March, Advanced Organic Chemistry & references therein.)

Scheme 5 shows methods useful for the preparation of the Compounds of Formula (I) wherein ring D is an imidazole, $L^1$ is a bond, and $R^4$ is a nitrogen containing heterocycloalkyl ring.

wherein X is a halide or —OTf; PG is a secondary amino protecting group; X' is a functional group capable of participating in a cross-coupling reaction; and A, B and L² are defined above for the Compounds of Formula (I).

A compound of formula E1 can be coupled with a compound of formula E2, wherein X' is a functional group capable of participating in a cross-coupling reaction, to provide Compounds of formula E3. Compounds in which A is an imidazole and X' is a bromide have been described in US Patent Publication No. 2009/0068140 to Bachand et al. If a compound of formula E1 was not functionalized prior to the coupling reaction, appropriate methods well known in the art of organic synthesis can be used to prepare final Compounds of Formula (I). Functionalization of E3 when ring A contains a NH with a R¹ as defined above, can be accomplished by alkylation methods (an alkyl halide in the presence of a non-nucleophilic base, such as $Cs_2CO_3$,) or acylation methods described above for amide formation. Functionalization of E3 with a R³ substituent as defined above, can be accomplished by alkylation methods (an alkyl halide in the presence of a base, eg. LDA), oxidation methods (meta-chloroperoxy benzoic acid), or acylation methods described above for amide formation. Compounds of formula E3 may need to have the protecting group PG removed. In such instances, for example, when PG is a t-butyloxycarbonyl (Boc) group, treatment of E3 with a strong acid such as HCl in dioxane or trifluoroacetic acid in ether can be used to remove the protecting group and provide the corresponding NH analog.

Scheme 6 illustrates a method useful for making the Compounds of Formula (I) wherein D is imidazolyl and R⁴ is a nitrogen-containing heterocycloalkyl group.

Scheme 6

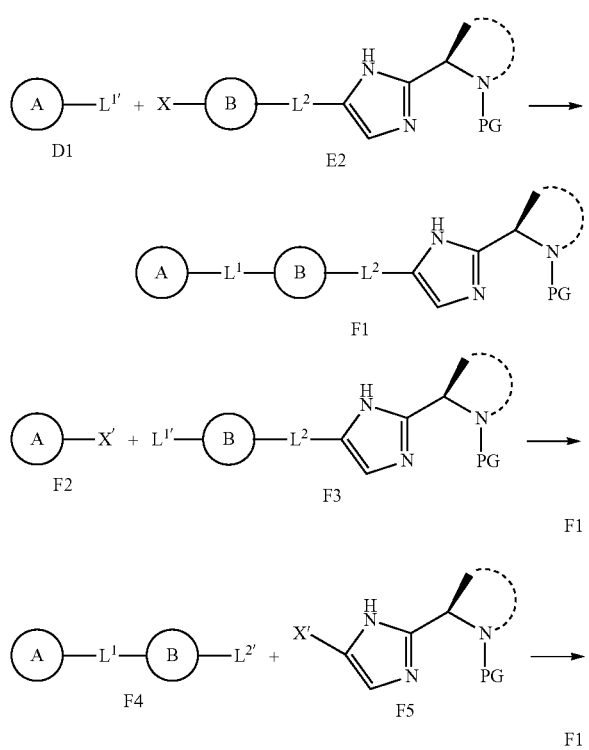

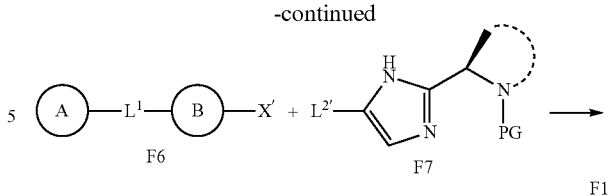

One skilled in the art of organic chemistry will recognize that methods analogous to the ones described in detail in schemes 1-6 are applicable to the preparation of compounds of formula F1. For example an appropriately substituted bicyclic ring system of formula F4, wherein A is a R⁵-substituted pyrrolidine-benzimidazolyl system, L¹ is a methylene group, B is a phenyl ring, and L²' is —C≡C(H)SnBu₃, can be reacted with a compound of formula F5 wherein X' is a bromide to provide Compounds F1. More specifically, preferred conditions for the coupling of a vinyl-tin reagent have been reviewed (Stille, Angew Chem. Int. Edition 1986, 25, 508). Hydrogenation of a compound of formula F1 wherein L² is —C(H)═C(H)—, affords a compound of formula F1 wherein L² is —CH₂—CH₂—. Wacker-oxidation of a compound of formula F1 wherein L² is —C(H)═C(H)—, affords a compound of formula F1 wherein L² is —CH₂—C(═O)—. Additional functionalization of a compound of formula F1 can be accomplished by deprotection and reaction with an appropriate R⁵ substituent as exemplified in the Examples below.

The starting materials and reagents described in Schemes 1-6 above are either available from commercial suppliers such as Sigma-Aldrich (St. Louis, Mo.) and Acros Organics Co. (Fair Lawn, N.J.), or can be prepared using methods well-known to those of skill in the art of organic synthesis.

In some compounds contemplated, R³ and/or R⁴ contains a nitrogen atom, which can be synthesized from an amino acid derived intermediate, such as proline, 4,4-difluoroproline, (S)-2-piperidine carboxylic acid, valine, alanine, norvaline, etc. Methods have been described in the general literature as well as in US Patent Publication No. 2009/0068140 to Bachand et al., for the preparation of such amino acid derivatives.

Methods of preparing contemplated compounds wherein R⁵ is other than hydrogen are well known in the art of organic chemistry. Specifically, when R³ is attached to through an alkyl carbon, alkylation methods, such as the reaction of with an alkyl halide and a base or with an aldehyde and a reducing agent, are well known in the art. Additionally, when R⁵ is attached to through a carbonyl carbon, acylation methods, such as with a protected carboxylic acid and an activating reagent are well known in the art of organic synthesis. When the carboxylic acid is a protected amino acid, preferred methods include the use of DECI, HATU or PyBrop in a polar organic solvent (e.g., DMF, dioxane) in the presence of a non-nucleophilic amine base, such as diisopropylethylamine or triethylamine.

One skilled in the art of organic synthesis will recognize that the synthesis of the core (the A-L¹-B-L²-D moiety) of the Compounds of Formula (I) may require the need for the protection of certain functional groups (i.e., derivatization for the purpose of chemical compatibility with a particular reaction condition). Suitable protecting groups for the various functional groups of contemplated compounds and methods for their installation and removal can be found in Greene et al., *Protective Groups in Organic Synthesis*, Wiley-Interscience, New York, (1999).

One skilled in the art of organic synthesis will also recognize that one route of the possible routes for the synthesis of the contemplated Compounds of Formula (I) may be more desirable depending on the choice of appendage substituents. An example of such would be if the $R^5$ substituent is base sensitive and the cyclization method used to form ring B is mediated by strong base. One skilled in the art of organic synthesis would plan a synthesis in which ring B is constructed before the appendage of the $R^5$ substituent.

Additionally, one skilled in the art will recognize that the synthesis of certain contemplated Compound of Formula (I) that the order of synthetic steps required may differ from the examples below to avoid certain functional group incompatibilities. An example of such would be if the $R^1$ substituent is base sensitive and the $R^3$ is not-base sensitive and the method chosen for appended $R^3$ is mediated by a base. One skilled in the art of organic synthesis would plan a synthesis in which $R^3$ is attached to the core before the appendage of the $R^1$ substituent.

The preparation of the ring systems contemplated in this invention, have been described in the literature and in compendia such as "Comprehensive Heterocyclic Chemistry" editions I, II and III, published by Elsevier and edited by A. R. Katritzky & R. J K. Taylor. One skilled in the art of organic chemistry will recognize that in some cases one or more of the rings of the contemplated invention can be constructed by cyclization methods or rearrangement reactions well known in the art of organic synthesis. Aromatic and heteroaromatic rings can be formed by cycloaddition reactions well known in the art which include the Diels-Alder reaction, Hetero Diels-Alder reaction, dipolar addition (2+2 and 2+3) reactions and cycloaddition reactions. Heteroaromatic rings in many cases can be prepared via a cyclization reaction followed by removal of water such as the intermolecular reaction of an aldehyde with an amine followed by loss of water. Cycloalkyl rings and heterocycloalkyl rings can be prepared by reduction of the related aromatic analog. Cycloalkyl and heterocycloalkyl rings can also be prepared by cyclization reactions. Examples of a cyclization reaction include the intermolecular reaction of an amine anion which a halide or the reaction with an amine with an aldehyde under reductive amination conditions (e.g., sodium triacetoxyborohydride, sodium borohydride). Another such cyclization reaction is the intermolecular reaction of a hydroxyl anion with a halide. Oxygen containing heterocycloalkyl rings can be prepared by rearrangement reactions. One such rearrangement reaction is the Baeyer-Villiger rearrangement of a cyclic ketone to form lactones. These methods are well in the art of organic chemistry and have been described in the literature and in compendia such as "Comprehensive Heterocyclic Chemistry" editions I, II and III, published by Elsevier and edited by A. R. Katritzky & R. J K Taylor to prepare the ring systems contemplated in this invention.

The functionalization of the ring systems contemplated in this invention, have been described in the literature and in compendia such as "Comprehensive Heterocyclic Chemistry" editions I, II and III, published by Elsevier and edited by A. R. Katritzky & R J K Taylor. One skilled in the art of organic chemistry will recognize that the use of a functionalized pre-formed ring such as X-A, can be coupled with a X'-$L^1$-B, X'-$L^1$-B-D, X'-$L^1$-B-$L^2$-D, or X'-B-$L^2$-D wherein, X and X' are suitable functional groups that can undergo cross-coupling reactions and A, B, and D are as described above. One such set of suitable functional groups which can participate in transition metal-mediated coupling chemistry are —B(OH)$_2$, —B(Oalkyl)$_2$, —B(N-methyliminodiacetic acid), Sn(alkyl)$_3$, —MgBr, —MgCl, —ZnBr, —ZnCl.

Another set of suitable functional groups which can participate in transition metal-mediated coupling reactions are Cl, Br, I and O-triflate. Well known conditions for cross-coupling reactions are were X and X' are each selected from a different functional group set. Other conditions for cross-coupling reactions are known where both partners are a halide. The recent discovery and use of N-methyliminodiacetic acid boronates has been described by M. Burke et al. in *J. Am. Chem. Soc.* 2009 web edition 10.1021/ja901416p. Suitable cross-coupling methods include, but are not limited to, a Stille coupling (see Choshi et al., *J. Org. Chem.*, 62:2535-2543 (1997), and Scott et al., *J. Am. Chem. Soc.*, 106:4630 (1984)), a Suzuki-Miayura coupling (*Angew Chem. Int. Ed. Engl* 2001, 40, 4544), a Negishi coupling (see Zhou et al., *J. Am. Chem. Soc.*, 127:12537-12530 (2003)), and a Kumada coupling (see Kumada, *Pure Appl. Chem.*, 52:669 (1980) and Fu et al., *Angew. Chem.* 114:4363 (2002).

Manipulation of the required substitution patterns have also been described in the available chemical literature as summarized in compendia such as "Comprehensive Organic Chemistry" published by Elsevier and edited by DH R. Barton and W. D. 011 is; "Comprehensive Organic Functional Group Transformations" edited by A. R. Katritzky & R. J K Taylor and "Comprehensive Organic Transformation" published by Wily-CVH and edited by R. C. Larock and "March's Advanced Organic Chemistry: Reactions, Mechanism and Structure" by M. Smith and J. March, $6^{th}$ Edition and published by Wiley-Interscience, 2007.

One skilled in the art of organic synthesis will recognize that the synthesis of certain Compounds of Formula (I) require the construction of an amide bond. Methods useful for making such amide bonds, include but are not limited to, the use of a reactive carboxyl derivative (e.g., acid halide, or ester at elevated temperatures) or the use of an acid with a coupling reagent (e.g., EDCI, DCC, HATU, PyBrop) with an amine.

One skilled in the art of organic synthesis will recognize that the synthesis of certain Compounds of Formula (I) require a carbon-nitrogen or carbon-oxygen bond. One method for the construction of a carbon-oxygen bond includes the reaction of the oxygen atom present in such functional groups as a carboxylic acid or an alcohol with a compound containing a carbon atom functionalized with a leaving group in the presence of a base such as cesium carbonate or LDA. One method for the construction of a carbon-nitrogen bond includes the reaction of the amine atom present in such functional groups as an amide or an amine with a compound containing a carbon atom functionalized with a leaving group in the presence of a base such as cesium carbonate or LDA. Typical leaving groups include but are not limited to a halide or O-mesylate.

The starting materials used and the intermediates prepared using the methods set forth in schemes 1-6 above may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from Me₄Si with number of protons, multiplicities, and coupling constants in Hertz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 minutes—10% CH₃CN, 5 minutes—95% CH₃CN, 5-7 minutes—95% CH₃CN, 7 minutes—stop. The retention time and observed parent ion are given. Flash column chromatography was either performed using pre-packed normal phase silica from Biotage, Inc., and unless otherwise, elution was using a gradient of hexanes/ethyl acetate, from 100% hexanes to 100% ethyl acetate. Reverse phase HPLC was preformed using a C18 column and unless noted otherwise using an elution of 95% acetonitrile/5% water to 10% acetonitrile/90% water.

Example 1

Preparation of Intermediate Compound Int-1a

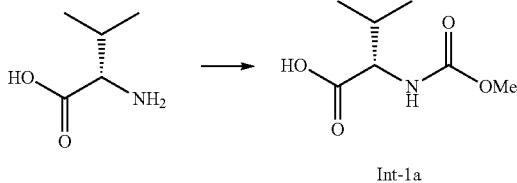

Int-1a

To a solution of L-valine (10.0 g, 85.3 mmol) in 1 M aqueous NaOH solution (86 mL) at room temperature was added solid sodium carbonate (4.60 g, 43.4 mmol). The reaction mixture was cooled to 0° C. (ice bath) and then methyl chloroformate (7.20 mL, 93.6 mmol) was added dropwise over 20 minutes. The reaction mixture was then allowed to warm to room temperature, and allowed to stir at room temperature for an additional 4 hours. The reaction mixture was then diluted with diethyl ether (100 mL), the resulting solution was cooled to at 0° C., and then concentrated hydrochloric acid (18 mL, 216 mmol) was added slowly. The reaction was extracted with EtOAc (3×100 mL) and the combined organics were dried over MgSO₄, filtered and concentrated in vacuo to provide Compound Int-1a (13.5 g, 90%), which was used without further purification.

The following intermediates can be prepared by the reaction of L-valine with isopropyl chloroformate (Aldrich Inc.), 2-methoxyethyl chloroformate (Aldrich) or with 1-methylcyclopropyl hydroxysuccinimide respectively, using the method described immediately above.

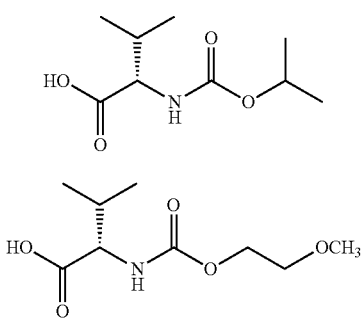

Int-1b

Int-1c

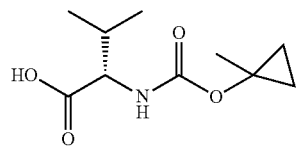

Int-1d

Example 2

Preparation of Intermediate Compound Int-2a

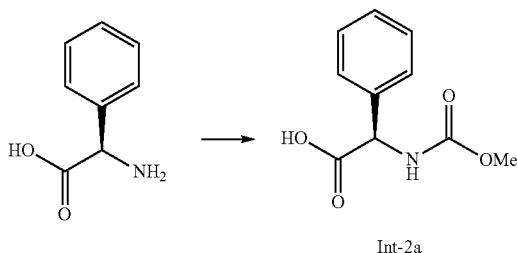 [SMILES: N[C@@H](C(=O)O)c1ccccc1 ; COC(=O)N[C@@H](C(=O)O)c1ccccc1]

Int-2a

To a solution of D-phenylglycine (10.0 g, 66.1 mmol) and NaOH (21.2 g, 265 mmol) in water (60 mL) at 0° C. was added methyl chloroformate (10.2 mL, 133 mmol) dropwise over 20 minutes. The resulting mixture was allowed to stir at 0° C. for 1 hour, then was acidified using concentrated hydrochloric acid (25 mL, 300 mmol). The acidic solution was extracted with EtOAc (3×100 mL) and the combined organics were dried over MgSO₄, filtered and concentrated in vacuo to provide Compound Int-2a (12.6 g, 91%), which was used without further purification.

The following intermediates can be prepared by the reaction of L-Alanine and 4-F phenylglycine respectively with methyl chloroformate (Aldrich Inc.), using the method described immediately above.

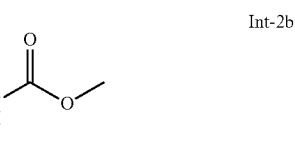

Int-2b

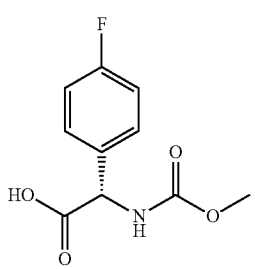

Int-2c

Example 3

Preparation of Intermediate Compound Int-3a

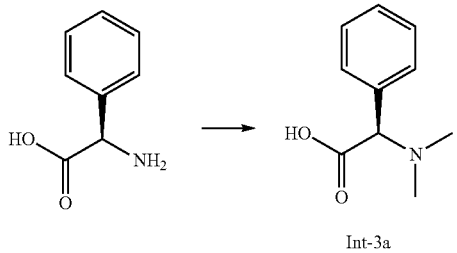

Int-3a

A solution of D-phenylglycine (20.0 g, 132 mmol), 37% aqueous formaldehyde (66 mL, 814 mmol) and 5% Pd on carbon (8.0 g, mmol) in a mixture of methanol (80 mL) and 1 N HCl (60 mL) was placed on a hydrogenation shaker and shook under an atmosphere of 35-40 psi hydrogen for 4 hours. The reaction was then flushed with nitrogen, filtered through a celite pad and concentrated in vacuo to provide Compound Int-3a (29.7 g, quant.) as a white solid, which was used without further purification.

Example 4

Preparation of Intermediate Compound Int-4e

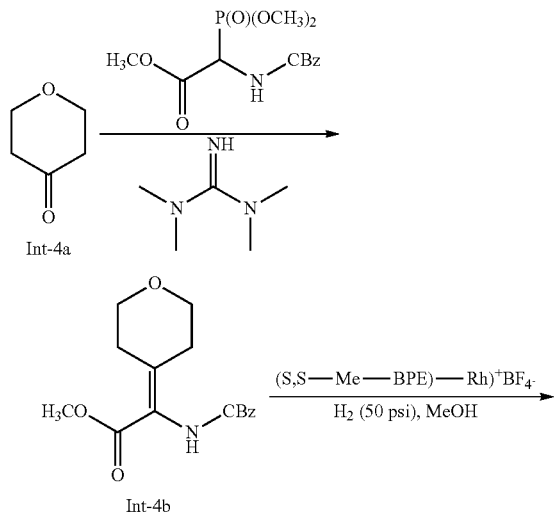

Int-4c

-continued

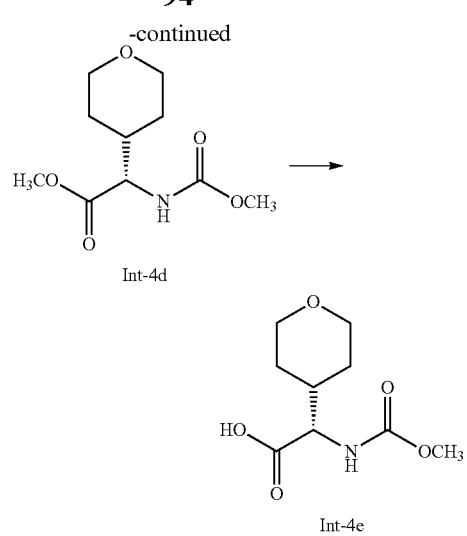

Int-4d

Int-4e

Step A—Synthesis of Compound Int-4a

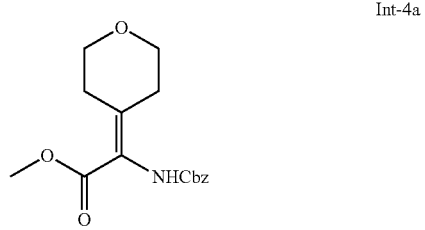 [SMILES: COC(=O)C(NC(=O)OCc1ccccc1)=C1CCOCC1]

Int-4a

To a solution of methyl 2-(benzyloxycarbonylamino)-2-(dimethoxyphosphoryl)acetate (10.0 g, 30.2 mmol, prepared according to the method described in Hamada et al., *Organic Letters*; English; 11; 20; 2009; 4664-4667) in THF (100 mL) at −20° C. was added tetramethylguanidine (4.20 mL, 33.2 mmol). The reaction mixture was allowed to stir at −20° C. for 1 hour then dihydro-2H-pyran-4(3H)-one (4a) was added (3.1 mL, 33.2 mmol) in THF (5 mL) and the reaction mixture was warmed to room temperature and stirred for about 15 hours. EtOAc (200 mL) was added and the organic mixture was washed with water (3×50 mL) and brine (50 mL). The organic layers were combined and dried over $Na_2SO_4$, filtered and concentrated in vacuo. The crude product was purified using flash chromatography on an ISCO 330 g Redi-Sep column using 0-35% EtOAc/hexanes as the eluent to provide Compound Int-4a as a white solid (615 mg, 45%). $^1H$ NMR ($CDCl_3$) δ 7.40-7.30 (m, 5H), 6.00 (br s, 1H), 5.12 (s, 2H), 3.80-3.65 (m, 7H), 2.92 (m, 2H), 2.52-2.48 (m, 2H).

Step B—Synthesis of Compound Int-4-b

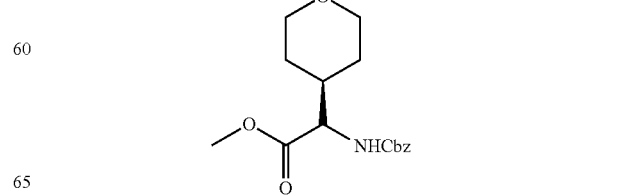

Int-4b

To a solution of Compound Int-4a (2.43 g, 7.96 mmol) in methanol (160 mL) previously purged with $N_2$ was added (−)-1,2-Bis((2S,5S)-2,5-dimethylphospholano)ethane (cyclooctadiene)rhodium(I) tetrafluoroborate (487 mg, 0.880 mmol) under $N_2$. The mixture was shaken in a Parr shaker apparatus for 18 hours at 50 psi of $H_2$. After evacuating the hydrogen, the suspension was filtered and the filtrate was concentrated in vacuo to provide Compound Int-4b as a white solid (1.30 g, 53%). $^1$H NMR (CDCl$_3$) δ 7.40-7.30 (m, 5H), 5.32 (br s, 1H), 5.12 (s, 2H), 4.40-4.30 (m, 1H), 4.00-3.95 (m, 2H), 3.75 (s, 3H), 3.40-3.25 (m, 2H), 2.10-1.95 (m, 1H), 1.50-1.45 (m, 4H).

Step C—Synthesis of Compound Int-4-c

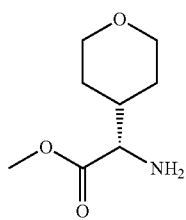

Int-4c

To a suspension of 50% palladium on carbon (10% wet, 200 mg) in absolute ethanol (20 mL) under nitrogen was added Int-4-b (1.06 g, 3.45 mmol). With stirring, the solution was placed under vacuum for 30 seconds and then was opened to a hydrogen gas balloon for 2 hours. After evacuating the hydrogen, the suspension was filtered through a Celite pad and the pad washed with ethanol (2×20 mL). The filtrate was concentrated in vacuo to provide Compound Int-4c as a colorless oil (585 mg, 98%). $^1$H NMR (CDCl$_3$) δ 4.06-3.96 (m, 2H), 3.73 (s, 3H), 3.48-3.28 (m, 3H), 1.92-1.78 (m, 1H), 1.61-1.47 (m, 6H).

Step D—Synthesis of Compound Int-1d

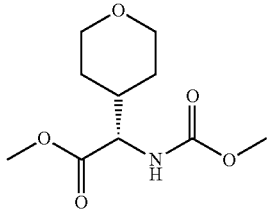

Int-4d

To a solution of Compound Int-4-c (585 mg, 3.37 mmol) and triethylamine (0.710 mL, 5.09 mmol) in CH$_2$Cl$_2$ (6 mL) was added methyl chloroformate (0.290 mL, 3.76 mmol). The reaction mixture was allowed to stir at room temperature for about 15 hours. Water (15 mL) was added and the aqueous mixture was extracted with CH$_2$Cl$_2$ (3×20 mL). The combined organic layers were dried over Na$_2$SO$_4$, filtered and concentrated in vacuo. The crude product was purified using flash chromatography on an ISCO 24 g Redi-Sep column using 0-3% MeOH/CH$_2$Cl$_2$ as the eluent to provide Compound Int-4d as a colorless oil (600 mg, 77%). $^1$H NMR (CDCl$_3$) δ 5.27-5.18 (m, 1H), 4.38-4.28 (m, 1H), 4.06-3.96 (m, 2H), 3.75 (s, 3H), 3.69 (s, 3H), 3.39-3.30 (m, 2H), 2.09-1.94 (m, 1H), 1.59-1.48 (m, 4H).

Step E—Synthesis of Compound Int-4e

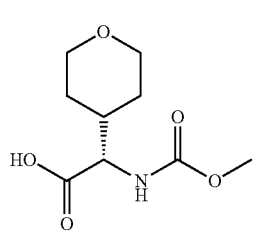

Int-4e

To a solution of Compound Int-4d (600 mg, 2.59 mmol) in THF (5 mL) was added lithium hydroxide monohydrate (218 mg, 5.19 mmol) in water (5 mL) The reaction mixture was allowed to stir at room temperature for 2 hours then concentrated in vacuo to half volume. The aqueous mixture was then acidified with 6N HCl and extracted with EtOAc (7×50 mL). The combined organic layers were dried over Na$_2$SO$_4$, filtered and concentrated in vacuo to provide Compound Int-4e as an off-white solid (485 mg, 86%). $^1$H NMR (CD$_3$OD) δ 4.09-4.07 (m, 1H), 3.96-3.92 (m, 2H), 3.65 (s, 3H), 3.40-3.34 (m, 2H), 2.10-1.99 (m, 1H), 1.56-1.47 (m, 4H).

Example 5

Preparation of Intermediate Compound Int-5f

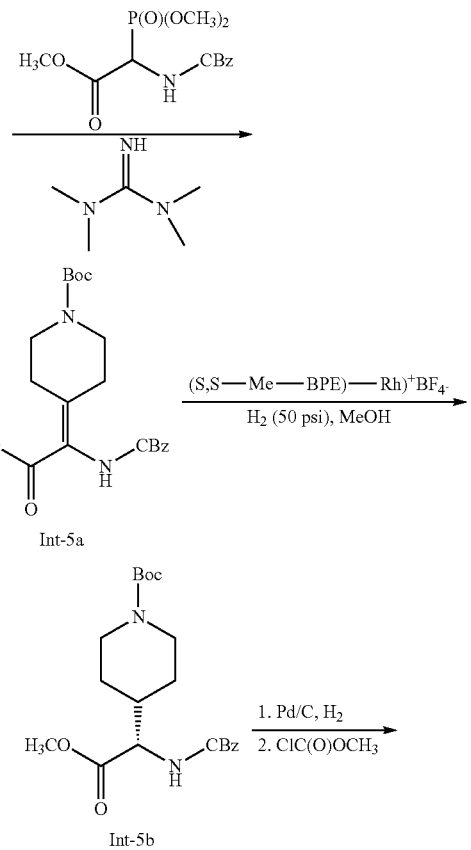

-continued

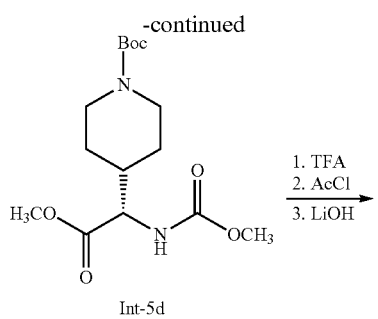

Int-5d

Step A—Synthesis of Compound Int-5a

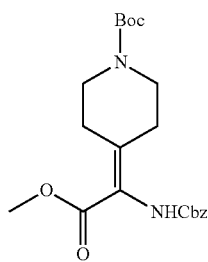

Int-5a

To a solution of methyl 2-(benzyloxycarbonylamino)-2-(dimethoxyphosphoryl)acetate (1.50 g, 4.52 mmol) in THF (5 mL) at −20° C. was added tetramethylguanidine (625 μL, 4.98 mmol). The reaction mixture was allowed to stir at −20° C. for 1 hour, then tert-butyl 4-oxopiperidine-1-carboxylate was added (992 mg, 4.97 mmol) in THF (2 mL) and the reaction mixture was warmed to room temperature and stirred for about 15 hours. EtOAc (90 mL) was added and the organic mixture was washed with water (3×20 mL) and brine (25 mL). The combined organic layers were dried over Na$_2$SO$_4$, filtered and concentrated in vacuo. The crude product was purified using flash chromatography on an ISCO 40 g Redi-Sep column using 0-35% EtOAc/hexanes as the eluent to provide Compound Int-5a as a white semi-solid (1.1 g, 61%). $^1$H NMR (CDCl$_3$) δ 7.40-7.30 (m, 5H), 6.02 (br s, 1H), 5.12 (s, 2H), 3.80-3.40 (m, 7H), 2.90-2.80 (m, 2H), 2.45-2.35 (m, 2H), 1.45 (s, 9H).

Step B—Synthesis of Compound Int-5b

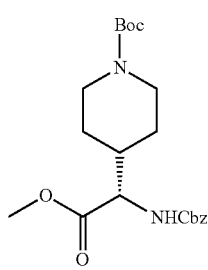

Int-5b

A solution of Compound Int-5a (1.30 g, 3.21 mmol) in methanol (90 mL) was purged with N$_2$, and to the resulting solution was added (−)-1,2-Bis((2S,5S)-2,5-dimethylphospholano)ethane (cyclooctadiene)rhodium(I) tetrafluoroborate (197 mg, 0.354 mmol) under N$_2$. The mixture was shaken under hydrogen atmosphere in a Parr shaker apparatus for 18 hours at 50 psi. After evacuating the hydrogen, the suspension was filtered and the filtrate was concentrated in vacuo to provide Compound Int-5b as a colorless oil (1.00 g, 77%). $^1$H NMR (CDCl$_3$) δ 7.40-7.30 (m, 5H), 5.35-5.25 (m, 1H), 5.10 (s, 2H), 4.40-4.35 (m, 1H), 4.20-4.10 (m, 2H), 3.70 (s, 3H), 2.70-2.55 (m, 2H), 2.00-1.90 (m, 1H), 1.65-1.40 (m, 11H), 1.30-1.20 (m, 2H).

Step C—Synthesis of Compound Int-5c

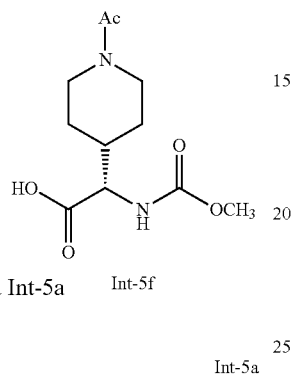

Int-5c

To a solution of 5% palladium on carbon (10% wet, 250 mg) in absolute ethanol (20 mL) under nitrogen was added Int-5b (1.00 g, 2.46 mmol). With stirring, the solution was placed under vacuum for 30 seconds and then was opened to a hydrogen gas balloon for 2 hours. After evacuating the hydrogen, the suspension was filtered through a Celite pad and the pad washed with ethanol (2×20 mL). The filtrate was concentrated in vacuo to provide Compound Int-5c as a colorless oil (670 mg, quant.). $^1$H NMR (CDCl$_3$) δ 4.21-4.08 (m, 2H), 3.73 (s, 3H), 3.31 (d, J=6.0 Hz, 1H), 2.75-2.57 (m, 2H), 1.84-1.70 (m, 1H), 1.68-1.56 (m, 1H), 1.45 (s, 9H), 1.45-1.20 (m, 5H).

Step D—Synthesis of Compound Int-5d

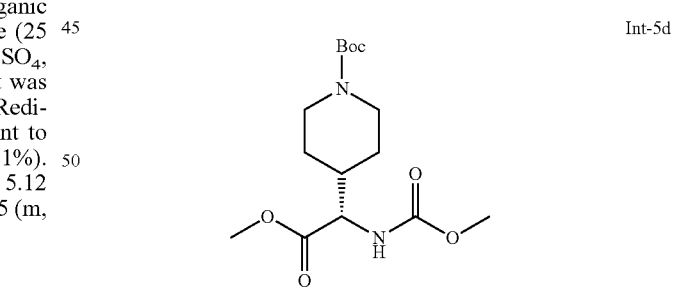

Int-5d

To a solution of Compound Int-5c (670 mg, 2.46 mmol) and triethylamine (0.520 mL, 3.73 mmol) in CH$_2$Cl$_2$ (10 mL) was added methyl chloroformate (0.210 mL, 2.72 mmol). The reaction mixture was allowed to stir at room temperature for about 15 hours. Water (20 mL) was added and the aqueous mixture was extracted with CH$_2$Cl$_2$ (2×15 mL). The combined organic layers were dried over Na$_2$SO$_4$, filtered and concentrated in vacuo. The crude product was purified using flash chromatography on an ISCO 24 g Redi-Sep column using 0-3% MeOH/CH$_2$Cl$_2$ as the eluent to provide an off-white solid (515 mg, 63%).

The off-white solid (300 mg, 0.908 mmol) was dissolved in a mixture of TFA (2 mL) and CH$_2$Cl$_2$ (10 mL) and the solution was allowed to stir at room temperature for 1 hour before it was concentrated in vacuo to provide a solid. To this residue was added a solution of triethylamine (0.760 mL, 5.45 mmol) in CH$_2$Cl$_2$ (10 mL), followed by acetic anhydride (0.086 mL, 0.915 mmol). The reaction mixture was allowed to stir at room temperature for about 15 hours then concentrated in vacuo. The crude product was purified using flash chromatography on an ISCO 12 g Redi-Sep column using 0-4% MeOH/CH$_2$Cl$_2$ as the eluent to provide Compound Int-5e as a colorless oil (247 mg, 99%). 1H NMR (CDCl$_3$) δ 5.27-5.21 (m, 1H), 4.73-4.62 (m, 1H), 4.42-4.32 (m, 1H), 3.69 (s, 3H), 3.18 (s, 3H), 3.18-3.09 (m, 1H), 3.07-2.95 (m, 1H), 2.55-2.41 (m, 1H), 2.07 (s, 3H), 1.78-1.49 (m, 3H), 1.38-1.21 (m, 2H).

Step E—Synthesis of Compound Int-5f

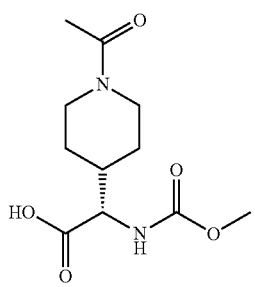

Int-5f

To a solution of Compound Int-5e (247 mg, 2.59 mmol) in THF (3 mL) was added lithium hydroxide monohydrate (77 mg, 1.83 mmol) in water (3 mL). The reaction mixture was allowed to stir at room temperature for about 15 hours then concentrated in vacuo to half volume. The aqueous mixture was then acidified with 1N HCl to pH 4 and extracted with EtOAc (7×15 mL). The combined organics were dried over Na$_2$SO$_4$, filtered and concentrated in vacuo to provide Compound Int-5f as an off-white solid (106 mg, 45%). NMR (CD$_3$OD) δ 5.52-5.43 (m, 1H), 4.71-4.62 (m, 1H), 4.44-4.31 (m, 1H), 3.91-3.81 (M, 1H), 3.70 (s, 3H), 3.12-2.99 (m, 1H), 2.58-2.46 (m, 1H), 2.10 (m, 4H), 1.86-1.54 (m, 2H), 1.50-1.21 (m, 3H).

Example 6

Preparation of Intermediate Compound Int-6a

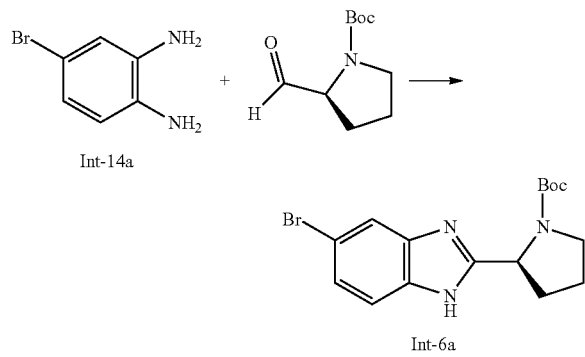

The mixture of Compound Int-14a (5.10 g, 27.3 mmol), (S)—N-Boc-prolinal (4.50 g, 22.6 mmol) in acetic acid (200 mL) at room temperature was added iodine (600 mg, 2.36 mmol) and the mixture was stirred and bubbled with air through a frit-glass bubbler for 7 hours. It was then concentrated in vacuo and the product was purified using silica gel flash column chromatography on silica gel to provide Compound Int-6a (4.37 g, 53%). LRMS: (M+H)$^+$=366.2, 368.2.

Example 7

Preparation of Intermediate Compound Int-7d

Step A—Synthesis of Compound Int-7b

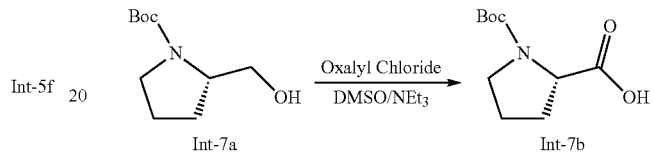

A 2 L, 3-necked round bottomed flask equipped with an overhead stirrer and a N$_2$ inlet was charged with a solution of oxalyl chloride (130 mL, 0.26 mol) in dichloromethane (250 mL). The solution was cooled to −78° C., and a solution of DMSO (20 mL, 0.28 mol) in dichloromethane (30 mL) was added dropwise. After 30 minutes, a solution of (S)—N-Boc-prolinol (40 g, 0.20 mol) in dichloromethane (200 mL) was added dropwise. After 30 minutes, triethylamine (140 mL, 1.00 mol) was added to the solution, and the flask was transferred to an ice/water bath and stirred for another 30 minutes. The reaction mixture was diluted with dichloromethane (200 mL) and washed successively with H$_2$O, 1M HCl, saturated NaHCO$_3$, and brine. The organic layer was dried over Na$_2$SO$_4$, filtered, and concentrated in vacuo to provide Compound Int-7c (40 g) as an oil, which was used without further purification.

Step B—Synthesis of Compound Int-7c

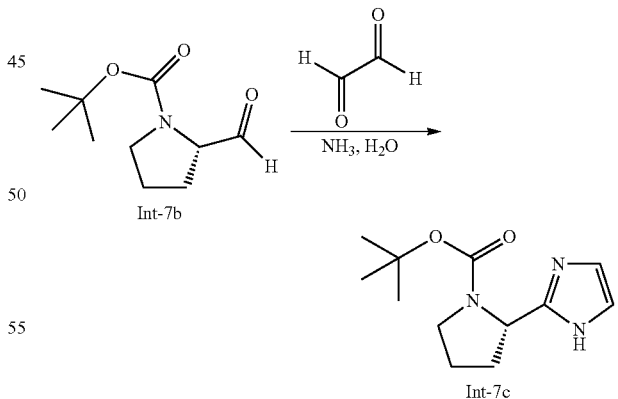

Glyoxal (2.0 mL of 40% in water) was added dropwise to a MeOH solution of NH$_4$OH (32 mL) and Compound Int-7b (8.564 g, 42.98 mmol, Aldrich over 5 min, an then the mixture was allowed to stir at ambient temperature for 19 hours. The reaction mixture was then concentrated in vacuo, and the residue purified further by a silica-gel flash chromatography (100% ethyl acetate eluent) followed by a recrystallization from ethyl acetate to provide 7c as a white fluffy solid (4.43 g). ¹H NMR (DMSO) δ: 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H).

Step C—Synthesis of Compound Int-7d

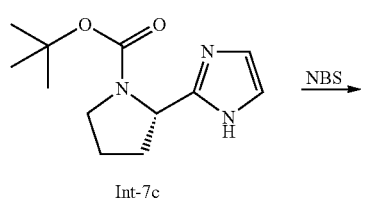

Int-7c

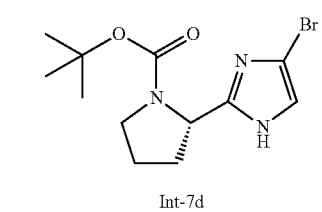

Int-7d

N-Bromo succinimide (838.4 mg, 4.71 mmol) was added in portions over 15 minutes to a cooled (ice/water) CH₂Cl₂ (20 mL) solution of Compound Int-7c (1.06 g, 4.50 mmol). The reaction mixture was stirred for 75 minutes and concentrated in vacuo to an oil. The crude product was purified using silica-gel RPLC (Acetonitrile/water/0.1% TFA) to separate the mono bromide from its dibromo analog (over bromination) and the starting material. The RPLC elute was neutralized with excess NH₃/MeOH, and the volatile component was removed in vacuo. The residue was partitioned between CH₂Cl₂ and water, and the aqueous layer was extracted with water. The combined organic phase was dried (MgSO₄), filtered, and concentrated in vacuo to provide Compound Int-7d as a white solid (374 mg). ¹H NMR (DMSO) δ: 12.12 (br s, 1H), 7.10 (m, 1H), 4.70 (m, 1H), 3.31 (m, 1H; overlapped with water signal), 2.25-1.73 (m, 4H), 1.39/1.17 (s, 3.8H+5.2H).

Alternative Synthesis of Compound Int-7d
Step D—Synthesis of Compound Int-7e

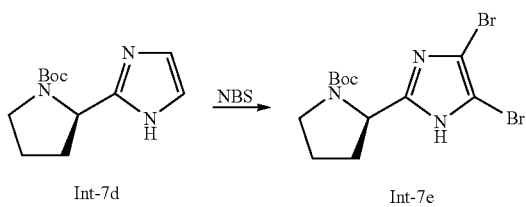

To a suspension of Int-7b (140 g, 0.59 mol) in THF (2000 ml) was added N-bromosuccinimide (200 g, 1.1 mol). The mixture was allowed to stir at ambient temperature under N₂ gas for about 15 hours. The solvent was then removed in vacuo, and the resulting residue was purified using silica-gel chromatography (ethyl acetate eluent) to provide 230 g of Compound Int-7e. MS (ESI) m/e (M+H⁺): 396.

Step E Synthesis of Compound Int-7d

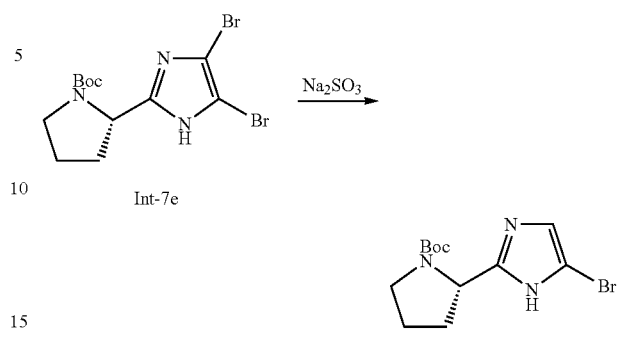

To a suspension of Int-7e (230 g, 0.58 mol) in ethanol/H₂O (1:1 ratio, 3000 ml) was added Na₂SO₃ (733 g, 5.8 mol). The resulting mixture was allowed to stir at mild reflux for about 15 hours. After cooling to room temperature, the mixture was extracted with dichloromethane twice and the combined organic layers was concentrated in vacuo to a semi-solid. The resulting residue was purified using chromatography on silica gel to provide Compound Int-7d. MS (ESI) m/e (M+H⁺): 317.

Example 8

Preparation of Intermediate Compound Int-8g

Step A—Synthesis of Compound Int-8b

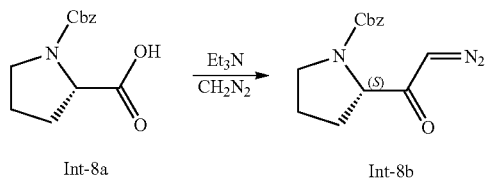

To a solution of CBz-proline (Int-8a, 50 g, 0.2 mol) in THF (500 mL) and Et₃N (20 mL) was added dropwise isopropyl chloroformate (25 g, 0.22 mol) at ice water bath. Then the resulting solution was allowed to warm to room temperature and stirred for 1 hour, then a solution of CH₂N₂ (0.22 mol) in ether was added slowly until N₂ gas evolution stopped. Acetic acid (4 mL) was added and the reaction mixture was stirred for 10 minutes. NaHCO₃ solution was then added and the reaction mixture extracted three times with ethyl acetate. The organic layers were combined, dried over Na₂SO₄, filtered and concentrated in vacuo to provide crude product. The crude product was then purified using column chromatography on silica gel (Pet Ether:E.Acetate=3:1) to provide Compound Int-8b (38 g, 70% yield).

Step B—Synthesis of Compound Int-8c

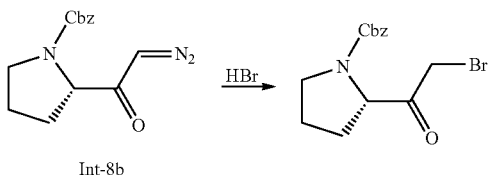

To a solution of Compound Int-8b (38 g, 0.14 mol) in acetic acid (20 mL) was added dropwise an aqueous HBr solution (11.2 g, 0.14 mol). After 10 min, the mixture was poured into an aqueous NaHCO₃ solution and extracted three times with ethyl acetate. The combined organic layers were washed with brine then water, dried over Na₂SO₄, filtered and concentrated in vacuo to provide Compound Int-8c (30 g, 68% yield).

Step C—Synthesis of Compound Int-8e

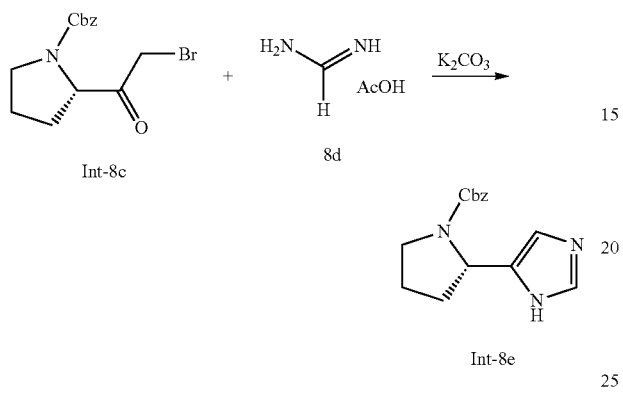

To a solution of Compound Int-8c (10 g, 32 mmol) and compound 8d (8.4 g, 64 mmol) in DMF (70 mL) was added K₂CO₃ (18 g, 126 mmol). The mixture was allowed to stir at 100° C. in a sealed tube for about 15 hours. The solvent was removed and the residue obtained was purified using column chromatography on silica gel (dichloromethane: MeOH=20:1) to provide Compound Int-8e. (6 g, 59% yield).

Step D—Synthesis of Compound Int-8f

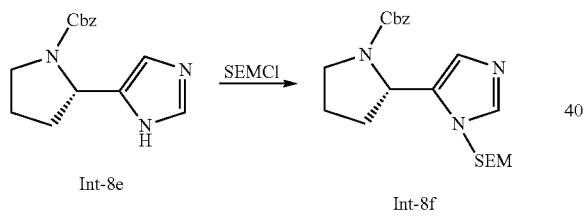

To a solution Int-8e (4 g, 14.7 mmol) in THF (40 mL) was added NaH (6.6 g, 60% content, 16.17 mmol) at 0° C. The mixture was allowed to stir at room temperature for 30 minutes and then cooled to 0° C., and SEMCl (2.4 g, 14.7 mmol) added dropwise. The resulting mixture was allowed to stir at 0° C. for 2 hours. The solvent was removed under vacuum and the resulting residue was purified using column chromatography on silica gel (dichloromethane: MeOH=20:1) to provide Compound Int-8f. (2 g, 34% yield)

Step E—Synthesis of Compound Int-8g

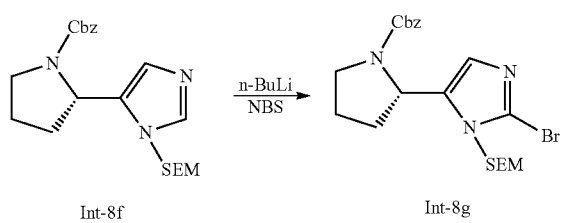

To a solution of Compound Int-8f (2 g, 5 mmol) in THF (20 mL) was added dropwise n-butyllithium (2.5 mL, 6.3 mmol) at −78° C. (bath) under N₂ protection. The resulting solution was allowed to stir at this temperature for 30 minutes. Then a solution of NBS (0.89 g, 5 mmol) in THF (10 mL) was added dropwise at −78° C. The mixture was allowed to stir at −78° C. for 1 hour and then aqueous NH₄Cl solution was added. The organic layer was separated and concentrated in vacuo off to provide a crude residue, which was purified using column chromatography on silica gel (PE:EA=3:1 as the eluent) to provide Compound Int-8g (400 mg, 16.5%).

Example 9

Preparation of Intermediate Compound Int-9e

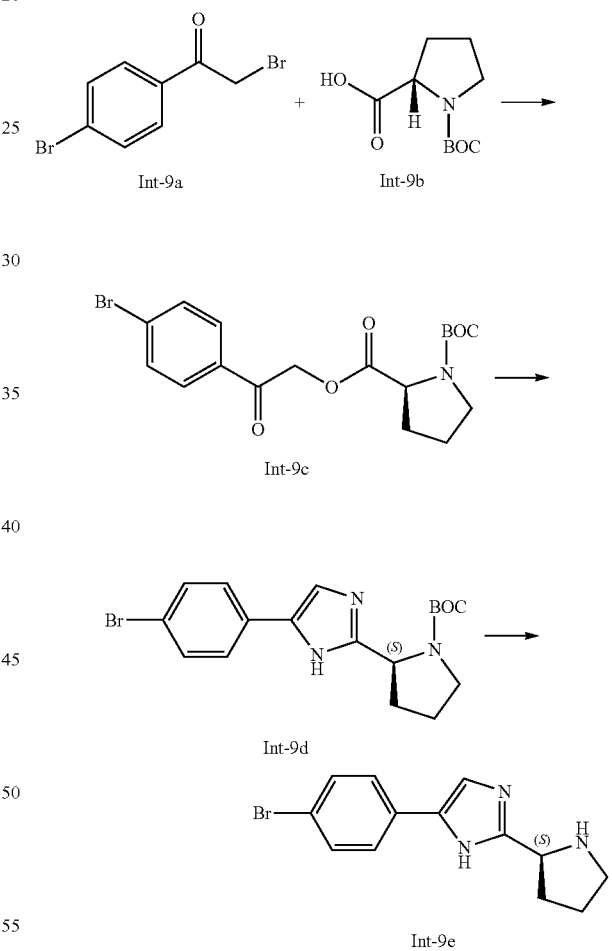

Step A—Synthesis of Compound Int-9c

A mixture of compound Int-9a (50.0 g, 179.9 mmol), compound Int-9b (43.0 g, 199.8 mmol), and triethylamine (30 mL, 215.5 mmol) in DMF (100 mL) was allowed to stir at room temperature for about 4 days. Ethyl acetate (600 mL) was then added to the reaction mixture and the resulting solution was washed with brine (3×100 mL), dried over sodium sulfate, filtered and concentrated in vacuo to provide Compound Int-9c as a brown gel (74.5 g, ~100%), which was used without further purification.

Step B—Synthesis of Compound Int-9d

Compound Int-9c (20 g, crude, ~48.5 mmol), ammonium acetate (20.0 g, 256.6 mmol), and o-xylene (100 mL) were added to a 500 mL pressure vessel. The resulting mixture was allowed to stir at 140° C. for 2.5 hours, then cooled to room temperature and concentrated in vacuo. The resulting residue was taken up in ethyl acetate (400 mL), washed with saturated sodium carbonate solution, dried over sodium sulfate, filtered and concentrated in vacuo. The residue obtained was purified using a 330 g ISCO silica column/Combi-Flash system (20-50% ethyl acetate in hexanes) to provide Compound Int-9d as an orange solid (15.5 g, 81%).

Step C—Synthesis of Compound Int-9e

A solution of compound Int-9d (4.0 g, 10.2 mmol), trifluoroacetic acid (10 mL, 130.6 mmol), and dichloromethane (10 mL) was allowed to stir at room temperature for about 15 hours, then was concentrated in vacuo. The residue obtained was taken up in dichloromethane (60 mL), washed with saturated sodium carbonate, dried over sodium sulfate, filtered and concentrated in vacuo to provide Compound Int-9e as an off-white solid (3 g, ~100%), which was used without further purification.

Int-9f was prepared from N-BOC-trans-fluoro-L-proline (commercially available) using the method described above.

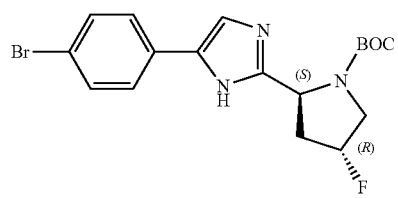

Int-9f

Int-9g was prepared from N-Boc-4,4-difluoro-L-proline (commercially available) using the method described above.

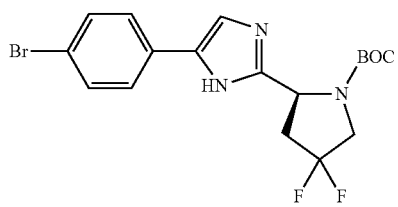

Int-9g

Int-9h was prepared from BOC-HYP-OH, (commercially available) using the method described above.

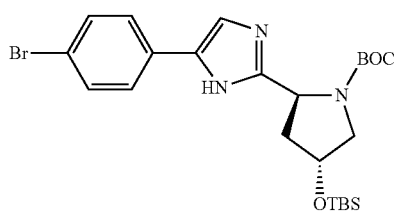

Int-9h

Int-9i was prepared from 2S-carboxy piperidine (prepared using the method described in Gudasheva, et al., *J. Med. Chem. Ther.* 1996, 31, 151) using the method described above.

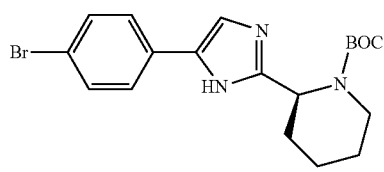

Int-9i

Int-9j was prepared from 2S-carboxy 4,4-F piperidine (prepared according to the method described in Chinese Patent CN 101462999) using the method described above.

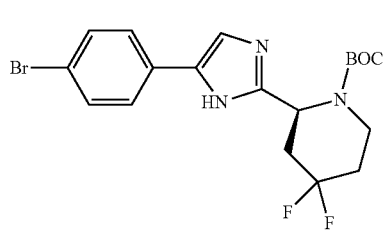

Int-9j

Int-9k was prepared from 2S-carboxy morpholine, using the method described above.

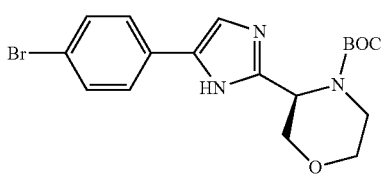

Int-9k

Int-9l was prepared from (1R,3S,4S)—N-BOC-2-azabicyclo[2.2.1]-heptane-3-carboxylic acid (commercially available), using the method described above.

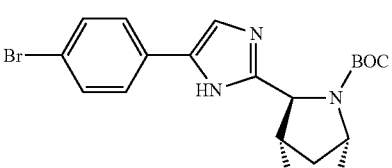

Int-9l

Int-9m was prepared from 2(S)-azabicyclo[2.2.2]-octane-2,3-dicarboxylic acid 2-tert-butyl ester (commercially available) using the method described above.

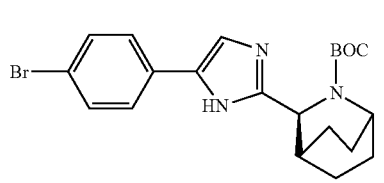

Int-9m

Example 10

Preparation of Intermediate Compound Int-10c

Int-10c

Step A—Synthesis of Compound Int-10a

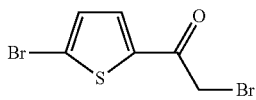
Int-10a

To a solution of 2-acetyl-5-bromothiophene (10.0 g, 48.8 mmol) in anhydrous $CH_2Cl_2$ (120 mL) at room temperature was added bromine (7.79 g, 48.8 mmol). The resulting reaction was allowed to stir at room temperature for 20 hours, then was concentrated in vacuo to provide Compound Int-10a as a yellow solid (14.0 g, quant.), which was used without further purification.

Step B—Synthesis of Compound Int-10b

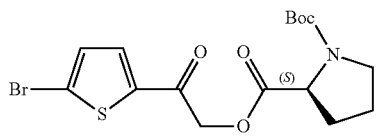
Int-10b

To a solution of Compound Int-10a (13.9 g, 48.8 mmol) and N-Boc-proline (22.1 g, 103 mmol) in anhydrous acetonitrile (250 mL) at room temperature was added diisopropylethyl amine (18.0 mL, 101 mmol). The reaction was allowed to stir at room temperature for 16 hours, then EtOAc (500 mL) and water (500 mL) were added and the layers were separated. The organic solution was washed with saturated aqueous sodium bicarbonate solution (500 mL), dried over $MgSO_4$, filtered and concentrated in vacuo to provide Compound Int-10b (21.2 g, quant.), which was used without further purification.

Step C—Synthesis of Compound Int-10c

A suspension of Int-10b (11.7 g, 28.0 mmol) and $NH_4OAc$ (43 g, 559 mmol) in anhydrous toluene (200 mL) was heated to 100° C. and allowed to stir at this temperature for 12 hours. The reaction mixture was then cooled to room temperature, and EtOAc (500 mL) and water (500 mL) were added. The layers were separated and the aqueous layer was extracted with EtOAc (2×200 mL). The combined organics were dried over $MgSO_4$, filtered and concentrated in vacuo and the residue obtained was purified using flash chromatography on an ISCO 330 g Redi-Sep column (10-80% EtOAc/hexanes as eluent) to provide Compound Int-10c (6.18 g, 56%). LRMS: $(M+H)^+=398.1, 400.1$.

Example 11

Preparation of Intermediate Compound Int-11f

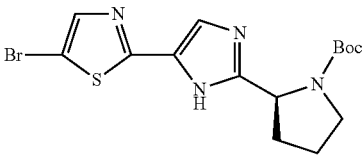
Int-11f

Step A—Synthesis of Compound Int-11a

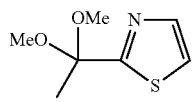
Int-11a

To a solution of 2-acetylthiazole (10.0 g, 78.6 mmol) in anhydrous MeOH (150 mL) at room temperature was added trimethyl orthoformate (52.0 g, 488 mmol) and p-toluenesulfonic acid (14.2 g, 74.7 mmol). The resulting reaction was heated to 50° C. and was allowed to stir at this temperature for 12 hours. EtOAc (600 mL) was then added and the resulting solution was washed with saturated aqueous sodium bicarbonate solution (600 mL) and brine (600 mL). The organic layer was dried over $MgSO_4$, filtered and concentrated in vacuo to provide Compound Int-11a (12.1 g, 90%), which was used without further purification.

Step B—Synthesis of Compound Int-11b

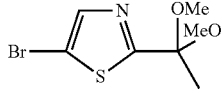
Int-11b

To a solution of Compound Int-11a (8.0 g, 46.2 mmol) in anhydrous THF (150 mL) at −78° C. under nitrogen was added n-butyllithium (23.1 mL, 2.0 M, 46.2 mmol) over 10 minutes. The reaction mixture was allowed to stir at −78° C. for 45 minutes, then a solution of carbon tetrabromide (15.9 g, 48.0 mmol) in anhydrous THF (50 mL) was added dropwise over 10 minutes. The cooling bath was removed and the reaction mixture was then allowed to warm to 0° C. on its own. The reaction mixture was then quenched with saturated ammonium chloride solution (50 mL). The reaction mixture was then diluted with water (150 mL) and diethyl ether (150 mL) and separated. The organic phase was washed with brine (200 mL), dried over $MgSO_4$, filtered and concentrated in vacuo. The residue obtained was purified using flash chromatography on an ISCO 330 g Redi-Sep column (0-20% EtOAc/hexanes as eluent) to provide Compound Int-11b (7.47 g, 65%).

Step C—Synthesis of Compound Int-11c

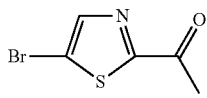

Int-11c

To a solution of Compound Int-11b (7.47 g, 29.6 mmol) in anhydrous CH$_2$Cl$_2$ (100 mL) at room temperature was added TFA (64 mL) and water (2.0 mL). The resulting reaction was allowed to stir at room temperature for 17 hours, and then was concentrated in vacuo. The residue obtained was taken up in diethyl ether (300 mL) and 10% aqueous NaHCO$_3$ solution (300 mL) and separated. The organic phase was washed with water and brine, dried over MgSO$_4$, filtered and concentrated in vacuo to provide Compound Int-11c (5.63 g, 92%), which was used without further purification.

Step D—Synthesis of Compound Int-11d

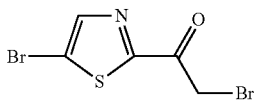

Int-11d

To a solution of 2-acetyl-5-bromothiazole (5.63 g, 27.3 mmol) in anhydrous CH$_2$Cl$_2$ (100 mL) at room temperature was added bromine (4.39 g, 27.3 mmol). The reaction mixture was allowed to stir at room temperature for about 48 hours, then was concentrated in vacuo to provide Compound Int-11d as a yellow solid (8.63 g, quant.), which was used without further purification.

Step E—Synthesis of Compound Int-11e

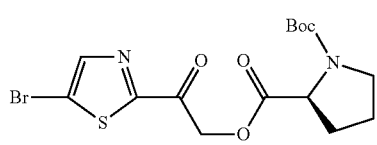

Int-11e

Compound Int-11e was prepared from compound Int-11d using the method described in Example 3, Step B.

Step F—Synthesis of Compound Int-11f

Compound Int-11f was prepared from compound Int-11e using the method described in Example 8, Step C. LRMS: (M+H)$^+$=399.0, 401.0.

Example 12

Preparation of Intermediate Compound Int-12d

Step A—Synthesis of Compound Int-12b

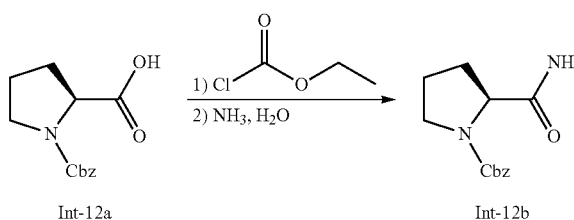

Ethyl chloroformate (12 mL, 125 mmol) in 180 mL of THF was added drop-wise to a cooled solution (−5° C.) of compound Z-Pro-OH (Int-12a, 13.8 g, 55.5 mmol), TEA (7.71 mL, 55.5 mmol). The resulting slurry was stirred for 20 minutes at −5° C. before saturated NH$_4$OH (15 mL) was added. The solution was allowed to stir at room temperature for 18 hours, volatiles were removed, and the resulting residue was taken up in EtOAc (180 mL). The undissolved white precipitate was filtered off and rinsed with EtOAc (100 mL). The organic layers were dried over Na$_2$SO$_4$, filtered and concentrated in vacuo to provide Compound Int-12b (13.5 g) as off-white amorphous solid. MS (ESI) m/e (M+H$^+$): 249.

Step B—Synthesis of Compound Int-12c

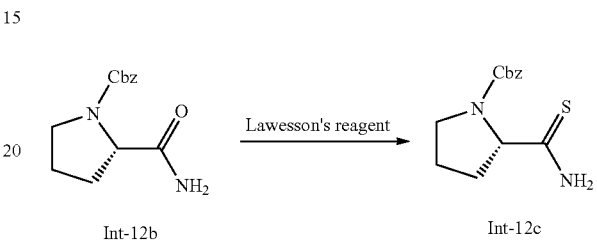

Lawesson's reagent (16.1 g, 39.9 mmol) was added to a stirred slurry of Compound Int-12b (18 g, 72.6 mmol) in toluene (200 mL) at room temperature. The reaction mixture was heated to 100° C. for 3 hours before the solvent was removed. The residue was purified using flash column chromatography on silica gel (dichloromethane/MeOH=1:0-20:1) to provide Compound Int-12c (18 g). MS (ESI) m/e (M+H$^+$): 265.

Step C—Synthesis of Compound Int-12d

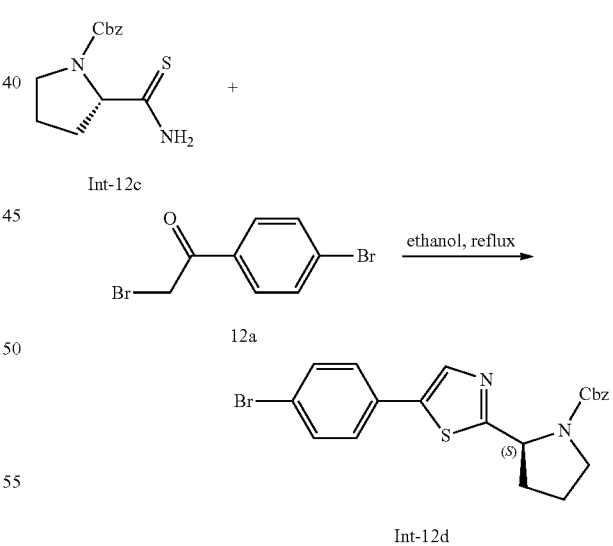

A mixture of Compound Int-12c (10.0 g, 37.8 mmol) and the bromoacetophenone (12a, 10.0 g, 35.9 mmol) in ethanol (100 mL) was heated at 90° C. for 150 minutes. The reaction mixture was cooled and concentrated in vacuo, and the resulting residue was purified using SiO$_2$ chromatography to provide Compound Int-12d (11 g). MS (ESI) m/e (M+H$^+$): 444.

Example 13

Preparation of Intermediate Compound Int-13b

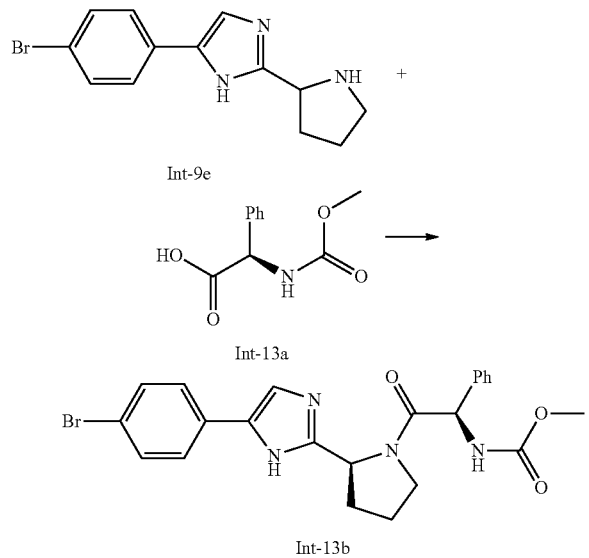

A solution of compound Int-9e (1.0 g, 3.42 mmol), compound Int-13a (0.95 g, 4.54 mmol), HATU (1.3 g, 3.42 mmol), and DMF (10 mL) was allowed to stir at room temperature for about 15 hours. The solution was then diluted with ethyl acetate (100 mL), washed with brine (3×40 mL), dried over sodium sulfate, filtered and concentrated in vacuo. The resulting residue was purified using an 80 g silica gel column/Combi-Flash system (0-5% methanol in dichloromethane) to provide Compound Int-13b as a gel (1.12 g, 68%).

Example 14

Preparation of Intermediate Compound Int-14c

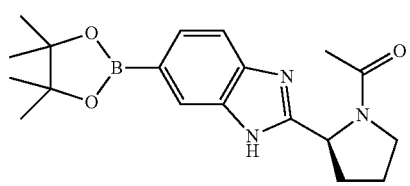

Step A—Synthesis of Compound Int-14b

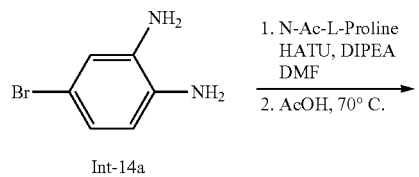

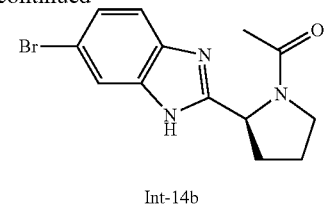

To a solution of diamino benzene Int-14a (6.1 g, 32.7 mmol), N-acetyl-L-proline (5.4 g, 34.35 mmol) and HATU (13.7 g, 34.35 mmol) in anhydrous DMF (100 mL) was added DIPEA (16.91 mL, 96.9 mmol) dropwise over 15 minutes at ice temperature. The reaction was warmed to room temperature and allowed to stir for 3 hours. The reaction was then diluted with EtOAc (500 mL) and the organic layer washed with water (200 mL×2). The aqueous layer was back-extracted with EtOAc (100 mL×2). The combined organic layers were washed with brine, dried over $MgSO_4$, filtered and concentrated in vacuo. The crude product was purified using flash chromatography using 1%-2% $MeOH/CH_2Cl_2$ as eluent to provide the intermediate amide (4.1 g). The amide was dissolved in glacial acetic acid and was heated at 60-70° C. for 1 hour. The reaction mixture was diluted with EtOAc (100 mL) and cooled in ice bath. Saturated $Na_2CO_3$ solution was added slowly until the solution was at pH 8.0. The organic layer was separated and the aqueous layer was extracted with EtOAc (250 mL×2). The combined organic layers were washed with water and brine, dried over $MgSO_4$, filtered and concentrated in vacuo to provide Compound Int-14b (3.75 g, 38%). LCMS: $M^+$=308

Step B—Synthesis of Compound Int-14c

Compound Int-14b (925 mg, 3 mmol), $(Pinacol)_2B_2$ (1.6 g, 6.3 mmol), $Pd(PPh_3)_4$ (174 mg, 0.15 mmol), potassium acetate (736 mg, 7.5 mmol) and 1,4-dioxane (100 mL) were added to a 350 mL pressure vessel. The resulting mixture was degassed, purged with nitrogen and allowed to stir at 80° C. for 17 hours. After the reaction was cooled to room temperature the solution was diluted with $CH_2Cl_2$ (300 mL) and filtered through a celite plug. The filtrate was washed with $NaHCO_3$ solution (50 mL) and water (50 mL). The combined organic layers were washed with brine, dried over $MgSO_4$, filtered and concentrated in vacuo. The crude product was purified using flash chromatography using a 0-5% MeOH/$CH_2Cl_2$ as eluent to provide Compound Int-14c (750 mg, 70%, contains some pinacol). MS: $MH^+$=356.2; $^1H$ NMR (500 MHz, $CD_3OD$): δ 8.1-7.4 (m, 3H), 5.3 (m, 1H), 3.9 (m, 1H), 3.7 (m, 1H), 2.4 (m, 1H), 2.0-2.2 (m, 6H), 1.39 (bs, 12H).

Example 15

Preparation of Intermediate Compound Int-15c

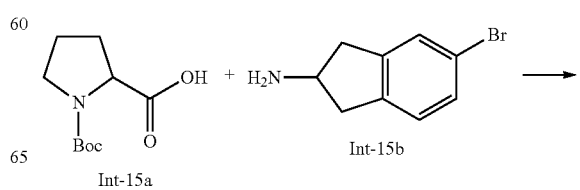

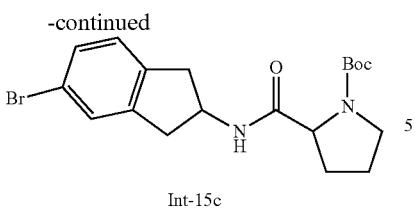

Int-15c

To a solution of Boc-L-proline (Int-15a, 147 mg, 0.68 mmol) in 4.3 mL of DMF was added amine Int-15b (200 mg, 0.68 mmol), EDCI (163 mg, 0.85 mmol), HOBT (115 mg, 0.85 mmol), and diisopropylethylamine (0.24 mL, 1.36 mmol). The resulting reaction was heated at 85° C. and allowed to stir at this temperature for 16 hours. The reaction mixture was cooled to room temperature and was then partitioned between EtOAc and water. The organic phase was separated and the aqueous phase was further extracted with EtOAc. The combined organic phases were dried (MgSO$_4$), filtered and concentrated in vacuo to provide a crude residue which was purified using by column chromatography (EtOAc/Hex, 0 to 50% EtOAc eluent) to provide Compound Int-15c (280 mg, 100%). LC/MS m/z found 409.2 (M$^+$+H).

Example 16

Preparation of Intermediate Compound Int-16b

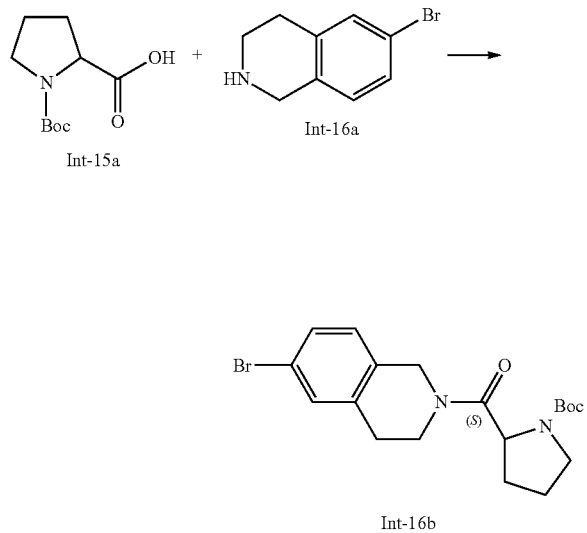

To a solution of Boc-L-proline (Int-15a, 406 mg, 1.88 mmol) in 10 mL of DMF was added amine Int-16a (400 mg, 1.88 mmol), EDCI (450 mg, 2.35 mmol), HOBT (317 mg, 2.35 mmol), and diisopropylethylamine (0.65 mL, 3.76 mmol). The resulting reaction was heated at 85° C. and allowed to stir at this temperature for 16 hours. The reaction mixture was cooled to room temperature and was then partitioned between EtOAc and water. The organic phase was separated and the aqueous phase was further extracted with EtOAc. The combined organic phases were dried (MgSO$_4$), filtered and concentrated in vacuo to provide a crude residue which was purified using (ISCO) flash column chromatography (EtOAc/Hex, 0 to 50% EtOAc eluent) to provide Compound Int-16b (680 mg, 88%).

Example 17

Preparation of Intermediate Compound Int-17d

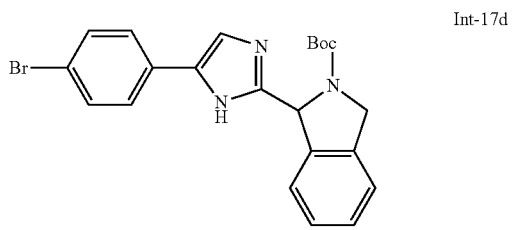 [SMILES: CC(C)(C)OC(=O)N1Cc2ccccc2C1c1ncc(-c2ccc(Br)cc2)[nH]1]

Int-17d

Step A—Synthesis of Compound Int-17c

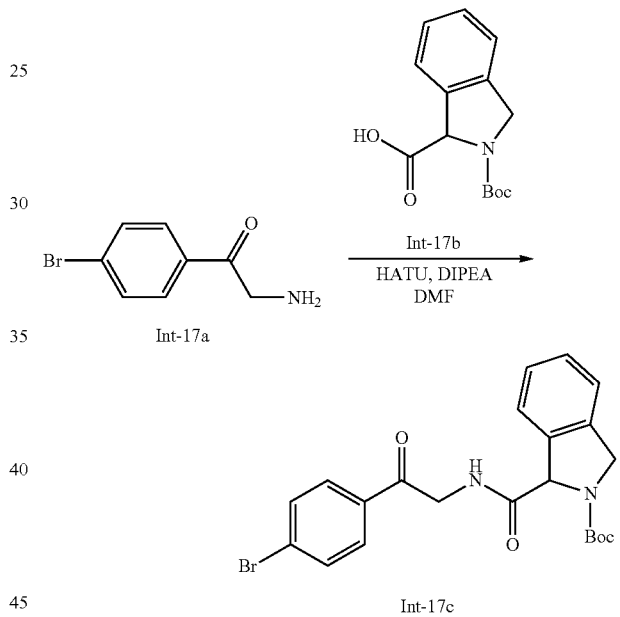

A solution of compound Int-17a (0.50 g 2.0 mmol), compound Int-17b (0.58 g 2.2 mmol) and HATU (0.85 g 2.2 mmol) in 10 mL DMF was cooled to 0° C. and allowed to stir at this temperature for 3 minutes. Diisopropylethylamine (1 mL) was added dropwise over 5 minutes to the reaction mixture and the resulting reaction was allowed to warm to room temperature and stir at this temperature for 48 hours. The reaction mixture was then diluted with 250 mL ethyl acetate and the organic phase was collected, washed with water (100 mL), brine, dried over sodium sulfate, filtered and concentrated in vacuo. The residue obtained was purified using flash liquid chromatography (0% to 100% EtOAc/Hexane) to provide Compound Int-17c (0.9 g, theory 0.9 g).

Step B—Synthesis of Compound Int-17d

A solution of Compound Int-17c (0.9 g, 2.0 mmol) NH$_4$OAc (40.0 mmol) and O-xylene (20 mL) was put in a 75 mL pressure flask and the resulting solution was heated to 140° C. and allowed to stir at this temperature for 16 hours. The reaction mixture was allowed to cool to room temperature, then was diluted with 150 mL ethyl acetate. The resulting solution was transferred to a separatory funnel and the organic phase was collected, washed with water (100 mL), brine, dried over sodium sulfate, filtered and concentrated in vacuo. The resulting residue was purified using flash liquid chromatography (0% to 100% EtOAc/Hexane) to provide Compound Int-17d (0.42 g, theory 0.86 g). FABMS: MH$^+$=440

Example 18

Preparation of Intermediate Compound Int-18b

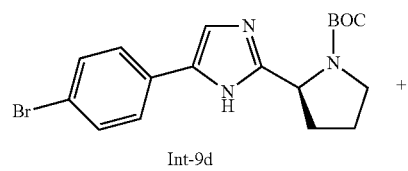

Int-9d

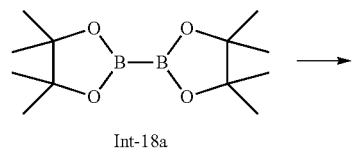

Int-18a

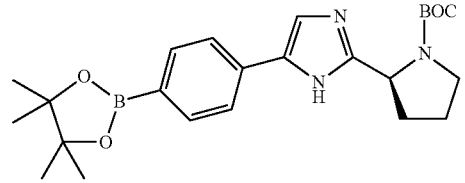

Int-18b

Compound Int-9d (4.2 g, 12.24 mmol), compound Int-18a (Pinacol diborane, 6.5 g, 25.6 mmol), Pd(PPh$_3$)$_4$ (0.563 g, 0.49 mmol), potassium acetate (3.1 g, 31.58 mmol) and 1,4-dioxane (100 mL) were added to a 350 mL pressure vessel. The resulting mixture was degassed and allowed to stir at 80° C. for 20 hours. After the reaction was cooled to room temperature and filtered, the filtrate was concentrated in vacuo and purified using flash column chromatography on silica gel column (0-2% methanol in dichloromethane) to provide Compound Int-18b as a white wax (2.5 g, 46.5%).

Synthesis of intermediate Compound Int-18c:

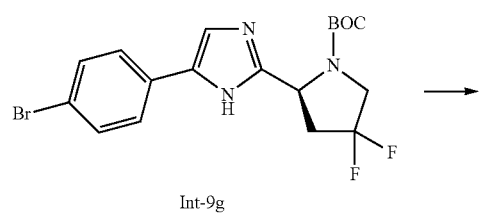

Int-9g

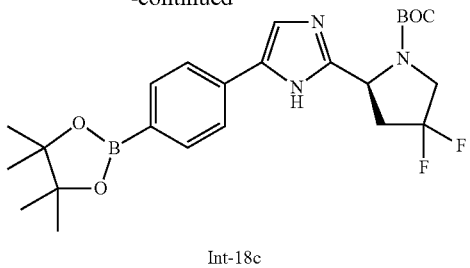

Int-18c

Compound Int-9g (5.7 g, 13.31 mmol), bis(pinacolaton) diboron (6.8 g, 26.78 mmol), tetrakis(triphenylphosphine) palladium (0) (0.76 g, 0.66 mmol), potassium acetate (2.0 g, 20.37 mmol) were added to a 500 ml flask. The resulting suspension was degassed and stirred at 80° C. for about 15 hours, then the reaction mixture was cooled to room temperature and filtered. The filtrate was concentrated in vacuo and purified using a 220 g ISCO silica column on Combi-Flash Rf (0-4% methanol in dichloromethane) to provide Compound Int-18c as a wax (5.4 g, 85%).

Intermediate Compounds Int-18f, 18h, 18l, 18m (depicted below) were prepared using this methodology from Compounds Int-9f, Int-9h, Int-9l, and Int-9m respectively.

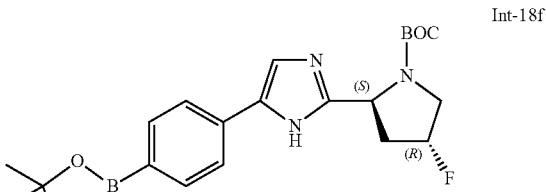

Int-18f

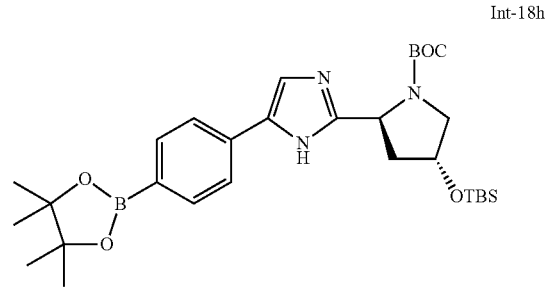

Int-18h

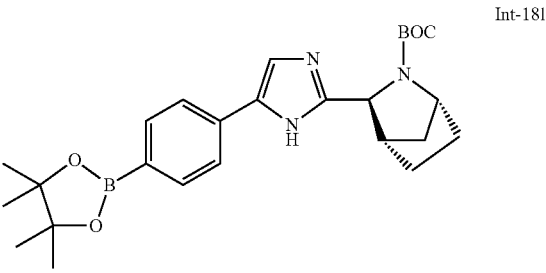

Int-18l

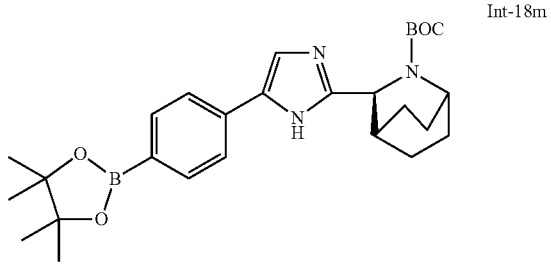

Example 19

Preparation of Intermediate Compound Int-19b

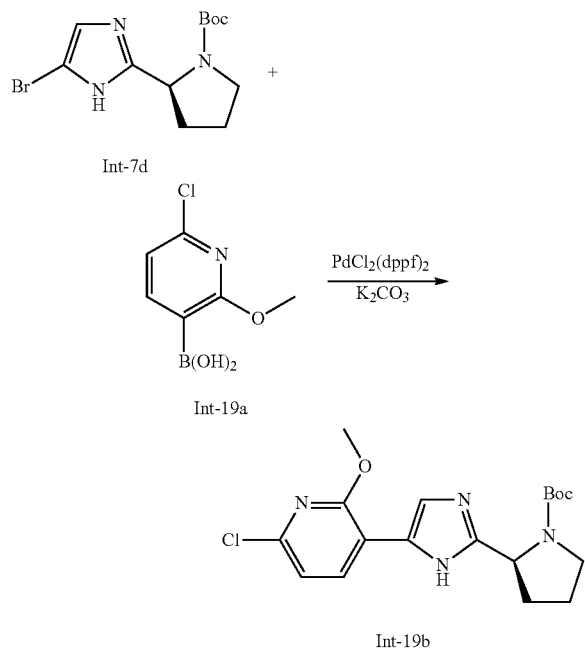

To a solution of Compound Int-7d (0.5 g, 1.58 mmol) in DME (15 mL) at room temperature under N₂ was added PdCl₂(dppf)₂ (258 mg, 0.30 mmol). The reaction mixture was allowed to stir at 100° C. for 5 minutes, then a solution of compound Int-19a (592 mg, 3.16 mmol) and K₂CO₃ (654 mg, 4.74 mmol) in 15 mL H₂O was added to the reaction mixture in 3 portions over 10 minutes. The resulting reaction was allowed to stir for an additional 30 minutes, after which time thin-layer chromatography analysis indicated consumption of compound Int-7a. The reaction was allowed to stir for an additional 30 minutes, then was concentrated in vacuo, and the residue obtained was taken up in 150 mL ethyl acetate. The organic phase was separated, washed with water (50 mL), brine and dried over sodium sulfate. After filtration, the organic layer was concentrated in vacuo and the resulting residue was purified using flash liquid chromatography (0% to 100% EtOAc/Hexane) to provide 600 mg of compound Int-19b (>85% purity, theory 597 mg). HPLC (C18 column Gemini 5u 110A, 150×21.2 mm, 5 micron). FABMS: MH⁺=379

Example 20

Preparation of Intermediate Compound Int-20c

Step A—Synthesis of Compound Int-20a

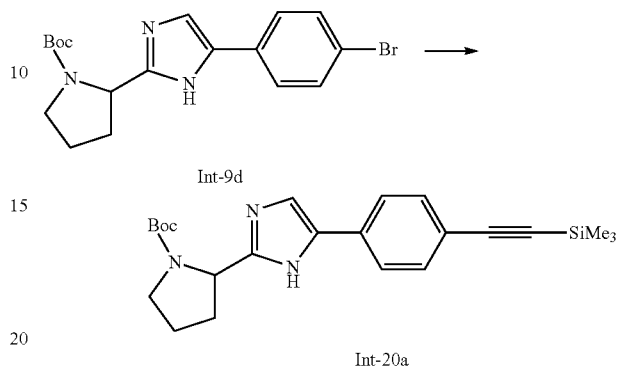

To a solution of Int-9d (3.30 g, 8.41 mmol), (trimethylsilyl)acetylene (7.0 mL, 50.5 mmol), PdCl₂(PPh₃)₂ (0.60 g, 0.84 mmol), copper (I) iodide (0.48 g, 2.52 mmol) and tetrabutylammonium iodide (3.73 g, 10.1 mmol) in anhydrous DMF (100 mL) at room temperature was added triethylamine (8.51 mL, 84.1 mmol) in a glass pressure vessel. The pressure vessel was then tightly capped and heated to 70° C. After 18 hours, the reaction was cooled to room temperature, the mixture was diluted with EtOAc (200 mL), THF (200 mL) and water (300 mL). The layers were separated. The aqueous solution was extracted with EtOAc (200 mL). The combined organic layers were washed with 1:1 mixture of water and saturated aqueous sodium bicarbonate solution (2×500 mL), dried over MgSO₄, filtered and concentrated in vacuo. The residue obtained was purified using flash column chromatography on silica gel to provide Compound Int-20a (2.10 g, 61%). LRMS: (M+H)⁺=410.4.

Step B—Synthesis of Compound Int-20b

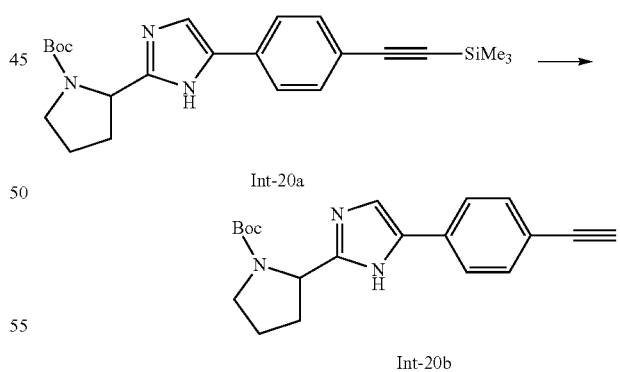

To a solution of Compound Int-20a (2.00 g, 4.88 mmol) in methanol (70 mL) at room temperature was added K₂CO₃ (1.70 g, 12.2 mmol). The reaction mixture was allowed to stir at room temperature for 18 hours before it was concentrated in vacuo. The residue was dissolved with EtOAc (100 mL), THF (100 mL) and water (150 mL). The layers were separated. The aqueous solution was extracted with EtOAc (100 mL). The combined organic solution was dried over MgSO₄, filtered and concentrated in vacuo. The product was purified using silica gel flash column chromatography on silica gel to provide Compound Int-20b (1.18 g, 72%). LRMS: (M+H)+=338.3.

Step C—Synthesis of Compound Int-20c

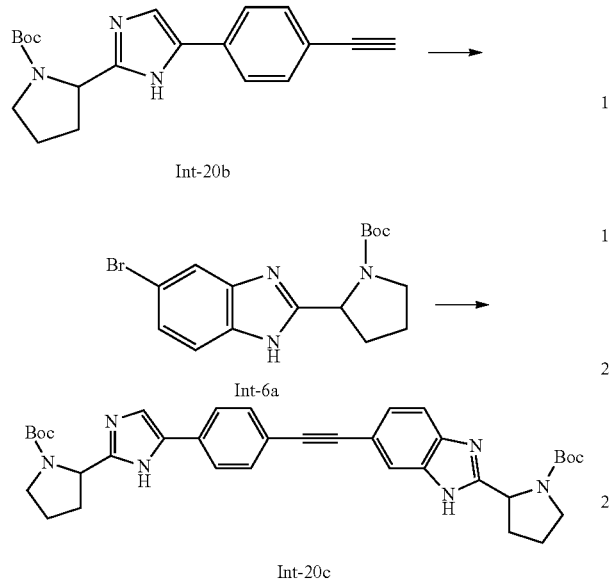

To a solution of Compound Int-20b (0.700 g, 2.07 mmol), Compound Int-6a (1.00 mL, 2.70 mmol), PdCl$_2$(PPh$_3$)$_2$ (0.146 g, 0.21 mmol), copper (I) iodide (80 mg, 0.41 mmol) and tetrabutylammonium iodide (0.92 g, 2.50 mmol) in anhydrous DMF (30 mL) at room temperature was added triethylamine (2.1 mL, 20.7 mmol). The mixture was then heated at 85° C. (oil bath) for 18 hours. After cooled to room temperature, the mixture was diluted with EtOAc (100 mL), THF (100 mL) and water (150 mL). The layers were separated. The aqueous solution was extracted with EtOAc (100 mL). The combined organic solution was washed with 1:1 mixture of water and saturated aqueous sodium bicarbonate solution (2×200 mL), dried over MgSO$_4$, filtered and concentrated in vacuo. The resulting residue was purified using silica gel flash column chromatography on silica gel to provide Compound Int-20c (10 mg, 1%). LRMS: (M+H)+=623.5.

Example 21

Preparation of Intermediate Compound Int-21a

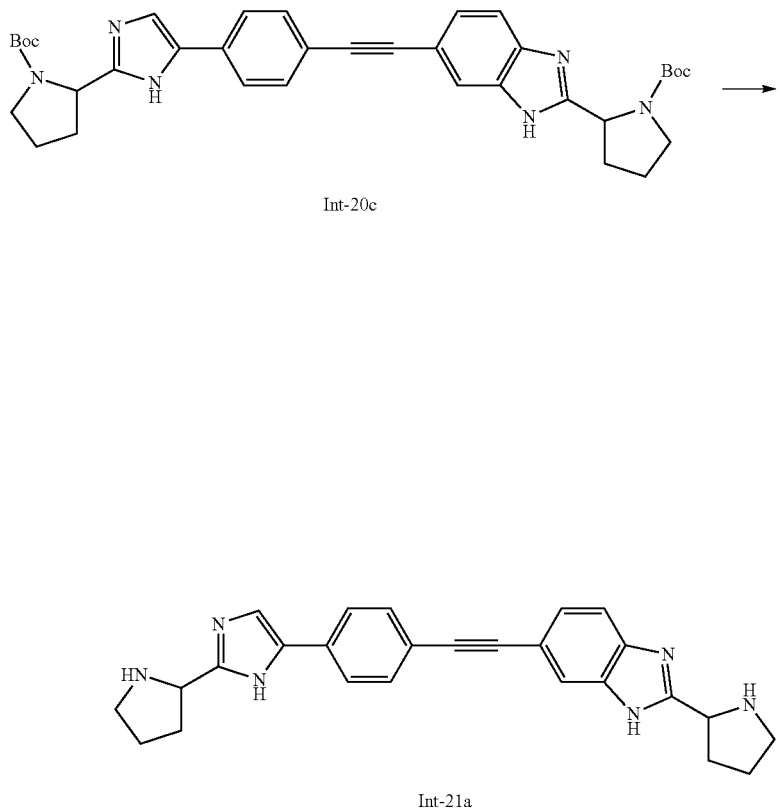

To Compound Int-20c (26 mg, 0.042 mmol) was dissolved in CH$_2$Cl$_2$ (3 mL) and TFA (1 mL) and the mixture was allowed to stir at room temperature for 2.5 hours then concentrated in vacuo. The residue obtained was re-dissolved in MeOH (5 mL) and to the resulting solution was added 4 M HCl in dioxane (1 mL). The mixture was then concentrated in vacuo to provide Compound Int-21a (24 mg, quant.) as a hydrochloride salt, which was used without further purification. FABMS: (M+H)$^+$=423.2.

Example 22

Preparation of Compound 56

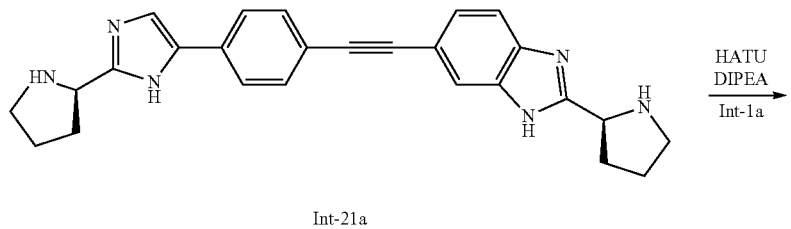

Int-21a

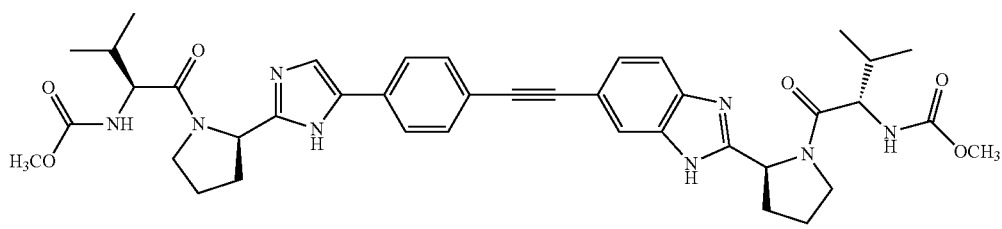

56

To a solution of Compound Int-21a (14.8 mg, 0.026 mmol), N-methoxycarbonyl-valine Int-1a (12 mg, 0.068 mmol), HATU (30.0 mg, 0.078 mmol) in anhydrous DMF (2.0 mL) at 0° C. was added diisopropylethyl amine (0.020 mL, 0.156 mmol). The resulting mixture was allowed to stir at 0° C. for 30 minutes and then at room temperature for 2 hours. EtOAc (40 mL) water (40 mL) were added and the layers were separated. The aqueous solution was extracted with EtOAc (30 mL). The combined organic solution was washed with 1:1 mixture of water and saturated aqueous sodium bicarbonate solution (2×50 mL), dried over MgSO$_4$, filtered and concentrated in vacuo. The crude product was purified using reverse phase HPLC with 10-100% acetonitrile/water (both with 0.1% TFA) to provide Compound 56 (3.1 mg, 16%). FABMS: (M+H)$^+$=737.6.

Example 23

Preparation of Compound 57

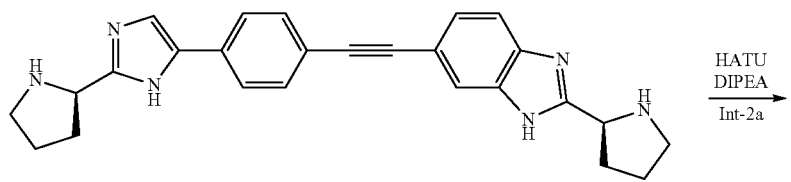

Int-21a

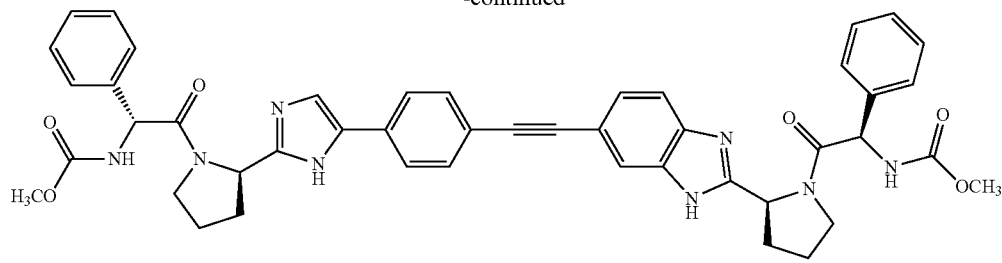

57

To a solution of Compound 15 (9.0 mg, 0.016 mmol), N-methoxycarbonyl-phenylglycine (Int-2a, 8.8 mg, 0.042 mmol), HATU (18.2 mg, 0.048 mmol) in anhydrous DMF (1.0 mL) at 0° C. was added diisopropylethyl amine (0.016 mL, 0.096 mmol). The resulting mixture was allowed to stir at 0° C. for 30 minutes and then at room temperature for 2 hours. EtOAc (30 mL) and water (30 mL) were added, and the layers were separated. The aqueous solution was back-extracted with EtOAc (20 mL). The combined organic layers were washed with 1:1 mixture of water and saturated aqueous sodium bicarbonate solution (2×50 mL), dried over MgSO$_4$, filtered and concentrated in vacuo. The crude product was purified using reverse phase HPLC with 10-100% acetonitrile/water (both with 0.1% TFA) to provide Compound 57 (1.2 mg, 9%). FABMS: (M+H)$^+$=805.6.

Example 24

Cell-Based HCV Replicon Assay

To measure cell-based anti-HCV activity of selected compounds of the present invention, the following replicon assay can be used.

Replicon cells are seeded at 5000 cells/well in 96-well collagen I-coated Nunc plates in the presence of the test compound. Various concentrations of test compound, typically in 10 serial 2-fold dilutions, are added to the assay mixture, with the starting concentration ranging from 10 μM to 0.001 μM. The final concentration of DMSO should be about 0.5%, and the final concentration of fetal bovine serum should be about 5%, in the assay media. Cells are harvested on day 3 by the addition of 1× cell lysis buffer (Ambion cat #8721). The replicon RNA level is then measured (using, for example, the real time PCR (Taqman assay)). The amplicon is located in 5B. The PCR primers are: 5B.2F, ATGGACAG-GCGCCCTGA (SEQ ID NO. 1); 5B.2R, TTGATGGGCAGCTTGGTTTC (SEQ ID NO. 2); the probe sequence is FAM-labeled CACGCCATGCGCTGCGG (SEQ ID NO. 3). GAPDH RNA is to be used as endogenous control and is amplified in the same reaction as NS5B (multiplex PCR) using the primers and the VIC-labeled probe recommended by the manufacturer (PE Applied Biosystems). The real-time RT-PCR reactions can be run on an ABI PRISM 7900HT Sequence Detection System using the following program: 48° C. for 30 minutes, 95° C. for 10 minutes, 40 cycles of 95° C. for 15 sec, 60° C. for 1 minute. The ΔCT values ($CT_{5B}$-$CT_{GAPDH}$) are then plotted against the concentration of test compound and fitted to the sigmoid dose-response model using XLfit4 (MDL). $EC_{50}$ is defined as the concentration of inhibitor necessary to achieve ΔCT=1 over the projected baseline; $EC_{90}$ is defined as the concentration necessary to achieve ΔCT=3.2 over the baseline. Alternatively, to quantitate the absolute amount of replicon RNA, a standard curve can be established by including serially diluted T7 transcripts of replicon RNA in the Taqman assay. All Taqman reagents can be obtained from PE Applied Biosystems. Such an assay procedure is described in detail in Malcolm et al., *Antimicrobial Agents and Chemotherapy* 50: 1013-1020 (2006).

HCV replicon assay data was calculated for various genotypes for selected compounds of the present invention using this method and is provided in the table below.

| Compound No. | LRMS (M + 1) | EC50 1a 1A7 (nM) | EC50 1b c16 (nM) | EC50 2a JFH (nM) | EC50 1b Y93H (nM) |
|---|---|---|---|---|---|
| 56 | 737.6 | 0.3 | 0.016 | 0.3 | 5 |
| 57 | 805.6 | 0.41 | 0.001 | 0.019 | 0.5 |
| 58 | 624 | ND | 251.2 | ND | ND |

ND = no data

The study of the HCV life cycle has been difficult due to the lack of a cell-culture system to support the HCV virus. To date, compounds in different structural classes acting on different sites within the HCV polyprotein have demonstrated efficacy in various species, including humans, in reducing HCV viral titers. Furthermore, the subgenomic replicon assay is highly correlated with efficacy in non-humans and humans infected with HCV. See K. del Carmen et al., *Annals of Hepatology*, 2004, 3:54.

It is accepted that the HCV replicon system described above is useful for the development and the evaluation of antiviral drugs. See Pietschmann, T. & Bartenschlager, R., *Current Opinion in Drug Discovery Research* 2001, 4:657-664).

Uses of the Fused Aryl Tricyclic Compounds

The Fused Aryl Tricyclic Compounds are useful in human and veterinary medicine for treating or preventing a viral infection in a patient. In one embodiment, the Fused Aryl Tricyclic Compounds can be inhibitors of viral replication. In another embodiment, the Fused Aryl Tricyclic Compounds can be inhibitors of HCV replication. Accordingly, the Fused Aryl Tricyclic Compounds are useful for treating viral infections, such as HCV. In accordance with the invention, the Fused Aryl Tricyclic Compounds can be administered to a patient in need of treatment or prevention of a viral infection.

Accordingly, in one embodiment, the invention provides methods for treating a viral infection in a patient comprising administering to the patient an effective amount of at least one Fused Aryl Tricyclic Compound or a pharmaceutically acceptable salt thereof.

Treatment or Prevention of a Flaviviridae Virus

The Fused Aryl Tricyclic Compounds can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Fused Aryl Tricyclic Compounds are useful in the inhibition of HCV (e.g., HCV NS5A), the treatment of HCV infection and/or reduction of the likelihood or severity of symptoms of HCV infection and the inhibition of HCV viral replication and/or HCV viral production in a cell-based system. For example, the Fused Aryl Tricyclic Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Fused Aryl Tricyclic Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Fused Aryl Tricyclic Compounds are also useful in the preparation and execution of screening assays for antiviral compounds. For example the Fused Aryl Tricyclic Compounds are useful for identifying resistant HCV replicon cell lines harboring mutations within NS5A, which are excellent screening tools for more powerful antiviral compounds. Furthermore, the Fused Aryl Tricyclic Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Substituted Fused Aryl Tricyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Substituted Fused Aryl Tricyclic Compound, or a pharmaceutically acceptable salt thereof, and (ii) at least one additional therapeutic agent that is other than a Substituted Fused Aryl Tricyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Substituted Fused Aryl Tricyclic Compound and an additional therapeutic agent may be present in fixed amounts (dosage amounts) in a single dosage unit (e.g., a capsule, a tablet and the like).

In one embodiment, the at least one Substituted Fused Aryl Tricyclic Compound is administered during a time when the additional therapeutic agent(s) exert their prophylactic or therapeutic effect, or vice versa.

In another embodiment, the at least one Substituted Fused Aryl Tricyclic Compound and the additional therapeutic agent(s) are administered in doses commonly employed when such agents are used as monotherapy for treating a viral infection.

In another embodiment, the at least one Substituted Fused Aryl Tricyclic Compound and the additional therapeutic agent(s) are administered in doses lower than the doses commonly employed when such agents are used as monotherapy for treating a viral infection.

In still another embodiment, the at least one Substituted Fused Aryl Tricyclic Compound and the additional therapeutic agent(s) act synergistically and are administered in doses lower than the doses commonly employed when such agents are used as monotherapy for treating a viral infection.

In one embodiment, the at least one Substituted Fused Aryl Tricyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Substituted Fused Aryl Tricyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Substituted Fused Aryl Tricyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082, 484, WO 08/082,488, WO 08/083,351, WO 08/136,815, WO 09/032,116, WO 09/032,123, WO 09/032,124 and WO 09/032,125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™) interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

Additional HCV protease inhibitors useful in the present compositions and methods include, but are not limited to, SCH503034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), MK-7009 (Merck), TMC-435350 (Medivir), ITMN-1911R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31): 9340-9348 (1997); Ingallinella et al., *Biochemistry*, 37(25): 8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10): 7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

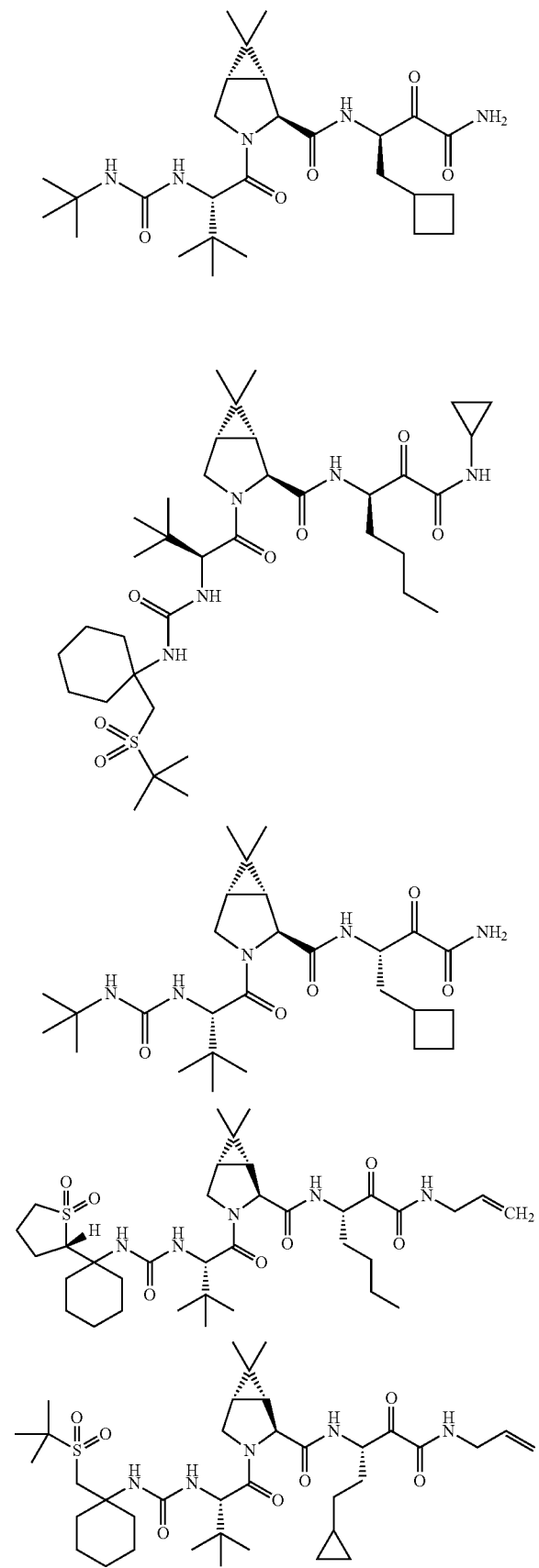

131
-continued
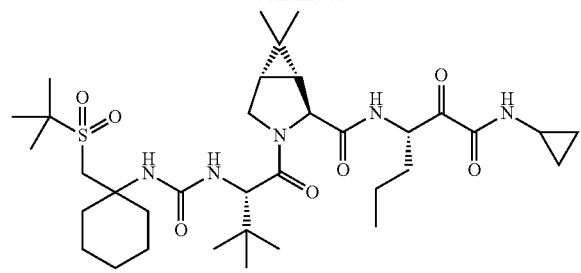
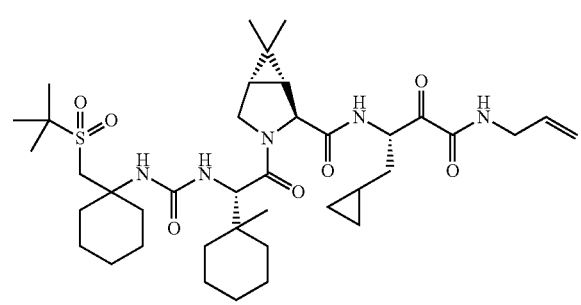
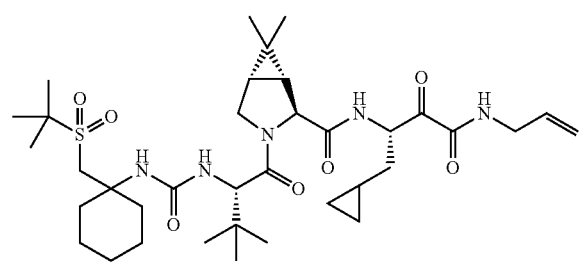
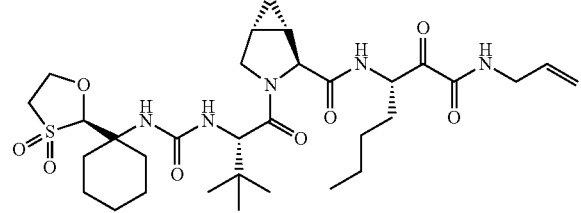
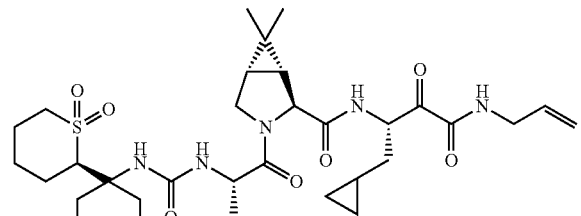
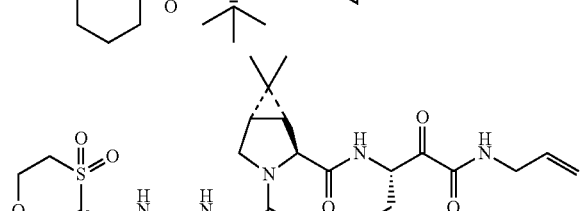
132
-continued
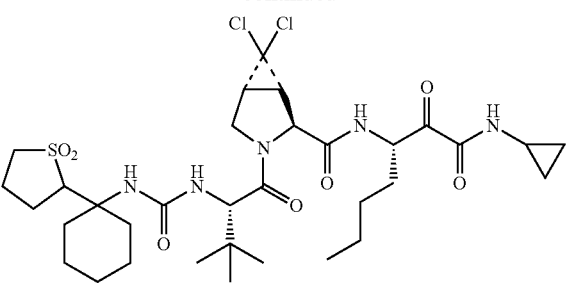
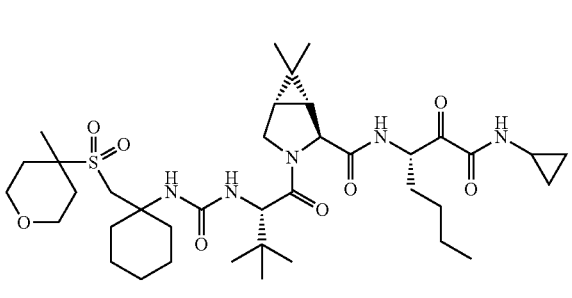
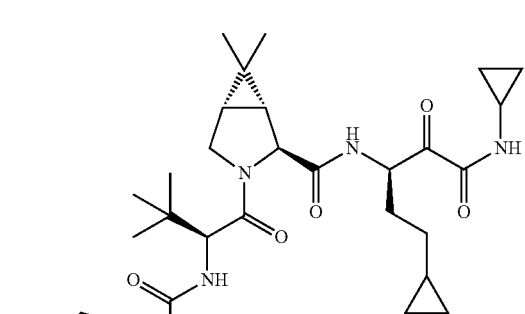
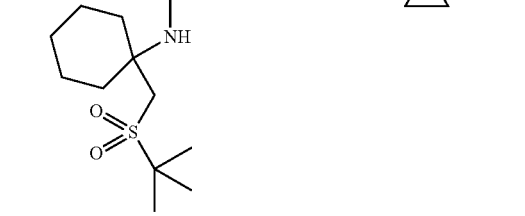
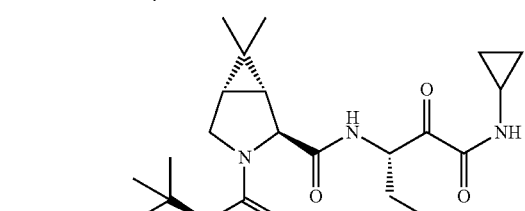
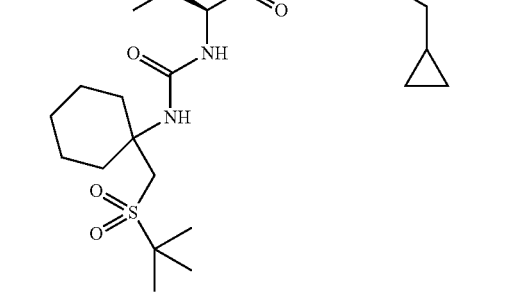

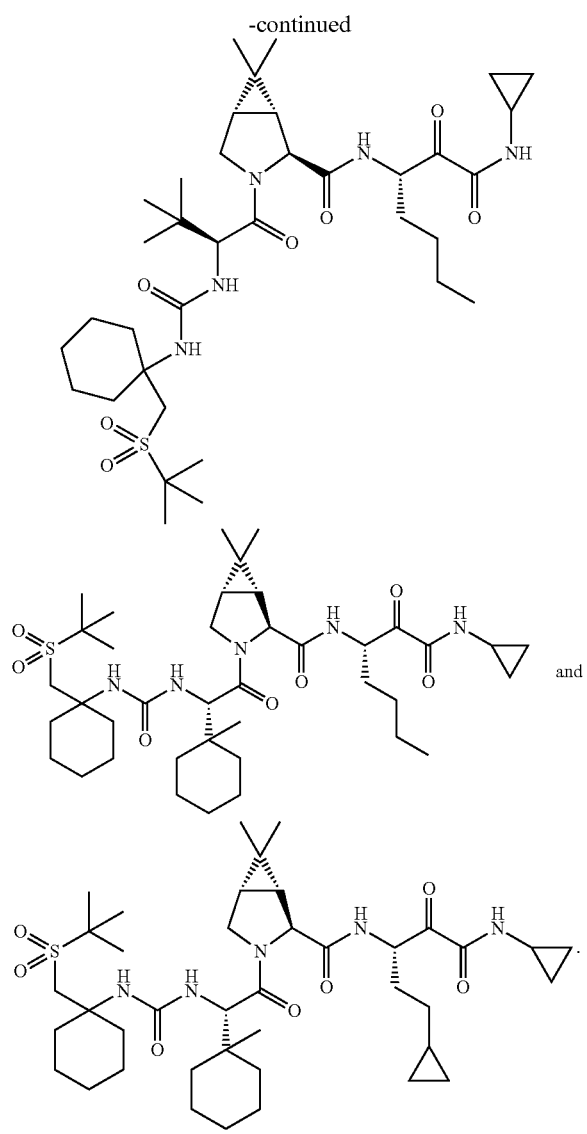

and

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), BMS-790052 (Bristol-Myers Squibb, see Gao et al., Nature, 465:96-100 (2010)), viramidine, A-831 (Arrow Therapeutics); an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPROTM (Pevion Biotect), HCV/MF59 (Chiron/Novartis) and Civacir (NAB I).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO206 (Progenies), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Substituted Fused Aryl Tricyclic Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another every six hours, or when the preferred pharmaceutical compositions are different, e.g., one is a tablet and one is a capsule. A kit comprising the separate dosage forms is therefore advantageous.

Generally, a total daily dosage of the at least one Substituted Fused Aryl Tricyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU(12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered pegylated-interferon alpha and ribavirin.

Compositions and Administration

Due to their activity, the Fused Aryl Tricyclic Compounds are useful in veterinary and human medicine. As described above, the Fused Aryl Tricyclic Compounds are useful for treating or preventing HCV infection in a patient in need thereof.

When administered to a patient, the Fused Aryl Tricyclic Compounds can be administered as a component of a composition that comprises a pharmaceutically acceptable carrier or vehicle. The present invention provides pharmaceutical compositions comprising an effective amount of at least one Fused Aryl Tricyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Aryl Tricyclic Compounds are administered orally.

In another embodiment, the one or more Fused Aryl Tricyclic Compounds are administered intravenously.

In another embodiment, the one or more Fused Aryl Tricyclic Compounds are administered topically.

In still another embodiment, the one or more Fused Aryl Tricyclic Compounds are administered sublingually.

In one embodiment, a pharmaceutical preparation comprising at least one Fused Aryl Tricyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Aryl Tricyclic Compound(s) by weight or volume. In various embodiments, the present compositions can contain, in one embodiment, from about 1% to about 70% or from about 5% to about 60% of the Fused Aryl Tricyclic Compound(s) by weight or volume.

The quantity of Fused Aryl Tricyclic Compound in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Aryl Tricyclic Compounds will be regulated according to the judgment of the attending clinician considering such factors as age, condition and size of the patient as well as severity of the symptoms being treated. Generally, a total daily dosage of the Fused Aryl Tricyclic Compounds range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Fused Aryl Tricyclic Compound or a pharmaceutically acceptable salt thereof; (ii) one or more additional therapeutic agents that are not a Fused Aryl Tricyclic Compound; and (iii) a pharmaceutically acceptable carrier, wherein the amounts in the composition are together effective to treat HCV infection.

Kits

In one aspect, the present invention provides a kit comprising a therapeutically effective amount of at least one Fused Aryl Tricyclic Compound, or a pharmaceutically acceptable salt of said compound and a pharmaceutically acceptable carrier, vehicle or diluent.

In another aspect the present invention provides a kit comprising an amount of at least one Fused Aryl Tricyclic Compound, or a pharmaceutically acceptable salt of said compound and an amount of at least one additional therapeutic agent listed above, wherein the amounts of the two or more active ingredients result in a desired therapeutic effect. In one embodiment, the one or more Fused Aryl Tricyclic Compounds and the one or more additional therapeutic agents are provided in the same container. In one embodiment, the one or more Fused Aryl Tricyclic Compounds and the one or more additional therapeutic agents are provided in separate containers.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

A number of references have been cited herein. Such citations are not to be construed as an admission that said cited references are prior art to this application.

What is claimed is:

1. A compound having the formula:

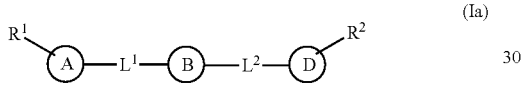
(Ia)

or a pharmaceutically acceptable salt thereof,
wherein:
A is

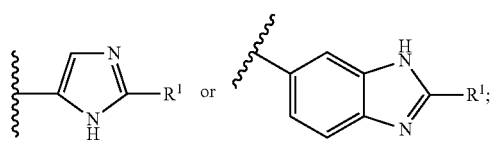

B is selected from:

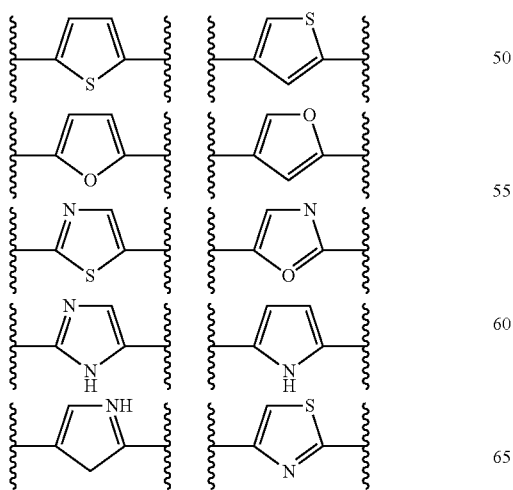

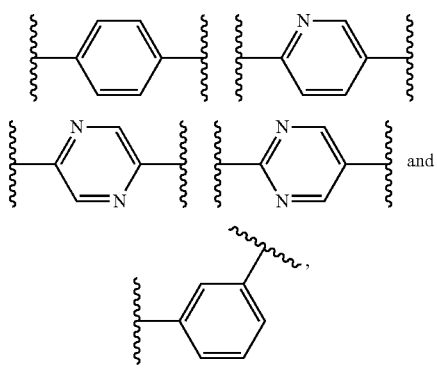

wherein either one of the two available bonds of each depicted group can be connected to either of the two groups flanking B;

D is:

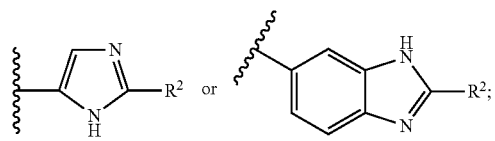

$L^1$ is a bond, —CH$_2$—, —CH$_2$—CH$_2$—, —CH$_2$—C(O)—, —NHCH$_2$—, —NH, —C(O)—, —N(CH$_3$)—, —CH=CH— or —C≡C—;

$L^2$ is a bond, —CH$_2$—, —CH$_2$—CH$_2$—, —C≡C—, —NH, —C(O)— or —N(CH$_3$)—, such that at least one of $L^1$ and $L^2$ is other than a bond;

$R^1$ is:

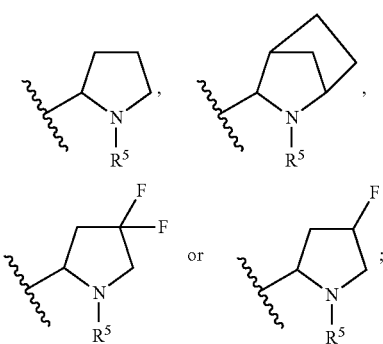

$R^2$ is:

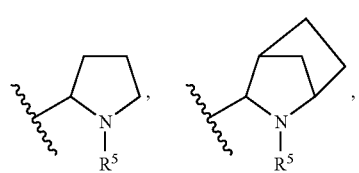

-continued

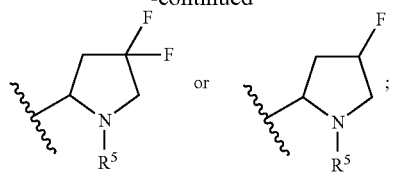

each occurrence of $R^5$ is independently —C(O)—C($R^{21}$)—NHC(O)O-alkyl, —C(O)—C(alkyl)-NHC(O)N($R^{20}$)$_2$, —C(O)—C($R^{20}$)—N($R^{20}$)$_2$, —C(O)-alkyl, —C(O)O-alkyl or —C(O)—C(alkyl)-NHS(O)$_2$-alkyl;

each occurrence of $R^{20}$ is independently H or —$C_1$-$C_4$ alkyl; and each occurrence of $R^{21}$ is independently phenyl or —$C_1$-$C_4$ alkyl.

2. The compound of claim 1, wherein A-$R^1$ and D-$R^2$ are each independently selected from

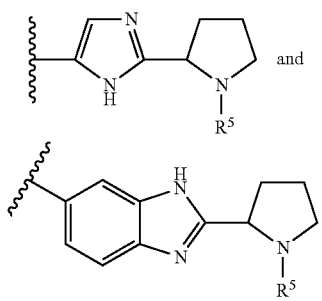

3. The compound of claim 2, wherein B is:

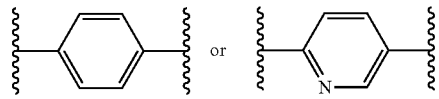

wherein either one of the two available bonds of each depicted group can be connected to either of the two groups flanking B.

4. The compound of claim 2, wherein each occurrence of $R^5$ is independently selected from:

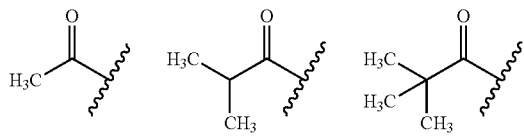

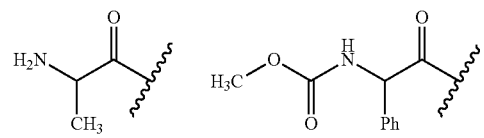

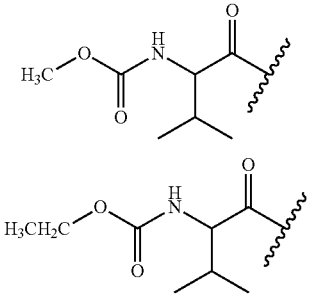

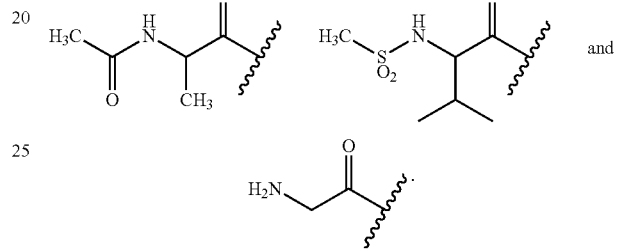

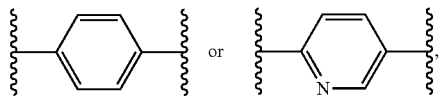 [SMILES: *c1ccc(*)cc1 ; *c1ccc(*)nc1]

5. The compound of claim 4, wherein B is:

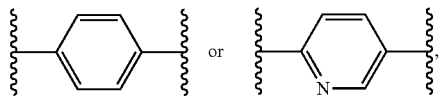 [SMILES: *c1ccc(*)cc1 ; *c1ccc(*)nc1]

wherein either one of the two available bonds of each depicted group can be connected to either of the two groups flanking B.

6. The compound of claim 4, wherein each occurrence of $R^5$ is

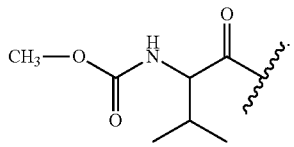 [SMILES: *C(=O)C(NC(=O)OC)C(C)C]

7. A compound having the structure:

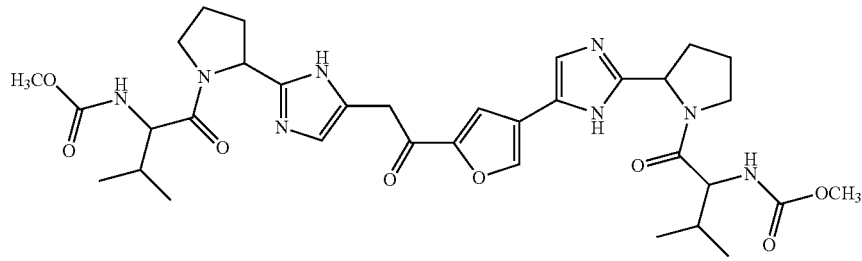

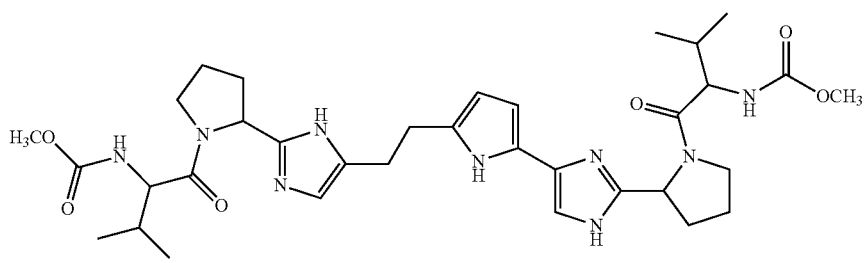
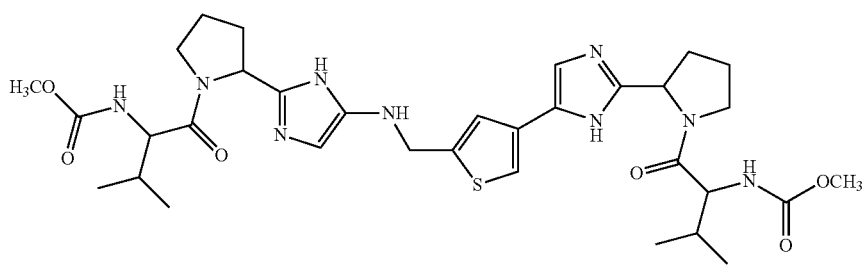
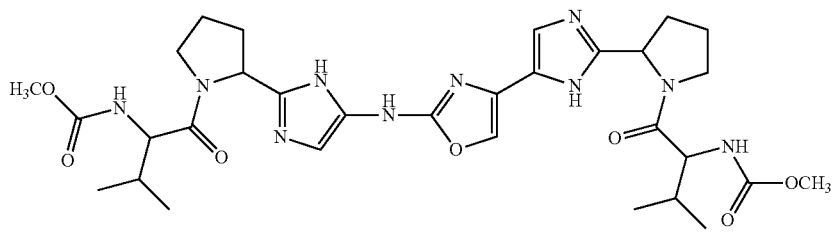
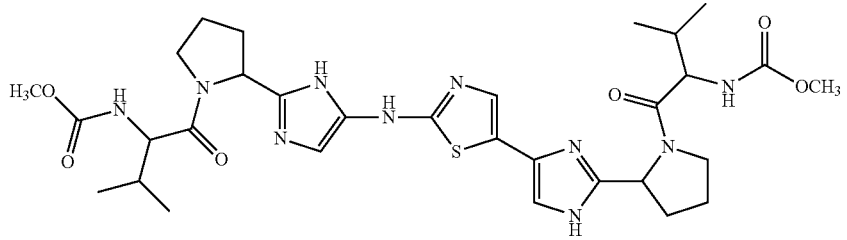
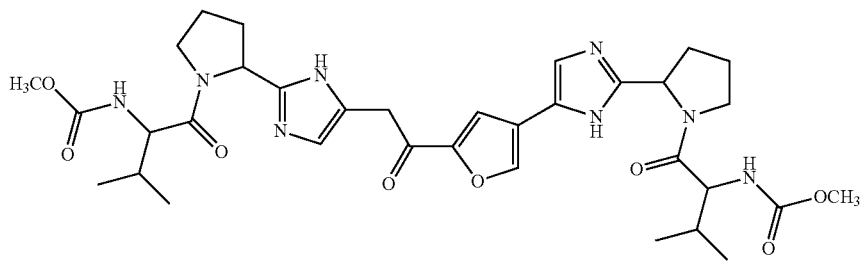
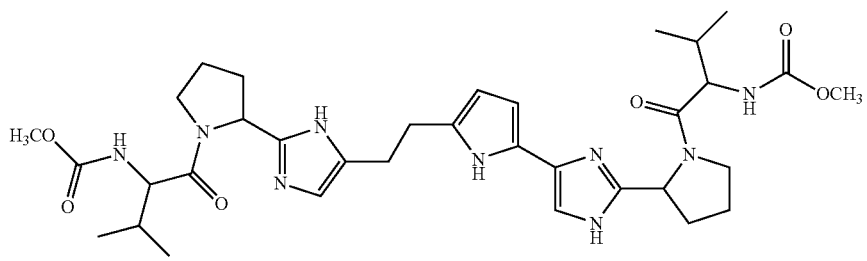

-continued
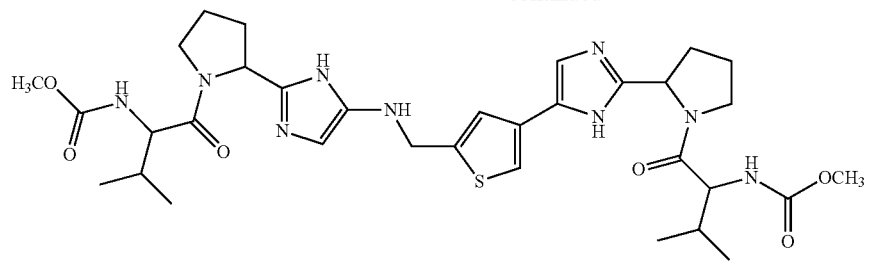
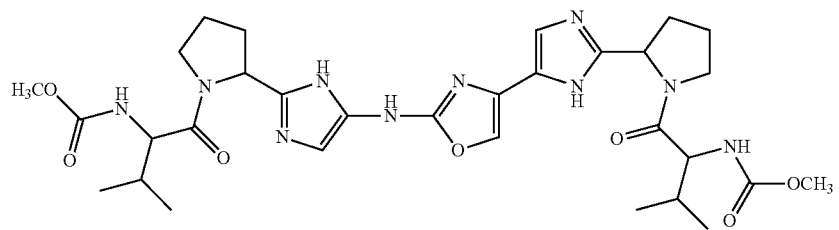
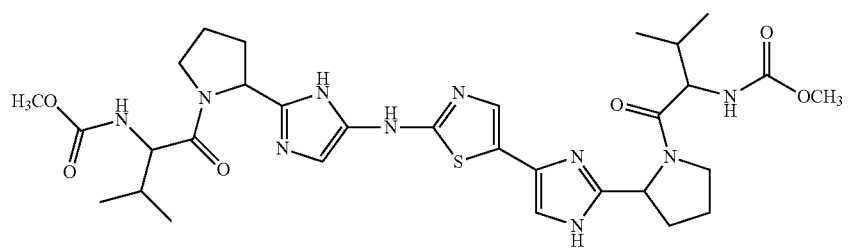
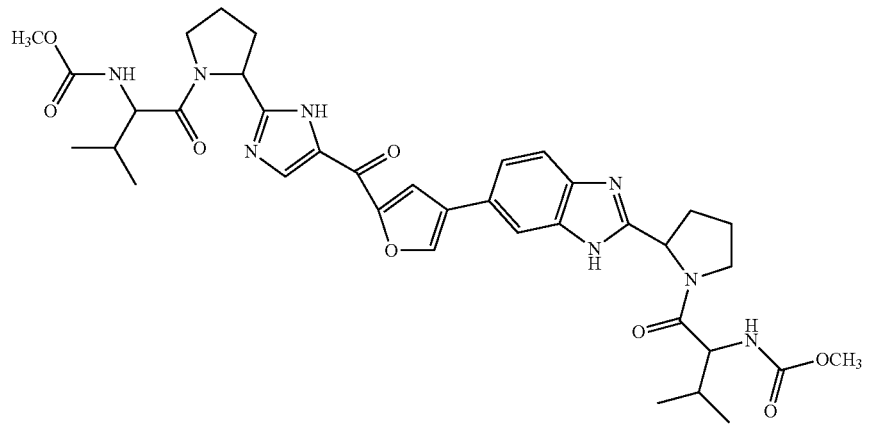
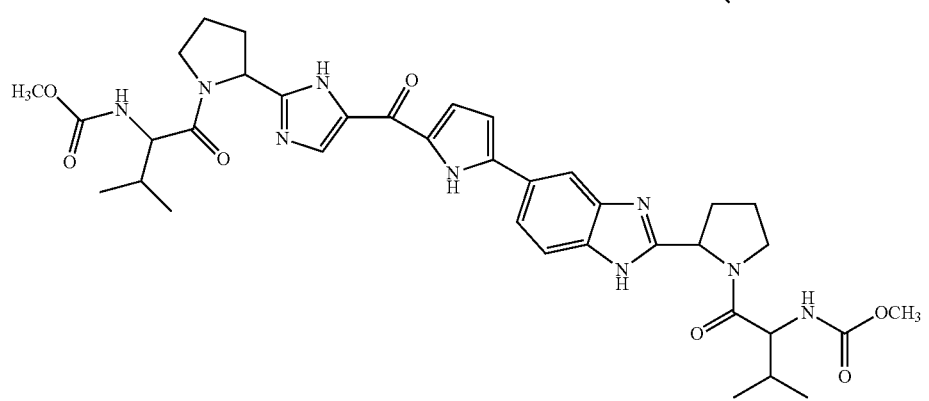

-continued
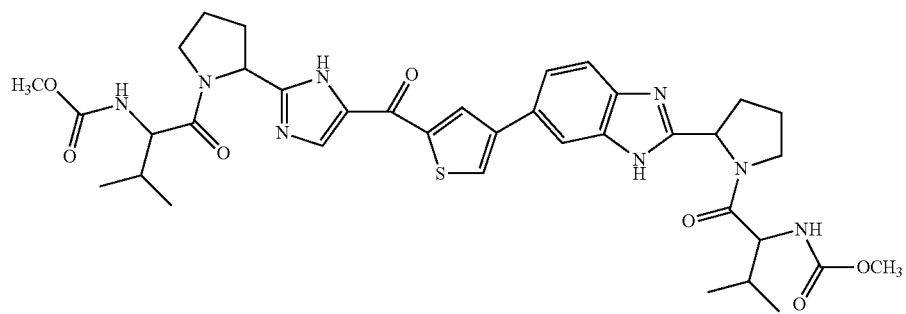
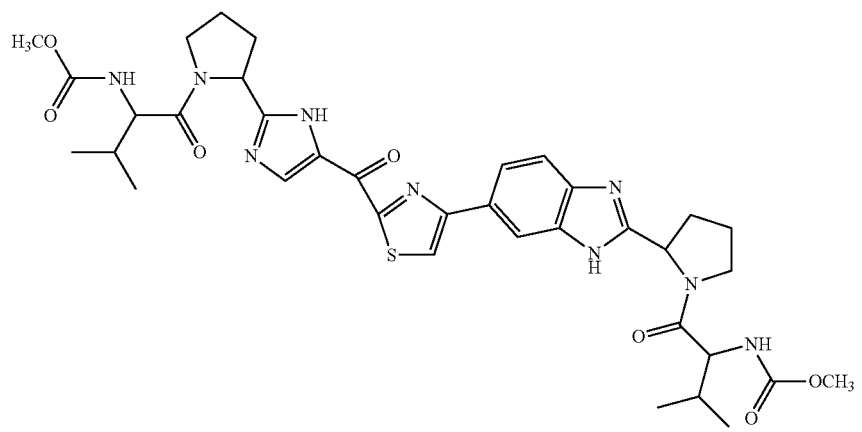
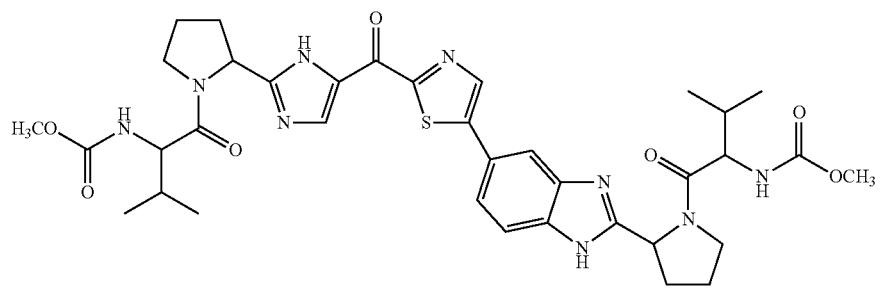
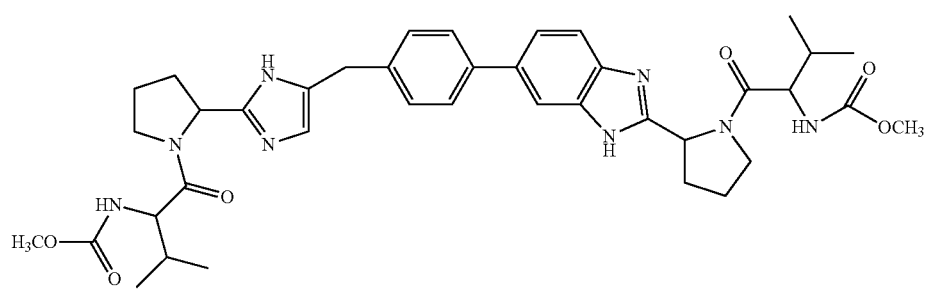
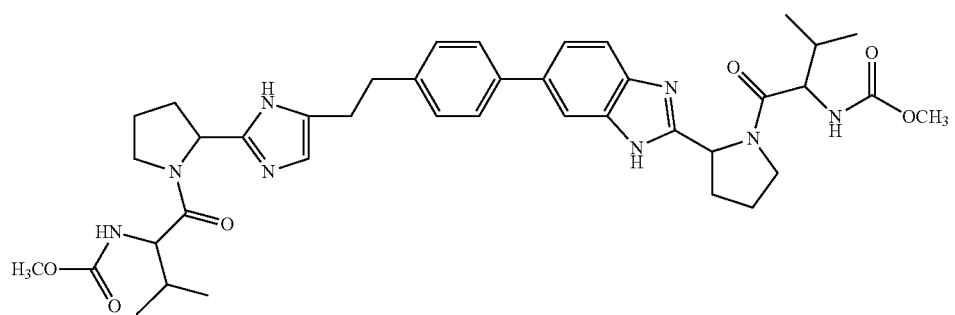

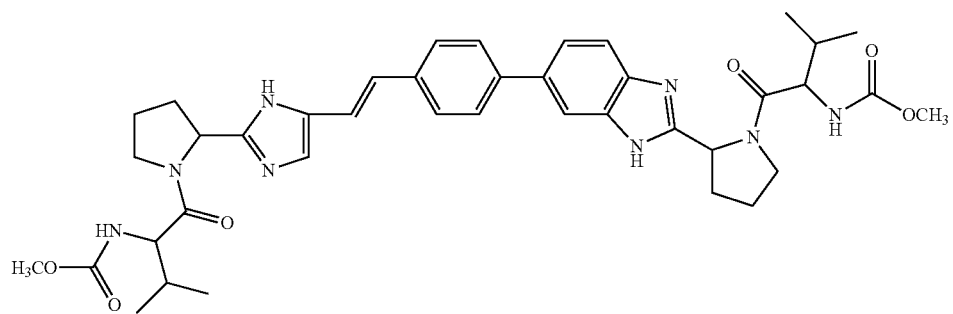
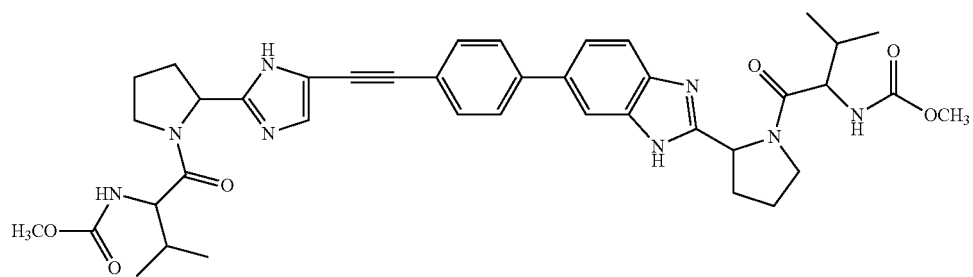
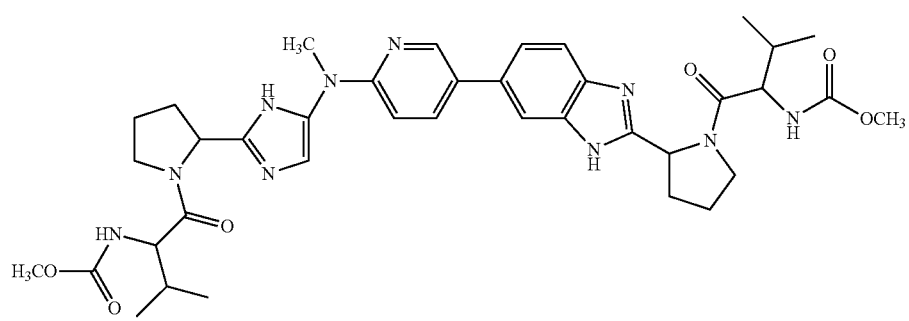
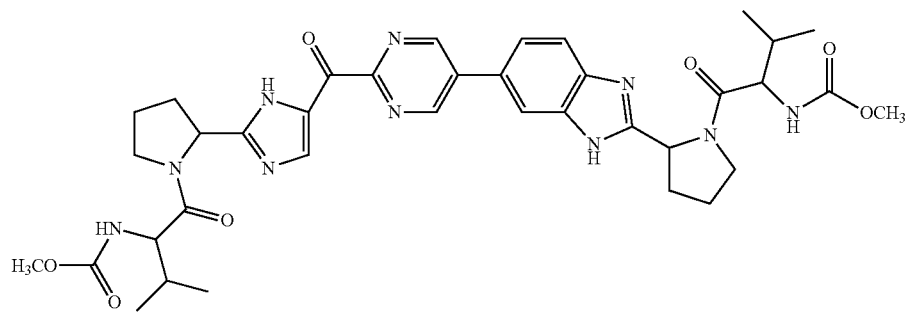
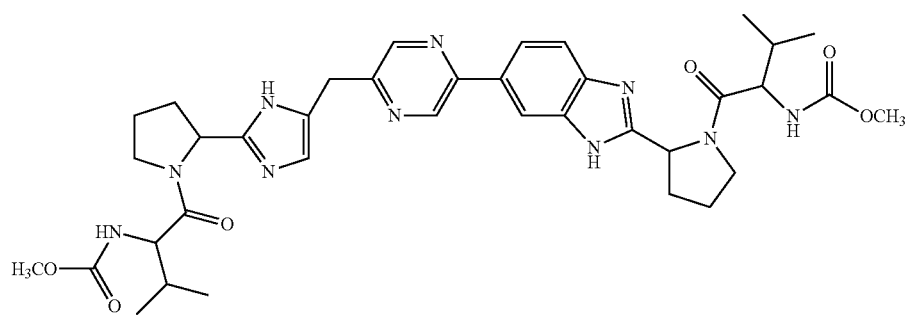

-continued
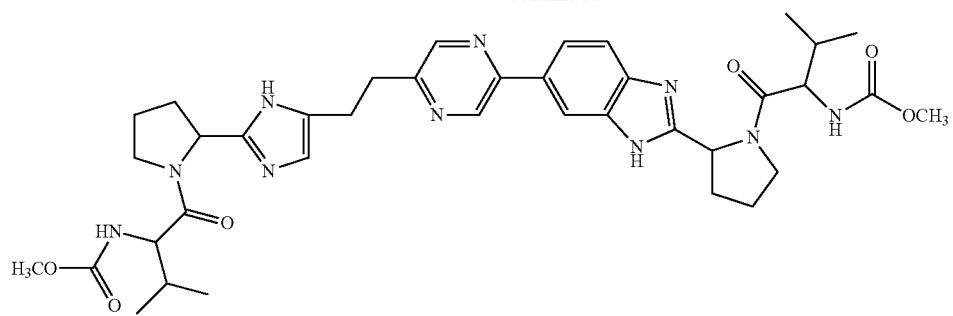
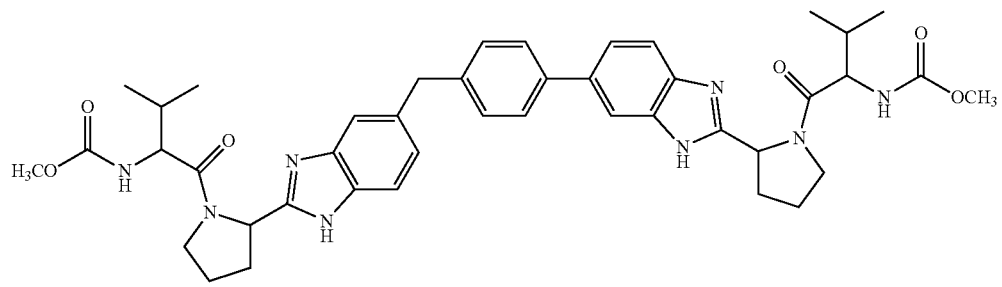
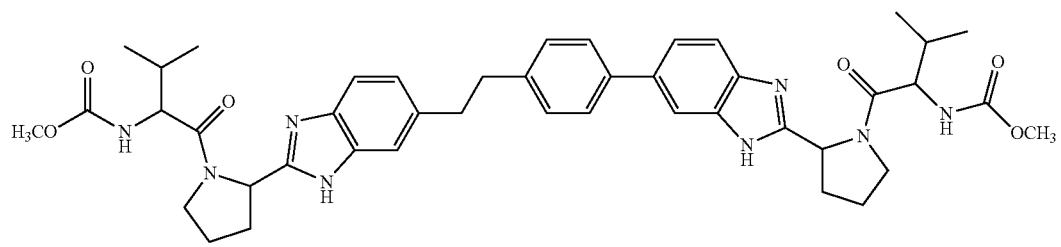
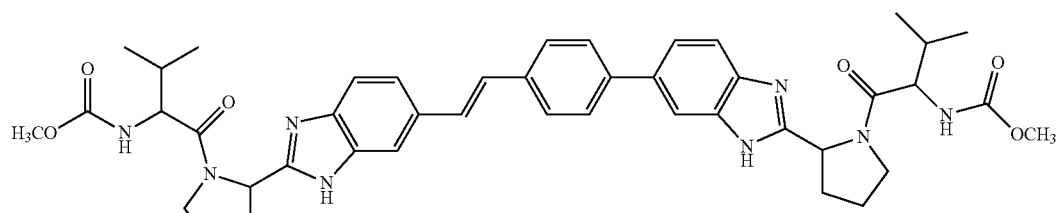
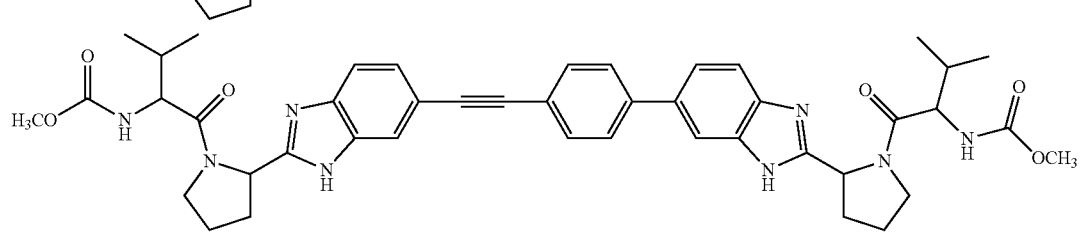
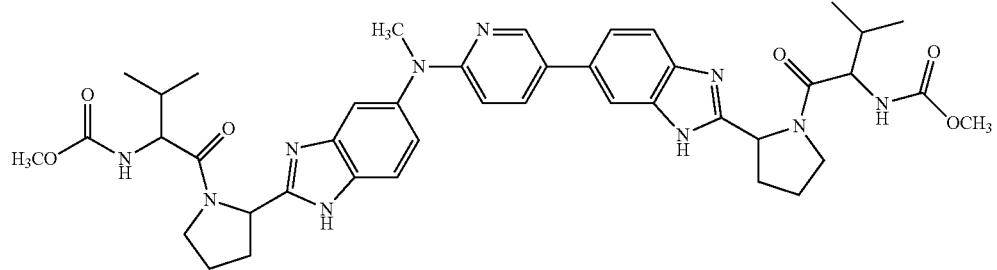

-continued
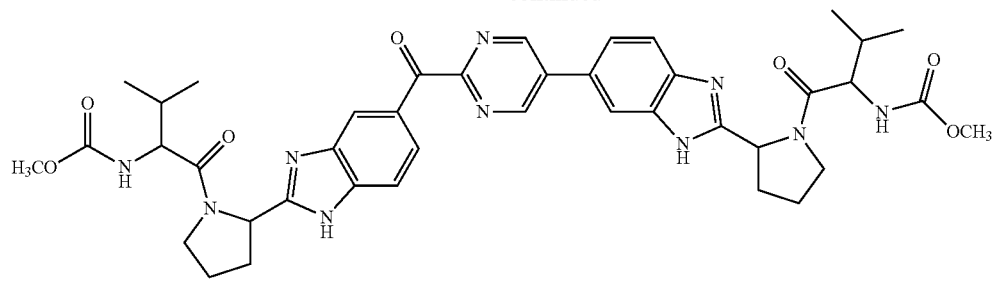
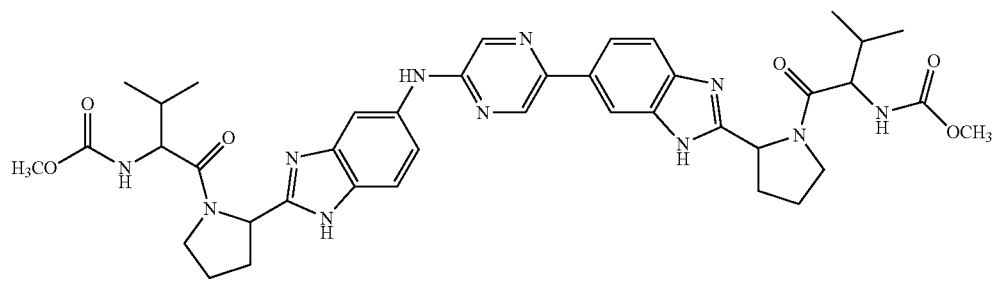
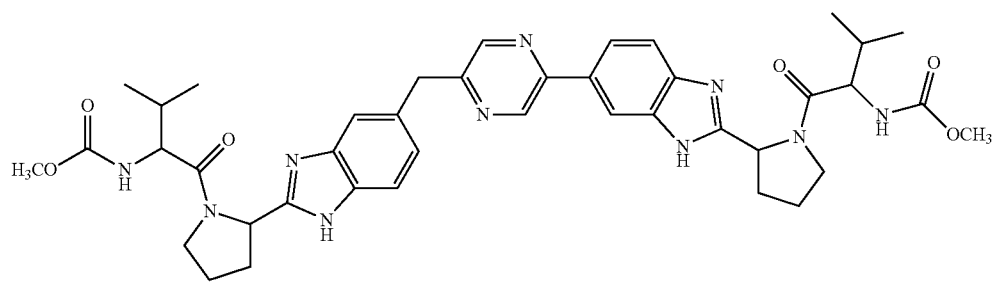
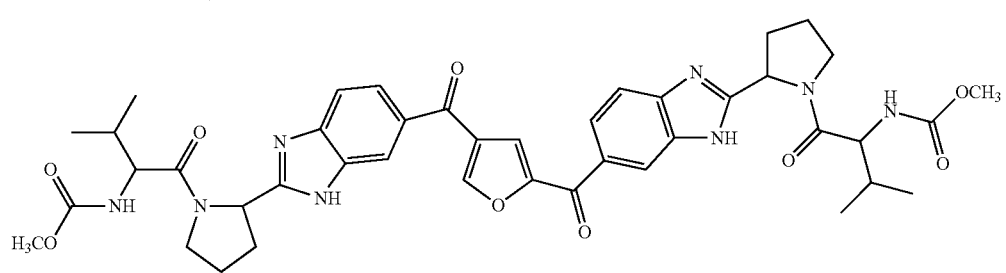
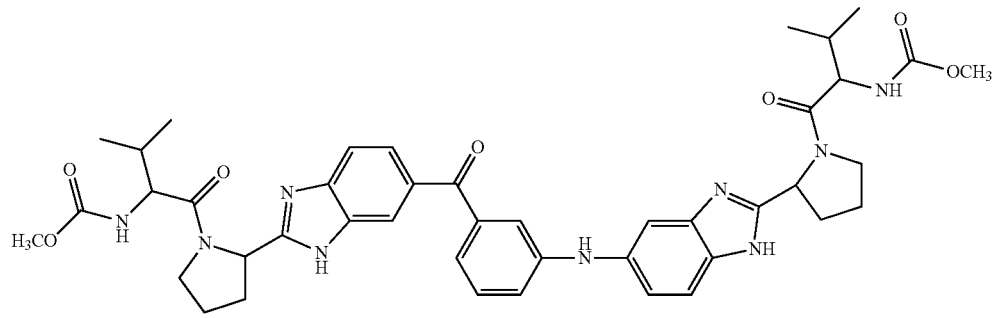
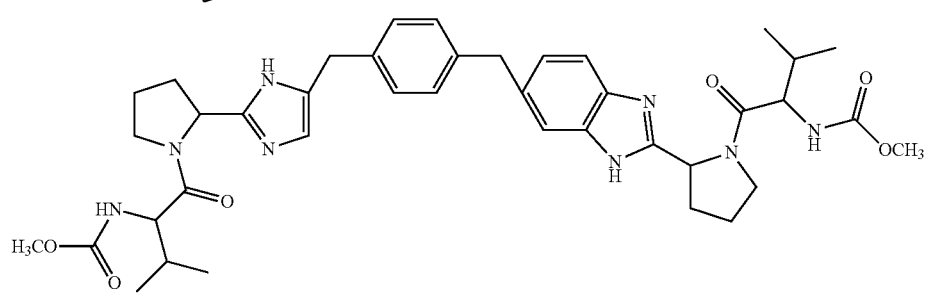

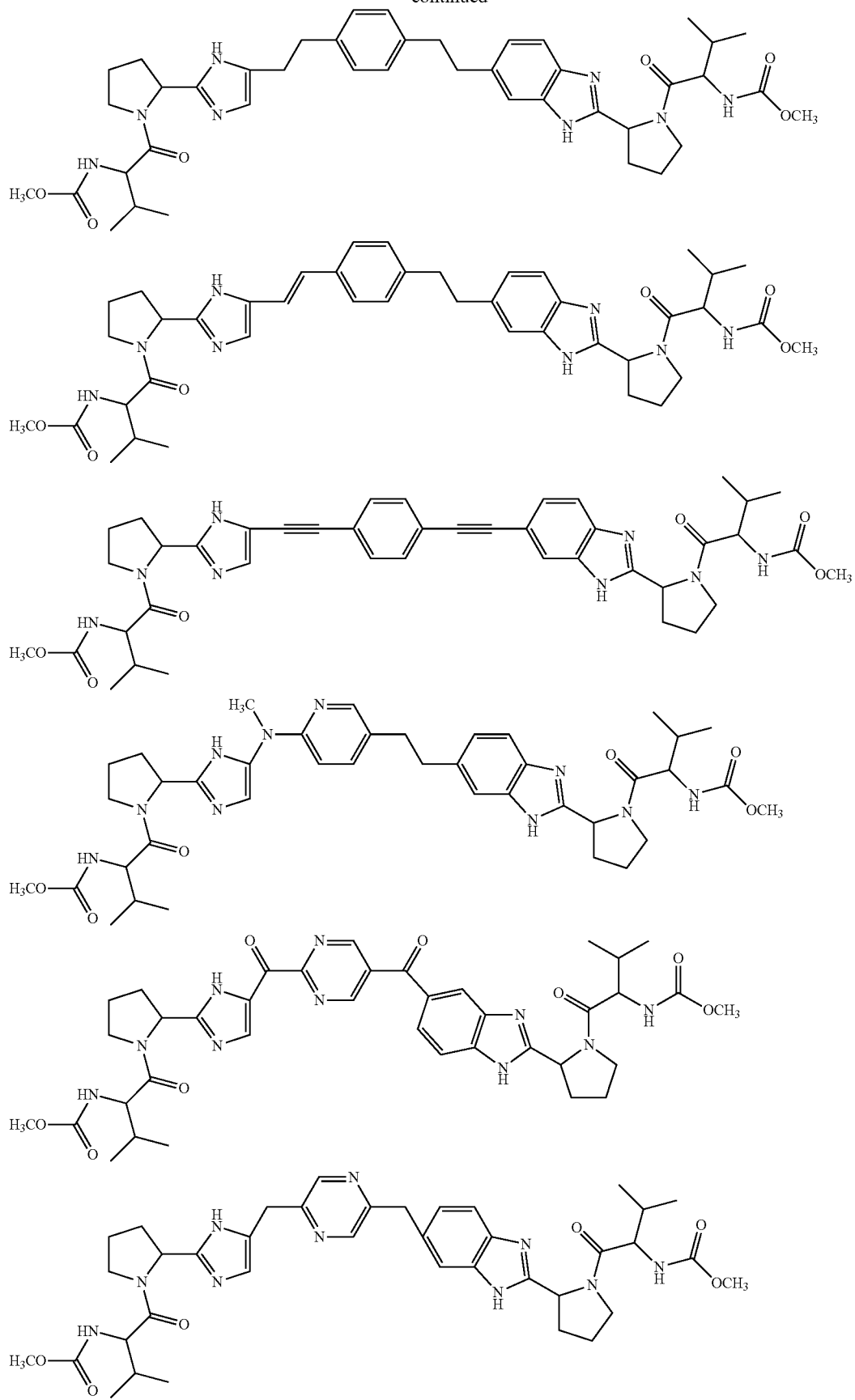

-continued
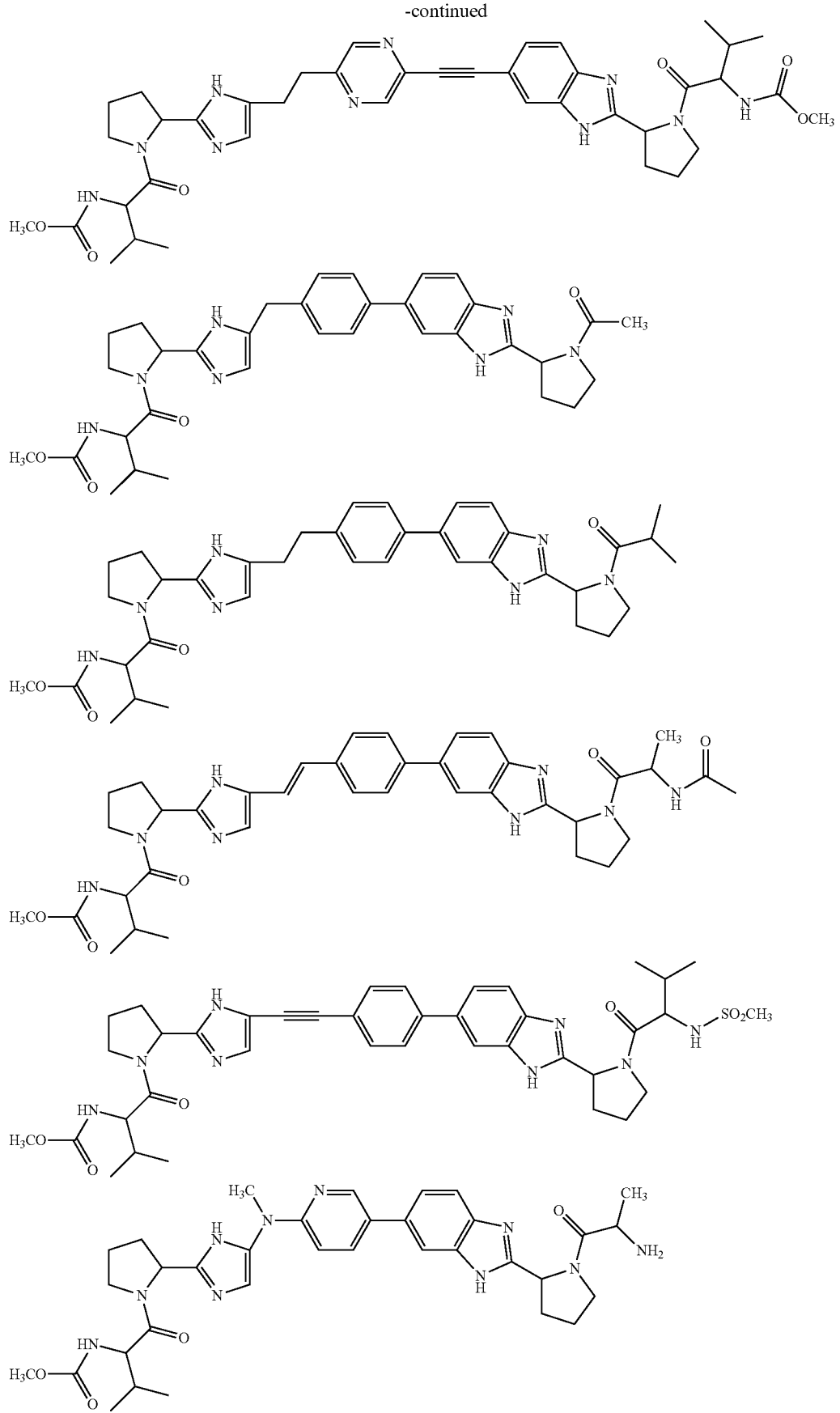

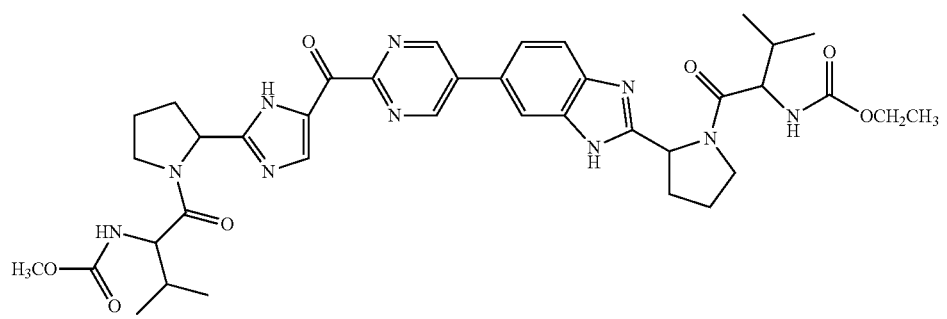
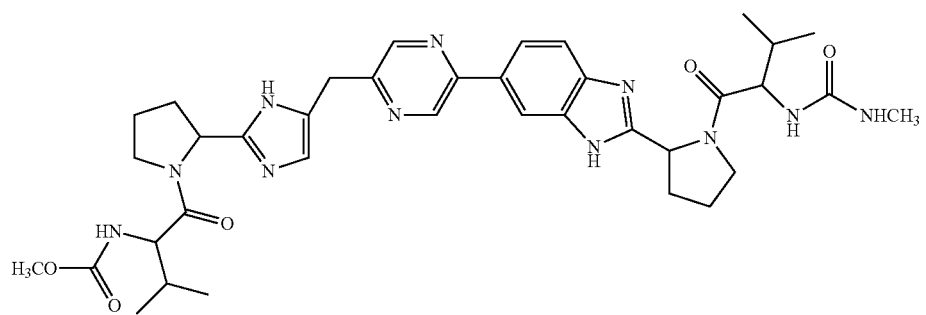
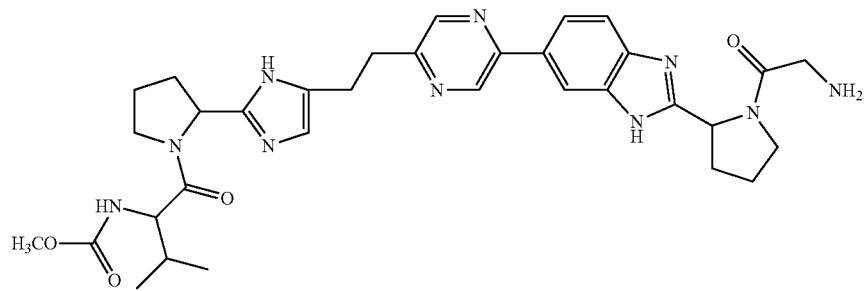
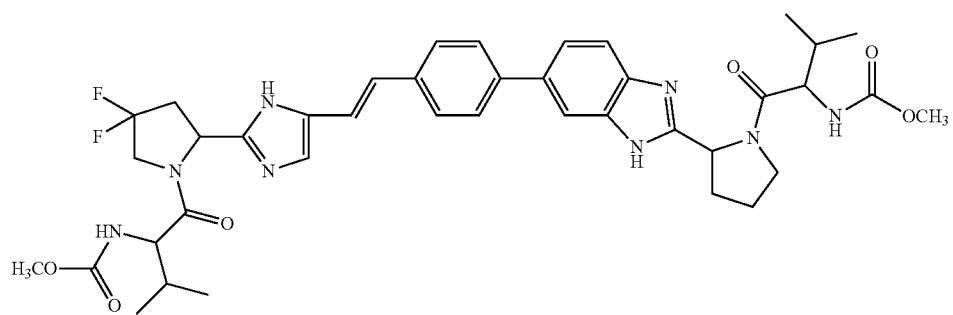
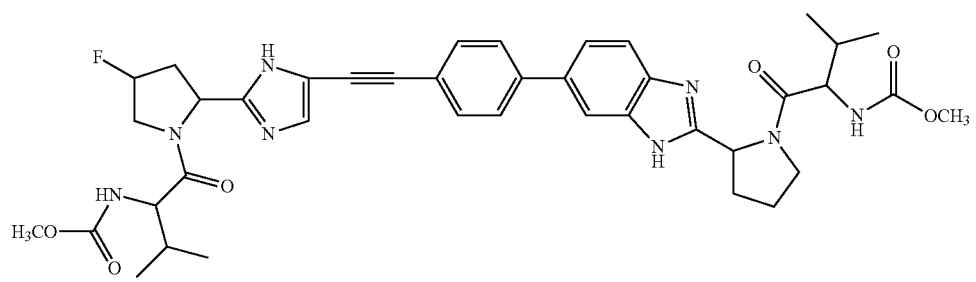

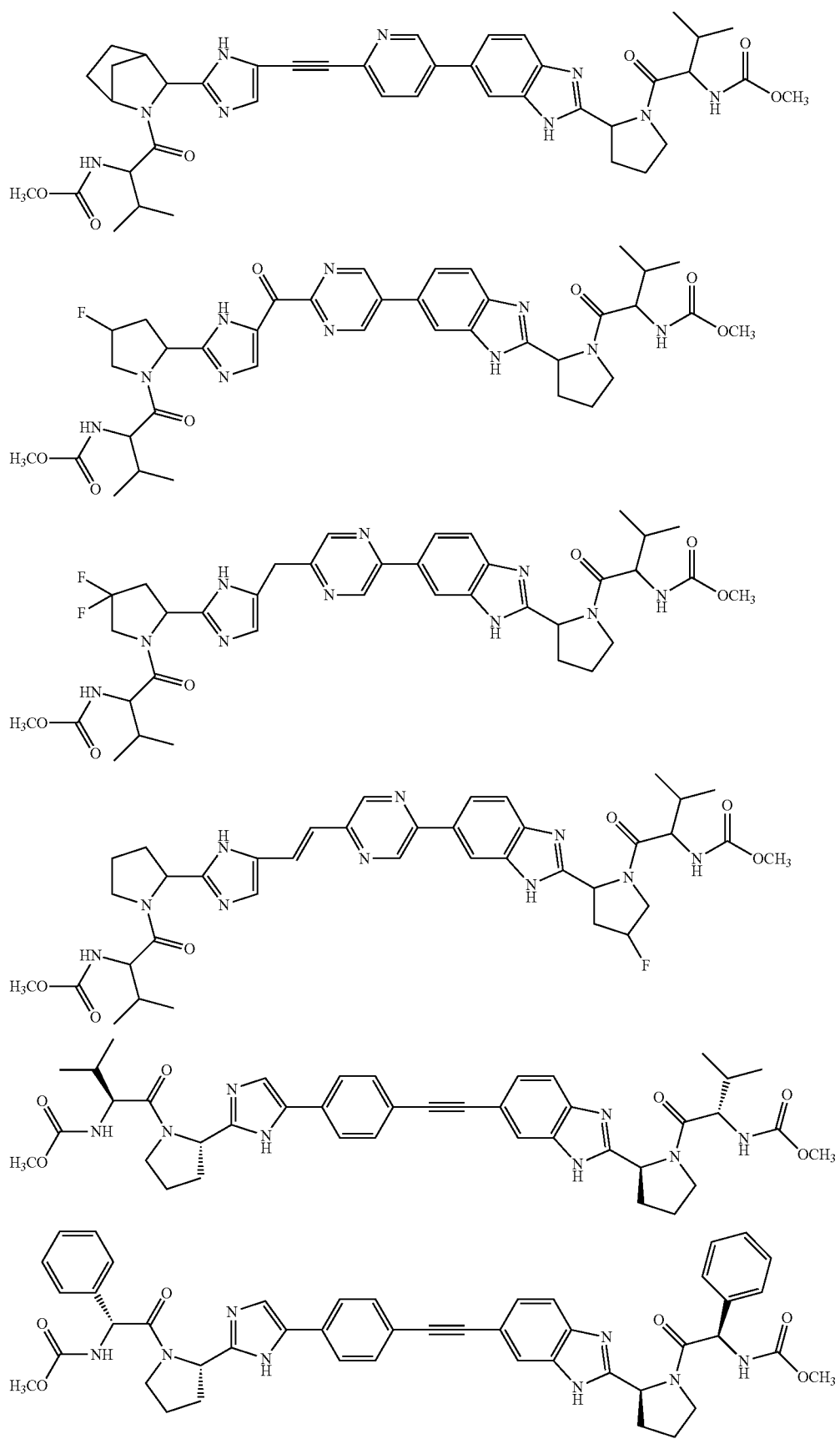

-continued
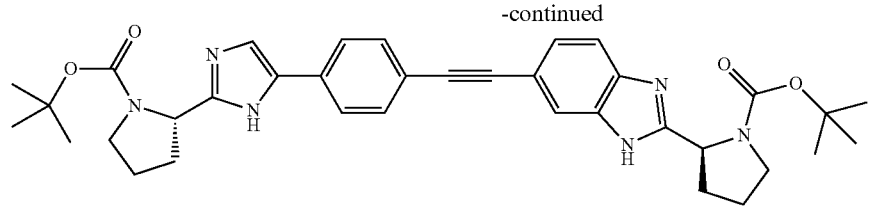
or a pharmaceutically acceptable salt thereof.
8. A pharmaceutical composition comprising at least one compound of claim 1 or a pharmaceutically acceptable salt thereof, and at least one pharmaceutically acceptable carrier.
* * * * *